US006331302B1

(12) United States Patent
Bennett et al.

(10) Patent No.: US 6,331,302 B1
(45) Date of Patent: *Dec. 18, 2001

(54) PROTEIN TYROSINE KINASE AGONIST ANTIBODIES

(75) Inventors: Brian D. Bennett, Thousand Oaks; David Goeddel, Hillsborough; James M. Lee, San Bruno; William Matthews, Woodside; Siao Ping Tsai, South San Francisco; William I. Wood, Hillsborough, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/446,648

(22) PCT Filed: Apr. 4, 1995

(86) PCT No.: PCT/US95/04228

§ 371 Date: May 23, 1995

§ 102(e) Date: May 23, 1995

(87) PCT Pub. No.: WO95/27061

PCT Pub. Date: Oct. 12, 1995

Related U.S. Application Data

(63) Continuation-in-part of application No. 08/222,616, filed on Apr. 4, 1994, now Pat. No. 5,635,177, which is a continuation-in-part of application No. PCT/US93/00586, filed on Jan. 22, 1993, which is a continuation-in-part of application No. 07/826,935, filed on Jan. 22, 1992, now abandoned.

(51) Int. Cl.[7] .................................................. A61K 39/395

(52) U.S. Cl. ..................................... 424/146.1; 424/143.1; 424/141.1; 424/130.1; 530/387.1; 530/388.1; 530/388.26

(58) Field of Search .............................. 530/387.1, 388.1, 530/388.26; 424/143.1, 141.1, 130.1, 146.1

(56) References Cited

U.S. PATENT DOCUMENTS

| 5,185,438 | * | 2/1993 | Lemischka ......................... 536/23.2 |
| 5,635,177 |   | 6/1997 | Bennett et al. ................... 424/143.1 |
| 5,776,755 |   | 7/1998 | Alitalo et al. ........................ 435/194 |

FOREIGN PATENT DOCUMENTS

| WO 92/14748 | 9/1992 | (WO) . |
| WO 93/10136 | 5/1993 | (WO) . |
| WO 93/15201 | 8/1993 | (WO) . |
| WO 95/14776 | 6/1995 | (WO) . |

OTHER PUBLICATIONS

Sambrook et al., Molecular Cloning, A Laboratory Manual, 2nd Edition, vol. 3, 16.2–16.30 and 17.3 to 17.28, 1989, Cold Spring Harbor, Cold Spring Harbor Laboratory Press, 1989.*

Tartaglia et al., J. Biol. Chem. vol. 267, 4304–4307, 1992.*
Beguinot et al., J. Biol. Chem., 261, 1801–1807, Feb. 5, 1986.*
Colwell et al., Methods in Enzymology, 121, 42–51 1986.*
Dunbar et al., Methods in Enzymology, 182, 663–670, 1990.*
Aprelikova et al., "FLT4, a Novel Class III Receptor Tyrosine Kinase in Chromosome 5q33–gter[1]" *Cancer Research* 52:746–748 (1992).
Ashman et al., "Epitope Mapping and Functional Studies with Three Monoclonal Antibodies to the C–KIT Receptor Tyrosine Kinase, YB5.B8, 17F11, and SR–1" *Journal of Cellular Physiology* 158:545–554 (1994).
Bennett et al., "Cloning and Characterization of HTK, a Novel Transmembrane Tyrosine Kinase of the EPH Subfamily" *Journal of Biological Chemistry* 269(19):14211–14218 (1994).
Bennett et al., "Extracellular Domain–IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060–23067 (Dec. 5, 1991).
Bennett et al., "Molecular Cloning of a Ligand for the EPH–Related Receptor Protein–Tyrosine Kinase Htk" *Proc. Natl. Acad. Sci. USA* 92:1866–1870 (1995).
Bohme et al., "PCR mediated detection of a new human receptor–tyrosine–kinase, HEK 2" *Oncogene* 8:2857–2862 (1993).
Brauninger et al., "Isolation and Characterization of a Human Gene That Encodes a New Subclass of Protein Tyrosine Kinases" *Gene* 110(2):205–211 (1992).
Brizzi et al., "Hematopoietic Growth Factor Receptors" *International Journal of Cell Cloning* 9:274–300 (1991).
Carraway et al., "A Neu Acquaintance for ErbB3 and ErbB4: A Role for Receptor Heterodimerization in Growth Signaling" *Cell* 78:5–8 (Jul. 15, 1994).
Finnerty et al., "Molecular Cloning of Murine FLT and FLT4" *Oncogene* 8:2293–2298 (1993).
Gabrilove et al., "Augmentation of GM–CSF supported progenitor cell growth and partial abrogation of TGF–beta mediated suppression by basic bFGF" *Blood* Abstract No. 42:13a (1991).

(List continued on next page.)

Primary Examiner—Yvonne Eyler
Assistant Examiner—Eileen B. O'Hara
(74) Attorney, Agent, or Firm—David A. Carpenter, Ph.D.

(57) ABSTRACT

Agonist antibodies are disclosed which bind to the extracellular domain of receptor protein tyrosine kinases pTKs, and thereby cause dimerization and activation of the intracellular tyrosine kinase domain thereof. The antibodies are useful for activating their respective receptor and thereby enabling the role of the tyrosine kinase receptor in cell growth and/or differentiation to be studied. Chimeric proteins comprising the extracellular domain of the receptor pTKs and an immunoglobulin constant domain sequence are also disclosed.

6 Claims, 54 Drawing Sheets

OTHER PUBLICATIONS

Galland et al., "Chromosomal Localization of FLT4, a Novel Receptor–Type Tyrosine Kinase Gene" *Genomics* 13:475–478 (1992).

Galland et al., "The FLT4 Gene Encodes a Transmembrane Tyrosine Kinase Related to the Vascular Endothelial Growth Factor Receptor" *Oncogene* 8:1233–1240 (1993).

Gilardi–Hebenstreit et al., "An Eph–related receptor protein tyrosine kinase gene segmentally expressed in the developing mouse hindbrain" *Oncogene* 7:2499–2506 (1992).

Guy et al., "Insect Cell–expressed p180$^{erbB3}$ Possesses an Impaired Tyrosine Kinase Activity" *Proc. Natl. Acad. Sci. USA* 91:8132–8136 (Aug. 1994).

Hanks et al., "The Protein Kinase Family: Conserved Features and Deduced Phylogeny of the Catalytic Domains" *Science* 241:42–52 (1988).

Hao et al., "Isolation and Sequence Analysis of a Novel Human Tyrosine Kinase Gene" *Molecular & Cellular Biology* 9(4):1587–1593 (1989).

Hirai et al., "A novel putative tyrosine kinase receptor encoded by the eph gene" *Science* 238:1717–1720 (1987).

Holtrich et al., "Two Additional Protein–Tyrosine Kinases Expressed in Human Lung: Fourth Member of the Fibroblast Growth Factor Receptor Family and an Intracellular Protein–Tyrosine" *Proc. Natl. Acad. Sci.* 88:10411–10415 (1991).

Honma et al., "Induction by some protein kinase inhibitors of differentiation of a mouse megakaryoblastic cell line established by coinfection with Abelson murine leukemia virus and recombinant SV40 retrovirus" *Cancer Research* 51:4649–4655 (1991).

Juretic et al., "Structure of the genes of two homologous intracellularly heterotopic isoenzymes" *European Journal of Biochemistry* 192:119–126 (1990).

Kaipainen et al., "The Related FLT4, FLT1, and KDR Receptor Tyrosine Kinases Show Distinct Expression Patterns in Human Fetal Endothelial Cells" *Journal of Experimental Medicine* 178:2077–2088 (1993).

Kanakura et al., "Phorbol 12–myristate 13–acetate inhibits granulocyte–macrophage colony stimulating factor–induced protein tyrosine phosphorylation in a human factor–dependent hematopoietic cell line" *Journal of Biological Chemistry* 266:490–495 (1991).

Kanakura et al., "Signal transduction of the human granulocyte–macrophage colony–stimulating factor and interleukin–3 receptors involves tyrosine phosphorylation of a common set of cytoplasmic proteins" *Blood* 76:706–715 (1990).

Kornbluth et al., "Novel Tyrosine Kinase Identified by Phosphotyrosine Antibody Screening of cDNA Libraries" *Molecular & Cellular Biology* 8(12):5541–5544 (1988).

Lai et al., "An Extended Family of Protein–Tyrosine Kinase Genes Differentially Expressed in the Vertebrate Nervous System" *Neuron* 6:691–704 (May 1991).

Letwin et al., "Novel protein–tyrosine kinase cDNAs related to fps/fes and eph cloned using anti–phosphotyrosine antibody" *Oncogene* 3:621–627 (1988).

Lhotak et al., "Biological and biochemical activities of a chimeric epidermal growth factor–Elk receptor tyrosine kinase" *Molecular & Cellular Biology* 13(11):7071–7079 (1993).

Lhotak et al., "Characterization of elk, a brain–specific receptor tyrosine kinase" *Molecular & Cellular Biology* 11(5):2496–2502 (1991).

Lindberg et al., "cDNA cloning and characterization of eck, an epithelial cell receptor protein–tyrosine kinase in the eph/elk family of protein kinases" *Molecular & Cellular Biology* 10(12):6316–6324 (1990).

Maisonpierre et al., "Ehk–1 and Ehk–2: two novel members of the Eph receptor–like tyrosine kinase family with distinctive structures and neuronal expression" *Oncogene* 8:3277–3288 (1993).

Mark et al., "Expression and Characterization of Hepatocyte Growth Factor Receptor–IgG Fusion Proteins" *The Journal of Biological Chemistry* 267(36):26166–26171 (Dec. 25, 1992).

Matthews et al., "A receptor tyrosine kinase specific to hematopoietic stem and progenitor cell–enriched populations" *Cell* 65:1143–1152 (1991).

Miura et al., "Induction of tyrosine phosphorylation by the erythropoietin receptor correlates with mitogenesis" *Molecular & Cellular Biology* 11:4895–4902 (1991).

Pajusola et al., "FLT4 Receptor Tyrosine Kinase Contains Seven Immunglobulin like loops and is Expressed in Multiple Human Tissues and Cell Lines" *Cancer Research* 52:5738–5743 (1992).

Pajusola et al., "Two Human FLT4 Receptor Tyrosine Kinase Isoforms with Distinct Carboxy Terminal Tails are Produced by Alternative Processing of Primary Transcripts" *Oncogene* 8:2931–2937 (1993).

Partanen et al., "Putative Tyrosine Kinases Expressed in K–562 Human Leukemia Cells" *Proc. Natl. Acad. Sci.* 87:8913–8917 (1990).

Pasquale, E., "Identification of chicken embryo kinase 5, a developmentally regulated receptor–type tyrosine kinase of the Eph family" *Cell Regulation* 2:523–534 (1991).

Queen et al., "A humanized antibody that binds to the interleukin 2 receptor" *Proc. Natl. Acad. Sci. USA* 86(24):10029–10033 (Dec. 1989).

Rapraeger et al., "Requirement of heparan sulfate for bFGF–mediated fibrobalst growth and myoblast differentiation" *Science* 252:1705–1708 (1991).

Rescigno et al., "A putative receptor tyrosine kinase with unique structural topology" *Oncogene* 6:1909–1913 (1991)

Rosnet et al., "Murine Flt3, a gene encoding a novel tyrosine kinase receptor of the PDGFR/CSF1R family" *Oncogene* 6:1641–1650 (1991).

Sajjadi et al., "Five Novel Avian Eph–related Tyrosine Kinases are Differentially Expressed" *Oncogene* 8:1807–1813 (1993).

Sajjadi et al., "Identification of a new eph–related receptor tyrosine kinase gene from mouse and chicken that is developmentally regulated and encodes at least two forms of the receptor" *New Biol.* 3(8):769–778 (1991).

Sarup, "Characterization of an Anti–P185$^{her2}$ Monoclonal Antibody that Stimulates Receptor Function and Inhibits Tumor Cell Growth" *Growth Regulation* 1:72–82 (1991).

Ullrich et al., "Signal Transduction by Receptors with Tyrosine Kinase Activity" *Cell* 81:203–212 (1990).

Wicks et al., "Molecular cloning of HEK, the gene encoding a receptor tyrosine kinase expressed by human lymphoid tumor cell lines" *Proc. Natl. Acad. Sci.* 89:1611–1615 (1992).

Wilks, "Two putative protein–tyrosine kinases identified by application of the polymerase chain reaction" *Proc. Natl. Acad. Sci. USA* 86:1603–1607 (1989).

Wilks et al., "The application of the polymerase chain reaction to cloning members of the protein tyrosine kinase family" *Gene* 85:67–74 (1989).

Wilks et al., "Two novel protein–tyrosine kinases, each with a second phosphotransferase–related catalytic domain, define a new class of protein kinase" *Molecular & Cellular Biology* 11:2057–2065 (1991).

Yarden, "Agonistic Antibodies Stimulate the Kinase Encoded by the neu Protooncogene in Living Cells but the Oncogenic Mutant is Constitutively Active" *Proc. Natl. Acad. Sci. USA* 87:2569–2573 (1990).

Yarden et al., "Experimental approaches to hypothetical hormones: detection of a candidate ligand of the neu protooncogene" *Proc. Natl. Acad. Sci. USA* 86:3179–3183 (1989).

Zeigler et al., "Cellular and Molecular Characterization of the Role of the FLK–2/FLT–3 Receptor Tyrosine Kinase in Hematopoietic Stem Cells" *Blood* 84(8):2422–2430 (1994).

* cited by examiner-

FIG. 1A

GGATCCTGTG CATCAGTGAC TTAGGGCTAG GAACATTCTG CTGTCGGAAA GCGACGTGGT 60

GAAGATCTGT GACTTTGGCC TTGCCCGGGA CATCTACAAA GACCCCAGCT ACGTCCGCAA 120

GCATGCCCGG CTGCCCCTGA AGTGGATGGC GCCAGAATTC 160

FIG. 1B

Asp Pro Val His Gln Xaa Leu Arg Arg Ala Arg Asn Ile Leu Leu Ser Glu
1               5                   10                  15

Ser Asp Val Val Lys Ile Cys Asp Phe Gly Leu Ala Arg Asp Ile Tyr
            20                  25                  30

Lys Asp Pro Ser Tyr Val Arg Lys His Ala Arg Leu Pro Leu Lys Trp
            35                  40                  45

Met Ala Pro Glu Phe
        50

FIG. 2A

```
GGATCCATTC ACAGAGACCT AGCAGCACGC AACATCCTGG TCTCAGAGGA CCTGGTAACC   60
AAGGTCAGCG ACTTTGGCCT GGCCAAAGCC GAGCGGAAGG GGCTAGACTC AAGCCCGGCTG  120
CCCGTCAAAT GGATGGCTCC CGAATTC                                       147
```

FIG. 2B

```
Gly Ser Ile His Arg Asp Leu Ala Ala Arg Asn Ile Leu Val Ser Glu
1               5                   10                  15
Asp Leu Val Thr Lys Val Ser Asp Phe Gly Leu Ala Lys Ala Glu Arg
            20                  25                  30
Lys Gly Leu Asp Ser Ser Arg Leu Pro Val Lys Trp Met Ala Pro Glu
        35                  40                  45
Phe
```

FIG. 3A

```
GTT GGA ATT CCT TCC GGC GCC ATC CAT TTC ACC GGC AGC TTT ATT TCG    48
Val Gly Ile Pro Ser Gly Ala Ile His Phe Thr Gly Ser Phe Ile Ser
 1               5                  10                  15

TGT CTA GAT TCA TAG ATG TCT TCA TTA TCT ACC TTA AAA ACT CTG GCA    96
Cys Leu Asp Ser Met Ser Ser Leu Ser Thr Leu Lys Thr Leu Ala
         20                  25                  30

AGT CCA AAA TCT GCT ACT TTG TAG ATA TTA TGT TCA CCA ACG AGG ACA   144
Ser Pro Lys Ser Ala Thr Leu     Ile Leu Cys Ser Pro Thr Arg Thr
         35                  40                  45

TTCCT                                                              149
Phe
```

FIG. 3B

```
GTG CAC AGG GAT CTC GCG GCT CGG AAC ATC CTC GTC GGG GAA AAC ACC    48
Val His Arg Asp Leu Ala Ala Arg Asn Ile Leu Val Gly Glu Asn Thr
 1               5                  10                  15

CTC TCG AAA GTT GTG GAC TTC GGG TTA GCC AGG CTT ATC AAG GAG GAC    96
Leu Ser Lys Val Val Asp Phe Gly Leu Ala Arg Leu Ile Lys Glu Asp
         20                  25                  30

GTC TAC CTC TCC CAT GAC CAC AAT ATC CCC TAC AAA TGG ATG GCC CCT   144
Val Tyr Leu Ser His Asp His Asn Ile Pro Tyr Lys Trp Met Ala Pro
         35                  40                  45

GAG GGA A                                                          151
Glu Gly
     50
```

FIG. 3C

```
GTT CAC CGA GAT CTC AAG TCC AAC AAC ATT TTG CTG CTG CAG CCC ATT      48
Val His Arg Asp Leu Lys Ser Asn Asn Ile Leu Leu Leu Gln Pro Ile
 1               5                  10                  15

GAG AGT GAC GAC ATG GAG CAC AAG ACC CTG AAG ATC ACC GAC TTT GGC      96
Glu Ser Asp Asp Met Glu His Lys Thr Leu Lys Ile Thr Asp Phe Gly
                 20                  25                  30

CTG GCC CGA GAG TGG CAC AAA ACC ACA CAA ATG AGT GCC GC              137
Leu Ala Arg Glu Trp His Lys Thr Thr Gln Met Ser Ala
                 35                  40                  45
```

FIG. 3D

```
GTC AAT CGT GAC CTC GCC CGA AAT GTG TTG CTA GTT ACC CAA CAT          48
Val Asn Arg Asp Leu Ala Arg Asn Val Leu Leu Val Thr Gln His
 1               5                  10                  15

TAC GCC AAG ATC AGT GAT TTC GGA CTT TCC AAA GCA CTG CGT GCT GAT      96
Tyr Ala Lys Ile Ser Asp Phe Gly Leu Ser Lys Ala Leu Arg Ala Asp
                 20                  25                  30

GAA AAC TAC TAC AAG GCC CAG ACC CAT GGA AAG TGG CCT GTC AAG TGG     144
Glu Asn Tyr Tyr Lys Ala Gln Thr His Gly Lys Trp Pro Val Lys Trp
                 35                  40                  45

TAC GCT CCG GAA TGC ATC AAC TAC TAC AAG TTC TCC AGC AAA AGC GAT     192
Tyr Ala Pro Glu Cys Ile Asn Tyr Tyr Lys Phe Ser Ser Lys Ser Asp
 50                  55                  60

GTC TGG TCC TTT GGA ATT C                                           211
Val Trp Ser Phe Gly Ile
 65              70
```

FIG. 4A

| | | | | | |
|---|---|---|---|---|---|
| TTCGAGCTCG | CCCGACATTG | ATTATTGACT | AGTAATCAAT | TACGGGGTCA | 60 |
| TTAGTTCATA | GCCCATATAT | GGAGTTCCGC | GTTACATAAC | TTACGGTAAA | TGGCCCGCCT | 120 |
| GGCTGACCGC | CCAACGACCC | CCGCCCATTG | ACGTCAATAA | TGACGTATGT | TCCCATAGTA | 180 |
| ACGCCAATAG | GGACTTTCCA | TTGACGTCAA | TGGGTGGAGT | ATTACGGTA | AACTGCCCAC | 240 |
| TTGGCAGTAC | ATCAAGTGTA | TCATATGCCA | AGTACGCCCC | CTATTGACGT | CAATGACGGT | 300 |
| AAATGGCCCG | CCTGGCATTA | TGCCCAGTAC | ATGACCTTAT | GGGACTTTCC | TACTTGGCAG | 360 |
| TACATCTACG | TATTAGTCAT | CGCTATTACC | ATGGTGATGC | GGTTTTGGCA | GTACATCAAT | 420 |
| GGGCGTGGAT | AGCGGTTTGA | CTCACGGGGA | TTTCCAAGTC | TCCACCCCAT | TGACGTCAAT | 480 |
| GGGAGTTTGT | TTTGGCACCA | AAATCAACGG | GACTTTCCAA | AATGTCGTAA | CAACTCCGCC | 540 |
| CCATTGACGC | AAATGGGCGG | TAGGCGTGTA | CGGTGGGAGG | TCTATATAAG | CAGAGCTCGT | 600 |
| TTAGTGAACC | GTCAGATCGC | CTGGAGACGC | CATCCACGCT | GTTTTGACCT | CCATAGAAGA | 660 |
| CACCGGGACC | GATCCAGCCT | CCGCGGCCGG | GAACGGTGCA | TTGGAACGCG | GATTCCCCGT | 720 |
| GCCAAGAGTG | ACGTAAGTAC | CGCCTATAGA | GTCTATAGGC | CCACTTGGCT | TCGTTAGAAC | 780 |
| GCGGCTACAA | TTAATACATA | ACCTTATGTA | TCATACACAT | ACGATTTAGG | TGACACTATA | 840 |
| GAATAACATC | CACTTTGCCT | TTCTCTCCAC | AGGTGTCCAC | TCCCAGTTC | AACTGCACCT | 900 |
| CGGTTCTATC | GATTGAATTC | CCCGGGGATC | CTCTAGAGAT | CCCTCGACCT | CGAGATCCAT | 960 |
| TGTGCTGGCG | CGGATTCTTT | ATCACTGATA | AGTTGGTGGA | CATATTATGT | TTATCAGTGA | 1020 |

FIG. 4B

| | | | | | |
|---|---|---|---|---|---|
|TAAAGTGTCA|AGCATGACAA|AGTTGCAGCC|GAATACAGTG|ATCCGTGCCG|CCCTAGACCT|1080|
|GTTGAACGAG|GTCGGGCTAG|ACGGTCTGAC|GACACGCAAA|CTGGCGGAAC|GGTTGGGGGT|1140|
|TCAGCAGCCG|GCGCTTTACT|GGCACTTCAG|GAACAAGCGG|GCGCTGCTCG|ACGCACTGGC|1200|
|CGAAGCCATG|CTGGCGGAGA|ATCATAGCAC|TTCGGTGCCG|AGAGCCGACG|ACGACTGGCG|1260|
|CTCATTTCTG|ACTGGGAATG|CCCGCAGCTT|CAGGCAGGCG|CTGCTCGCCT|ACCGCCAGCA|1320|
|CAATGGATCT|CGAGGGATCT|TCCATACCTA|CCAGTTCTGC|GCCTGCAGGT|CGCGGCCGCA|1380|
|CTACTCTTTG|ATGTATTACT|CATATTACCA|AGGAATAACT|GGCGGGCACA|GGTCAGGTG|1440|
|CTGAAGGGAC|ATTGTGAGAA|GTGACCTAGA|AGGCAAGAGG|TGAGCCCTCT|GTCACGCTGG|1500|
|CATAAGGGCC|GCTTGAGGGC|TCTTTGGTCA|AGCAGTAACG|CCAGTGTCTG|GGAAGGCACC|1560|
|TGTTACTCAG|CAGACCATGA|AAGGGCGTCT|CCCTTTCCTT|GGAGCAGTCA|GGGAACACTC|1620|
|TGCTCCACCA|GCTTCTTGTG|GGAGCCTGGA|TATTATCCAG|GCCTGCCCGC|AGTCATCCGG|1680|
|AGGCCTAACC|CCTCCCTGTG|GTGCTTCAGT|GGTCACACTC|CTTGTCCACT|TTCATGCTCC|1740|
|TCTTGGCCTC|CTGGTTCCTC|TTGGAAGTTT|GTAGTAGATA|GCAGAAGAAA|TAGCGAAAGT|1800|
|CTTAAAGTCT|TTGATCTTTC|TTATAAGTGC|AGAGAAGAAA|TGCTGACGTA|TGCTGCCTTC|1860|
|TCTCTCTCTG|CTTCAGCTAC|CTGAAGCCGC|TTTCTTGTCT|ATACCTGCTC|TCTATCTGCT|1920|
|CACACTCCTC|CGAGGCCAGC|ACCATCCCAC|TGTCTGTCTG|GTTGTCCACA|GAGCCTTTGT|1980|
|AGTCGTTGG|GGTCATGGGG|AATTCCCTCAA|ATGTCTTCAT|CCTGGAGGAA|CCACGGGTCT|2040|

FIG. 4C

```
CAGCCCCTCT GGCCAGGCAC CCGGGAAAGG ACACCCAGTT GTAATACCTG GCGGCCAGGC  2100
TGTGGGCTG  CAGGCTTGGC GGGCTGTCCT CAGCGTCAGC CTGGGGGATG TGTAGGGCCA  2160
TGGTGGACAC CTGCGAGAAG CTGCCCCTCT CTGAGCTCTG AGAGCTGCGC GGGGCCATGC  2220
AGACCTCCTC TTCCTCTTGC AGGCCCCTGC CCTGGAGCAG GTCCCCCAGG ATCTCCACCA  2280
GCTCCGAGAA TGCAGGTCTC GCCTTGGGGT CTCCGGACCA GCAGTTCAGC ATGATGCGGC  2340
GTATGGCGGG AGTGGCCAGC TCCGGGGCCC TCATCCTTGT GCCGTCTCTC AGCCGCTGGC  2400
AGAACTCCTC ATTGATCTGC ACCCCAGGGT ACGGGGAGGC CCCCAGAGAG AAGATCTCCC  2460
AGAGAAGCAC CCCAAAGGAC CACACGTCAC TCTGCGTGGT GTACACCTTG TCGAAGATGC  2520
TTTCAGGGGC CATCCACTTC AGGGGCAGCC GGGCACTGCC CTTGCGGACG TAGTCGGGGT  2580
CTTTGTAGAT GTCCCGGGCA AGCCAAAGT  CACAGATCTT CACCACGTCG CTTTCCGACA  2640
GCAGAATGTT CCGAGCAGCC AGGTCTCTGT GGATGCACTT TCGGGAAGCC AGGAACTCCA  2700
TCCCTCTGGC CACCTGGAAG CTGTAGCAGA CAAGATCTTC CATGGTCAGC GGGCTCAGCC  2760
ACAGGTCCTC AGCTTCTTGG TCTGGAGAAG CCCGCCCTCG TCCGCCCTCG GTCTTCCGAGA  2820
ACCGCGCGAA GAGGACCCTG TCGCTGCTCC CCGGCCGCCT CCGATCCAGC CTGGCGAGCT  2880
CCACCATGGC GCGGAAGCGT CCGGCTGCT  CGGGAGACTT CTCCTGCGGA TGCACGAAGC  2940
TGGCTCGAGG GCGCCCCAGTC GTCCGCCGCA GAGGCGCCTC CATTCCCCCG CCGCCCCGGG  3000
CGCCCCGCAG GCCGCCCGCT CACCGNGCAG GGGCTGCGGC CGCGACTCTA GAGTCGACCT  3060
```

FIG. 4D

| | | | | | |
|---|---|---|---|---|---|
| GCAGAAGCTT | GGCCGCCATG | GCCCAACTTG | TTTATTGCAG | CTTATAATGG | TTACAAATAA | 3120
| AGCAATAGCA | TCACAAATTT | CACAAATAAA | GCATTTTTT | CACTGCATTC | TAGTTGTGGT | 3180
| TTGTCCAAAC | TCATCAATGT | ATCTTATCAT | GTCTGGATCG | ATCGGGAATT | AATTCGGCGC | 3240
| AGCACCATGG | CCTGAAATAA | CCTCTGAAAG | AGGAACTTGG | TTAGGTACCT | TCTGAGGCGG | 3300
| AAAGAACCAG | CTGTGGAATG | TGTGTCAGTT | AGGGTGTGGA | AAGTCCCCAG | GCTCCCCAGC | 3360
| AGGCAGAAGT | ATGCAAAGCA | TGCATCTCAA | TTAGTCAGCA | ACCAGGTGTG | GAAAGTCCCC | 3420
| AGGCTCCCCA | GCAGGCAGAA | GTATGCAAAG | CATGCATCTC | AATTAGTCAG | CAACCATAGT | 3480
| CCCGCCCCCA | ACTCCGCCCA | TCCCGCCCCT | AACTCCGCCC | AGTTCCGCCC | ATTCTCCGCC | 3540
| CCATGGCTGA | CTAATTTTTT | TTATTTATGC | AGAGGCCGAG | GCCGCCTCGG | CCTCTGAGCT | 3600
| ATTCCAGAAG | TAGTGAGGAG | GCTTTTTTGG | AGGCCTAGGC | TTTTGCAAAA | AGCTGTAAC | 3660
| AGCTTGGCAC | TGGCCGTCGT | TTTACAACGT | CGTGACTGGG | AAAACCCTGG | CGTTACCCAA | 3720
| CTTAATCGCC | TTGCAGCACA | TCCCCCCTTC | GCCAGCTGGC | GTAATAGCGA | AGAGGCCCGC | 3780
| ACCGATCGCC | CTTCCCAACA | GTTGCGTAGC | CTGAATGGCG | AATGGCGCCT | GATGCGGTAT | 3840
| TTTCTCCTTA | CGCATCTGTG | CGGTATTTCA | CACCGCATAC | GTCAAAGCAA | CCATAGTACG | 3900
| CGCCCTGTAG | CGGCGCATTA | AGCGCGGCGG | GTGTGGTGGT | TACGGCCAGC | GTGACCGCTA | 3960
| CACTTGCCAG | CGCCCTAGCG | CCCGCTCCTT | TCGCTTTCTT | CCCTTCCTTT | CTCGCCACGT | 4020
| TCGCCGGCTT | TCCCCGTCAA | GCTCTAAATC | GGGGGCTCCC | TTTAGGGTTC | CGATTTAGTG | 4080

FIG. 4E

```
CTTTACGGCA CCTCGACCCC AAAAAACTTG ATTTGGGTGA TGGTTCACGT AGTGGGCCAT 4140
CGCCCTGATA GACGGTTTTT CGCCCTTTGA CGTTGGAGTC CACGTTCTTT AATAGTGGAC 4200
TCTTGTTCCA AACTGGAACA ACACTCAACC CTATCTCGGG CTATTCTTTT GATTTATAAG 4260
GGATTTTGCC GATTTCGGCC TATTGGTTAA AAAATGAGCT GATTTAACAA AAATTTAACG 4320
CGAATTTTAA CAAAATATTA ACGTTTACAA TTTTATGGTG CACTCTCAGT ACAATCTGCT 4380
CTGATGCCGC ATAGTTAAGC CAACTCCGCT ATCGCTACGT GACTGGGTCA TGGCTGCGCC 4440
CCGACACCCG CCAACACCCG CTGACGCGCC CTGACGGGCT TGTCTGCTCC CGGCATCCGC 4500
TTACAGACAA GCTGTGACCG TCTCCGGGAG CTGCATGTGT CAGAGGTTTT CACCGTCATC 4560
ACCGAAACGC GCGAGGCAGT ATTCTTGAAG ACGAAAGGGC CTCGTGATAC GCCTATTTTT 4620
ATAGGTTAAT GTCATGATAA TAATGGTTTC TTAGACGTCA GGTGGCACTT TTCGGGGAAA 4680
TGTGCGCGGA ACCCCTATTT GTTTATTTTT CTAAATACAT TCAAATATGT ATCCGCTCAT 4740
GAGACAATAA CCCTGATAAA TCTTCAATA ATATTGAAAA AGGAAGAGTA TGAGTATTCAA 4800
ACATTTCCGT GTCGCCCTTA TTCCCTTTTT GCGGCATTT TGCCTTCCTG TTTTTGCTCA 4860
CCCAGAAACG CTGGTGAAAG TAAAAGATGC TGAAGATCAG TTGGGTGCAC GAGTGGGTTA 4920
CATCGAACTG GATCTCAACA GCGGTAAGAT CCTTGAGAGT TTTCGCCCCG AAGAACGTTT 4980
TCCAATGATG AGCACTTTTA AAGTTCTGCT ATGTGGCGCG GTATTATCCC GTGATGACGC 5040
CGGGCAAGAG CAACTCGGTC GCCGCATACA CTATTCTCAG AATGACTTGG TTGAGTACTC 5100
```

FIG. 4F

```
ACCAGTCACA GAAAAGCATC TTACGGATGG CATGACAGTA AGAGAATTAT GCAGTGCTGC    5160
CATAACCATG AGTGATAACA CTGCCGGCCAA CTTACTTCTG ACAACGATCG GAGGACCGAA   5220
GGAGCTAACC GCTTTTTTGC ACAACATGGG GGATCATGTA ACTCGCCTTG ATCGTTGGGA    5280
ACCGGAGCTG AATGAAGCCA TACCAAACGA CGAGCGTGAC ACCACGATGC CAGCAGCAAT    5340
GGCAACAACG TTGCGCAAAC TATTAACTGG CGAACTACTT ACTCTAGCTT CCCGGCAACA    5400
ATTAATAGAC TGGATGGAGG CGGATAAAGT TGCAGGACCA CTTCTGCGCT CGGCCCCTTCC   5460
GGCTGGCTGG TTTATTGCTG ATAAATCTGG AGCCGGTGAG CGTGGGTCTC GCGGTATCAT    5520
TGCAGCACTG GGGCCAGATG GTAAGCCCTC CCGTATCGTA GTTATCTACA CGACGGGGAG    5580
TCAGGCAACT ATGGATGAAC GAAATAGACA GATCGCTGAG ATAGGTGCCT CACTGATTAA    5640
GCATTGGTAA CTGTCAGACC AAGTTTACTC ATATATACTT TAGATTGATT TAAAACTTCA    5700
TTTTTAATTT AAAAGGATCT AGGTGAAGAT CCTTTTTGAT AATCTCATGA CCAAAATCCC    5760
TTAACGTGAG TTTTCGTTCC ACTGAGCGTC AGACCCCGTA CTGCTTGCAA GAAAAGATCA AAGGATCTTC 5820
TTGAGATCCT TTTTTTCTGC GCGTAATCTG CTGCTTGCAA ACAAAAAAAC CACCGCTACC   5880
AGCGGTGGTT TGTTTGCCGG ATCAAGAGCT ACCAACTCTT TTTCCGAAGG TAACTGGCTT    5940
CAGCAGAGCG CAGATACCAA ATACTGTCCT TCTAGTGTAG CCGTAGTTAG GCCACCACTT    6000
CAAGAACTCT GTAGCACCGC CTACATACCT CGCTCTGCTA ATCCTGTTAC CAGTGGCTGC    6060
TGCCAGTGGC GATAAGTCGT GTCTTACCGG GTTGGACTCA AGACGATAGT TACCGGATAA    6120
```

FIG. 4G

| | | | | |
|---|---|---|---|---|
| GGCGCAGCGG | TCGGGCTGAA | CCGGGGGTTC | GTGCACACAG | CCCAGCTTGG | AGCGAACGAC | 6180 |
| CTACACCGAA | CTGAGATACC | TACAGCGTGA | GCATTGAGAA | AGCGCCACGC | TTCCCGAAGG | 6240 |
| GAGAAAGGCG | GACAGGTATC | CGGTAAGCGG | CAGGGTCGGA | ACAGGAGAGC | GCACGAGGGA | 6300 |
| GCTTCCAGGG | GGAAACGCCT | GGTATCTTTA | TAGTCCTGTC | GGGTTTCGCC | ACCTCTGACT | 6360 |
| TGAGCGTCGA | TTTTGTGAT  | GCTCGTCAGG | GGGGCGGAGC | CTATGAAAAA | ACGCCAGCAA | 6420 |
| CGCGGCCTTT | TTACGGTTCC | TGGCCTTTTG | CTGGCCTTTT | GCTCACATGT | TCTTTCCTGC | 6480 |
| GTTATCCCCT | GATTCTGTGG | ATAACCGTAT | TACCGCCTTT | GAGTGAGCTG | ATACCGCTCG | 6540 |
| CCGCAGCCGA | ACGACCGAGC | GCAGCGAGTC | AGTGAGCGAG | GAAGCGGAAG | AGCGCCCAAT | 6600 |
| ACGCAAACCG | CCTCTCCCCG | CGCGTTGGCC | GATTCATTAA | TCCAGCTGGC | ACGACAGGTT | 6660 |
| TCCCGACTGG | AAAGCGGGCA | GTGAGCGCAA | CGCAATTAAT | GTGAGTTACC | TCACTCATTA | 6720 |
| GGCACCCCAG | GCTTTACACT | TTATGCTTCC | GGCTCGTATG | TTGTGTGGAA | TTGTGAGCGG | 6780 |
| ATAACAATTT | CACACAGGAA | ACAGCTATGA | CCATGATTAC | GAATTAA    |            | 6827 |

FIG. 4H

Glu Lys Ser Pro Glu Gln Arg Gly Arg Phe Arg Ala Met Val Glu Leu
1                   5                  10                  15

Ala Arg Leu Asp Arg Arg Arg Pro Gly Ser Ser Asp Arg Val Leu Phe
            20                  25                  30

Ala Arg Phe Ser Lys Thr Glu Gly Gly Ala Arg Arg Ala Ser Pro Asp
            35                  40                  45

Gln Glu Ala Glu Asp Leu Trp Leu Ser Pro Leu Thr Met Glu Asp Leu
            50                  55                  60

Val Cys Tyr Ser Phe Gln Val Ala Arg Gly Met Glu Phe Leu Ala Ser
65                  70                  75                  80

Arg Lys Cys Ile His Arg Asp Leu Ala Ala Arg Asn Ile Leu Leu Ser
            85                  90                  95

Glu Ser Asp Val Val Lys Ile Cys Asp Phe Gly Leu Ala Arg Asp Ile
            100                 105                 110

Tyr Lys Asp Pro Asp Tyr Val Arg Lys Gly Ser Ala Arg Leu Pro Leu
            115                 120                 125

Lys Trp Met Ala Pro Glu Ser Ile Phe Asp Lys Val Tyr Thr Thr Gln
130                 135                 140

Ser Asp Val Trp Ser Phe Gly Val Leu Leu Trp Glu Ile Phe Ser Leu
145                 150                 155                 160

Gly Ala Ser Pro Tyr Pro Gly Val Gln Ile Asn Glu Glu Phe Cys Gln
            165                 170                 175

Arg Leu Arg Asp Gly Thr Arg Met Arg Ala Pro Glu Leu Ala Thr Pro
            180                 185                 190

FIG. 4I

```
Ala Ile Arg Arg Ile Met Leu Asn Cys Trp Ser Gly Asp Pro Lys Ala
195                     200                     205

Arg Pro Ala Phe Ser Glu Leu Val Glu Ile Leu Gly Asp Leu Leu Gln
210                     215                     220

Gly Arg Gly Leu Gln Glu Glu Glu Val Cys Met Ala Pro Arg Ser
225                     230             235                 240

Ser Gln Ser Ser Glu Gly Ser Phe Ser Gln Val Ser Thr Met Ala
245                     250                     255

Leu His Ile Ala Gln Ala Asp Ala Glu Asp Ser Pro Pro Ser Leu Gln
260                     265                     270

Arg His Ser Leu Ala Ala Arg Tyr Asn Trp Val Ser Phe Pro Gly
275                     280                     285

Cys Leu Ala Arg Gly Ala Glu Thr Arg Gly Ser Ser Arg Met Lys Thr
290                     295                     300

Phe Glu Phe Pro Met Thr Pro Thr Thr Tyr Lys Gly Ser Val Asp
305                     310                     315             320

Asn Gln Thr Asp Ser Gly Met Val Leu Ala Ser Glu Glu Cys Glu Gln
325                     330                     335

Ile Glu Ser Arg Tyr Arg Gln Glu Ser Gly Phe Arg *
340                     345
```

FIG. 5A

```
TTCGAGCTCG CCCGACATTG ATTATTGACT AGTTATTAAT AGTAATCAAT TACGGGGTCA    60
TTAGTTCATA GCCCATATAT GGAGTTCCGC GTTACATAAC TTACGTAAA TGGCCCGCCT    120
GGCTGACCGC CCAACGACCC CCGCCCATTG ACGTCAATAA TGACGTATGT TCCCATAGTA   180
ACGCCAATAG GGACTTTCCA TTGACGTCAA TGGGTGGAGT ATTTACGGTA AACTGCCCAC   240
TTGGCAGTAC ATCAAGTGTA TCATATGCCA AGTACGCCCC CTATTGACGT CAATGACGGT   300
AAATGGCCCG CCTGGCATTA TGCCCAGTAC ATGACCTTAT GGGACTTTCC TACTTGGCAG   360
TACATCTACG TATTAGTCAT CGCTATTACC ATGGTGATGC GGTTTTGGCA GTACATCAAT   420
GGGCGTGGAT AGCGGTTTGA CTCACGGGGA TTTCCAAGTC TCCACCCCAT TGACGTCAAT   480
GGGAGTTTGT TTTGGCACCA AAATCAACGG GACTTTCCAA AATGTCGTAA CAACTCCGCC   540
CCATTGACGC AAATGGGCGG TAGGCGTGTA CGGTGGGAGG TCTATATAAG CAGAGCTCGT   600
TTAGTGAACC GTCAGATCGC CTGGAGACGC CATCCACGCT GTTTTGACCT CCATAGAAGA   660
CACCGGGACC GATCCAGCCT CCGCGGCCGG GAACGGTGCA TTGGAACGCG GATTCCCCGT   720
GCCAAGAGTG ACGTAAGTAC CGCCTATAGA GTCTATAGGC CCACTTGGCT TCGTTAGAAC   780
GCGGCTACAA TTAATACATA ACCTTATGTA TCATACACAT ACGATTTAGG TGACACTATA   840
GAATAACATC CACTTTGCCT TTCTCTCCAC AGGTGTCCAC TCCCAGGTCC AACTGCACCT   900
CGGTTCTATC GATTGAATTC CCCGGGGATC CTCTAGAGAT CCCTCGACCT CGAGTCGACT   960
TTTTTTTTT TTTTTGTAGG CCAAAGGTA CTTCTTTTC TTTATTAATT ACTCAGAAGT    1020
```

FIG. 5B

```
CTAGGCCACA GCAATCTACT GTTCTCCTCT CATTTCCTA AACTATTTG ATACCTATTT    1080
CTCAGACTTT ATGGGCTATT AGACATTTCT CACATTTCCA TAGATAATAA CTCATCCGTT    1140
TTGCAACCTG ATTCTCAATA TTAAGAGATT AAAACTAATG TATATGACTC TCAGTTGACA    1200
CATACTGAAG TACAGAAAAA TTCCATCATT TCCTTCTGCA AATGAAAAA GACTTCGTTT    1260
TCTCAACAGC TGCATCATTT TTTTATGCAT AGAAAAAAAT GTGCAATTAC TCCAAGTACA    1320
ATCAAGTCAT TTAACATGGC TTTACCATCA TTGTAGTTAC AGGATATTTT AAAAGAGAAA    1380
AAAAAATCTC AAAGCACAGG TCCTGCTGTG CAGCAAAGCA ATCAAATTCC TTCATAATAA    1440
CAGCCTGATG GGATTCAGCA ATCTGAGGAA TAATGAATAA CCACTCTAAT CAGTAAACAG    1500
GAAAATGCTA CAACAGTCAC TGAGTAAAAA TTGGACTATC ATCTGTTGAT TCTCTTGATC    1560
GACATTTCAA ACAATAAATG GAAATGTAAG TATCTCTTAA AAAGAAAAAT AACTTGGTTT    1620
AGTGTGCTTA ATTTTACCAG GCAGTGAGGA AATTATATAT CACCTTGACT GTCCTGCAGT    1680
GTTGCCCAGT CAATAAAATG CACAAATAAT CTTTTTCATA ATACATGGCC AACTTTATCC    1740
TATCACTTGA ATATGTCAGG ATAAACTGAT TGTGCAGTTG GTTGATAACA TTGTATTTTG    1800
GAATGGATTA TTTGAATTTG TTTTGCTACT TTATTATTTG ATATTCTTCT CCAGTGTTCA    1860
TCTTATGAAG TTATTGCAT CTGAATATGA AGAGTCTGTT TCAAAATAGT CTTCAAGTTT    1920
CCAACGCAGT GTCTCAAATG TAGGTCGTTC CTTAGGCTCT GCATTCCAGC ACTCCAACAT    1980
GATGTTGTAA AATTGCTGTG GACAGTTGGA TGGTTGCGGA AGTCTATAGT TTTGAGCCAA    2040
```

FIG. 5C

```
CATCTGGATT ACCTGGGCAC CTGTCATACC ACTGTAAGGC ATTTTGCCAT AAGTAATGAT   2100
TTCATAAAGA AGGATTCCAA ATGACCATAC ATCGGACTTA ATGCTGAATT TATTACTACG   2160
AATGGCTTCG GGGCAGTCC  ACTTCACCGG CAGCTTTATT TCGTGTCTAG ATTCATAGAT   2220
GTCTTCATTA TCTACCTTAA AAACTCTGGC AAGTCCAAAA TCTGCTACTT TGTAGATATT   2280
ATGTTCACCA ACGAGGACAT TTCTGGCAGC CAGATCTCTG TGAATGTAGT TCCGAGACTC   2340
CAGATAGGCC ATTCCAGAGG CAACCTGTGC CGCCATGTCT ACCTGTTGAG TCAGATGGAT   2400
TTTTGATCCA GTGTCATTTT TTGCAGACTT CCATGTCTCA TCAACTCTGT              2460
AATAATATAA ATTGGATCTT CTAAAGTGCA AACAGCATAA AGCTGGATAA GCTTTGGATG   2520
TCTTAGGTTC TTCATTATCT GTGCCTCCCT CAGGAAGTCA TTTGGATCCA TTGAACCTGG   2580
TTTTAATGTT TTCACTGCTA CTGGAGTGGT ATGTTCCAC  AGACCTTCCC ATACTTCGCC   2640
AAACTGACCA GATCCCAATC GCTTCAGAAG CTGTATGGAG TTGCGGGTCTA TCTCCCATTG  2700
GTCCACGGTT TTATACGACA AATCAAATGG AGCTGGGACC TGGATCTTTA AGCATGGTTT   2760
CCCCAGCTTG ACACACAGGC CGTCACTTGT CTTGGTGTAG TGGCTCACAA ATTCGTTCAG   2820
TGTTGAAAAG ATTCTTCTTC GCGTGAGAAG AAATCCCCCT TCATCCAGTC TTTTAATTCT   2880
GTAGTGTTTT ACAACTGCTC CATCTAAAAC TGAAAGAGAG AATTCTCCTT TTTGGCTTTC   2940
ACTTTCTCTG ATTAGAAAGG AACCGGTCTT GTTTTCTGAA TATAATAGTT GTTTCTCTGC   3000
ATCTGATCTT CCGATTGCTC CAAAGAACCA CGGCTCTGCC TGTAGGCTTC TGTCCTCAGC   3060
```

FIG. 5D

```
CACGTAGTTA GAAGGAATAT AGCCTTGTAG TTGCTGACTG AGCCATCTC GTCTTTTCTC   3120
CAAGTGTCTG GCAAACCACC AGCCCTCATG CAAAGTGTCC AGAACTTGAA GTTTGTCACC   3180
TGCTCGGAAG CTCAAGTCCT CAGCAGTCCG AGCCTGGTAA TCAAACAAAG CCACAAAGTA   3240
GTGGCCATGC CTCTGTGACT GGGAGAGCA AAGGGCCCCT GGATTTTCAA TCACGGTTGA   3300
CTTGTCTGCC TCCGTGGACA AACAGGGGAG ATAGGGTTCT AGTACTCCC AGAGCCTCTG   3360
ACAGATGTTG CTCATTGTGC CTTGGTGGGG AGAAGAGGAG CAGGGCTTCT CCCTCTCCCC   3420
TTAGTCTCTG CGATCCACCT TATCTTCCTT CACCAGGCAA CTTTGAAGTC AGCACCAACT   3480
CACCATACTT CGGAGAGTAT GCAAAGTCCC GTTTCAGATC AGTCCAGCAG CTGGGTTGCA   3540
GCAAGTCCTA CCTGGAGAGA CTTACCGGCT TGCTTTCTGT GGCTGGAGGT GCTACCCCGA   3600
GGCAAAACTG AGCAGGAGCT GGGCAGCTGC TCACTAGGAA AAATTAAAAG GGCTTTATTT   3660
GCTTAAGAAT CCCACAACAA AAATAAAATA AAATTAAAAG GGCTTTATTT AGACAAATAT   3720
CTGAGAACAG AATGGTGCCA TCTTGCCTTT TGTCCCAATA AAAAGTTAGC AAGAGGAAGC   3780
TACTAACCCC TGGTAAAACC TCCACGTCTT GCTTTCGCCA GGGTCGACTC GAGGGATCTT   3840
CCATACCTAC CAGTTCTGCG CCTGCAGGTC GCGGCCGCGA CTCTAGAGTC GACCTGCAGA   3900
AGCTTGGGCCG CCATGGCCCA ACTTGTTTAT TGCAGCTTAT AATGGTTACA AATAAAGCAA   3960
TAGCATCACA AATTTCACAA ATAAAGCATT TTTTTCACTG CATTCTAGTT GTGGTTTGTC   4020
CAAACTCATC AATGTATCTT ATCATGTCTG GATCGGGAAT TAATTCGGCG CAGCACCATG   4080
```

FIG. 5E

```
GCCTGAAATA ACCTCTGAAA GAGGAACTTG GTTAGGTACC TTCTGAGGCG GAAAGAACCA    4140
GCTGTGGAAT GTGTGTCAGT TAGGGTGTGG AAAGTCCCCA GGCTCCCCAG CAGGCAGAAG    4200
TATGCAAAGC ATGCATCTCA ATTAGTCAGC AACCAGGTGT GGAAAGTCCC CAGGCTCCCC    4260
AGCAGGCAGA AGTATGCAAA GCATGCATCT CAATTAGTCA GCAACCATAG TCCCGCCCCT    4320
AACTCCGCCC ATCCCGCCCC TAACTCCGCC CAGTTCCGCC CATTCTCCGC CCCATGGCTG    4380
ACTAATTTTT TTTATTTATG CAGAGGCCGA GGCCGCCTCG GCCTCTGAGC TATTCCAGAA    4440
GTAGTGAGGA GGCTTTTTTG GAGGCCTAGG CTTTTGCAAA AAGCTGTTAA CAGCTTGGCA    4500
CTGGCCGTCG TTTTACAACG TCGTGACTGG GAAAACCCTG GCGTTACCCA ACTTAATCGC    4560
CTTGCAGCAC ATCCCCCTTT CGCCAGCTGG CGTAATAGCG AAGAGGCCCG CACCGATCGC    4620
CCTTCCCAAC AGTTGCGCAG CCTGAATGGC GAATGGCGCC TGATGCGGTA TTTTCTCCTT    4680
ACGCATCTGT GCGGTATTTC ACACCGCATA CGTCAAAGCA ACCATAGTAC GCGCCCTGTA    4740
GCGGCGCATT AAGCGCGGCG GGTGTGGTGG TTACGCGCAG CGTGACCGCT ACACTTGCCA    4800
GCGCCCTAGC GCCCGCTCCT TTCGCTTTCT TCCCTTCCTT TCTCGCCACG TTCGCCGGCT    4860
TTCCCCGTCA AGCTCTAAAT CGGGGGCTCC CTTTAGGGTT CCGATTTAGT GCTTTACGGC    4920
ACCTCGACCC CAAAAAACTT GATTTGGGTG ATGGTTCACG TAGTGGGCCA TCGCCCTGAT    4980
AGACGGTTTT TCGCCCTTTG ACGTTGGAGT CCACGTTCTT TAATAGTGGA CTCTTGTTCC    5040
AAACTGGAAC AACACTCAAC CCTATCTCGG GCTATTCTTT TGATTTATAA GGGATTTTGC    5100
```

FIG. 5F

```
CGATTTCGGC CTATTGGTTA AAAATGAGC TGATTTAACA AAAATTTAAC GCGAATTTTA    5160
ACAAATATT  AACGTTACA  ATTTATGT  GCACTCTCAG TACAATCTGC TCTGATGCCG    5220
CATAGTTAAG CCAGCCCCGA CACCCGCCAA CACCCGCTGA CGGCCCCTGA CGGGCTTGTC   5280
TGCTCCCGGC ATCCGCTTAC AGACAAGCTG TGACCGTCTC CGGGAGCTGC ATGTGTCAGA   5340
GGTTTTCACC GTCATCACCG AAACGCGCGA GACGAAAGGG CCTCGTGATA CGCCTATTTT   5400
TATAGGTTAA TGTCATGATA ATATGGTTT  CTTAGACGTC AGTGGCACT  TTTCGGGAA    5460
ATGTGCGCGG AACCCCTATT TGTTTATTTT TCTAAATACA TTCAAATATG TATCCGCTCA   5520
TGAGACAATA ACCCTGATAA ATGCTTCAAT AATATTGAAA AGGAAGAGT  ATGAGTATTC   5580
AACATTCCG  TGTCGCCCTT ATTCCCTTTT TTGCGGCATT TTGCCTTCCT GTTTTTGCTC   5640
ACCCAGAAAC GCTGGTGAAA GTAAAAGATG CTGAAGATCA GTTGGGTGCA CGAGTGGGTT   5700
ACATCGAACT GGATCTCAAC AGCGGTAAGA TCCTTGAGAG TTTTCGCCCC GAAGAACGTT   5760
TTCCAATGAT GAGCACTTTT AAAGTTCTGC TATGTGGCGC GGTATTATCC CGTATTGACG   5820
CCGGGCAAGA GCAACTCGGT CGCCGCATAC ACTATTCTCA GAATGACTTG GTTGAGTACT   5880
CACCAGTCAC AGAAAAGCAT CTTACGGATG GCATGACAGT AAGAGAATTA TGCAGTGCTG   5940
CCATAACCAT GAGTGATAAC ACTGCGGCCA ACTTACTTCT GACAACGATC GGAGGACCGA   6000
AGGAGCTAAC CGCTTTTTG  CACAACATGG GGGATCATGT AACTCGCCTT GATCGTTGGG   6060
AACCGGAGCT GAATGAAGCC ATACCAAACG ACGAGCGTGA CACCACGATG CCTGTAGCAA   6120
```

FIG. 5G

| | | | | | |
|---|---|---|---|---|---|
| TGGCAACAAC | GTTGCGCAAA | CTATTAACTG | GCGAACTACT | TACTCTAGCT | TCCCGGCAAC | 6180
| AATTAATAGA | CTGGATGGAG | GCGGATAAAG | TTGCAGGACC | ACTTCTGCGC | TCGGCCCTTC | 6240
| CGGCTGGCTG | GTTTATTGCT | GATAAATCTG | GAGCCGGTGA | GCGTGGGTCT | CGCGGTATCA | 6300
| TTGCAGCACT | GGGGCCAGAT | GGTAAGCCCT | CCCGTATCGT | AGTTATCTAC | ACGACGGGGA | 6360
| GTCAGGCAAC | TATGGATGAA | CGAAATAGAC | AGATCGCTGA | GATAGGTGCC | TCACTGATTA | 6420
| AGCATTGGTA | ACTGTCAGAC | CAAGTTTACT | CATATATACT | TTAGATTGAT | TTAAAACTTC | 6480
| ATTTTTAATT | TAAAAGGATC | TAGGTGAAGA | TCCTTTTTGA | TAATCTCATG | ACCAAAATCC | 6540
| CTTAACGTGA | GTTTTCGTTC | CACTGAGCGT | CAGACCCCGT | AGAAAAGATC | AAAGGATCTT | 6600
| CTTGAGATCC | TTTTTTTCTG | CGCGTAATCT | GCTGCTTGCA | AACAAAAAAA | CCACCGCTAC | 6660
| CAGCGGTGGT | TTGTTTGCCG | GATCAAGAGC | TACCAACTCT | TTTTCCGAAG | GTAACTGGCT | 6720
| TCAGCAGAGC | GCAGATACCA | AATACTGTTC | TTCTAGTGTA | GCCGTAGTTA | GGCCACCACT | 6780
| TCAAGAACTC | TGTAGCACCG | CCTACATACC | TCGCTCTGCT | AATCCTGTTA | CCAGTGGCTG | 6840
| CTGCCAGTGG | CGATAAGTCG | TGTCTTACCG | GGTTGGACTC | AAGACGATAG | TTACCGGATA | 6900
| AGGCGCAGCG | GTCGGGCTGA | ACGGGGGGTT | CGTGCACACA | GCCCAGCTTG | GAGCGAACGA | 6960
| CCTACACCGA | ACTGAGATAC | CTACAGCGTG | AGCTATGAGA | AAGCGCCACG | CTTCCCGAAG | 7020
| GGAGAAAGGC | GGACAGGTAT | CCGGTAAGCG | GCAGGGTCGG | AACAGGAGAG | CGCACGAGGG | 7080
| AGCTTCCAGG | GGGAAACGCC | TGGTATCTTT | ATAGTCCTGT | CGGGTTTCGC | CACCTCTGAC | 7140

FIG. 5H

```
TTGAGCGTCG ATTTTGTGA TGCTCGTCAG GGGGGCGGAG CCTATGGAAA AACGCCAGCA    7200
ACGGGCCCTT TTTACGGTTC CTGGCCTTTT GCTGGCCTTT TGCTCACATG TTCTTTCCTG    7260
CGTTATCCCC TGATTCTGTG GATAACCGTA TTACCGCCTT TGAGTGAGCT GATACCGCTC    7320
GCCGCAGCCG AACGACCCGA CGCAGCGAGT CAGTGAGCGA GGAAGCGGAA GAGCGCCCAA    7380
TACGCAAACC GCCTCTCCCC GCGCGTTGGC CGATTCATTA ATGCAGCTGG CACGACAGGT    7440
TTCCCGACTG GAAAGCGGGC AGTGAGCGCA ACGCAATTAA TGTGAGTTAG CTCACTCATT    7500
AGGCACCCCA GGCTTTACAC TTTATGCTTC CGGCTCGTAT GTTGTGTGGA ATTGTGAGCG    7560
GATAACAATT TCACACAGGA AACAGCTATG ACATGATTAC GAATTAA                  7607
```

FIG. 5I

```
Met Ser Asn Ile Cys Gln Arg Leu Trp Glu Tyr Leu Glu Pro Tyr Leu
  1               5                  10                  15
Pro Cys Leu Ser Thr Glu Ala Asp Lys Ser Thr Val Ile Glu Asn Pro
                 20                  25                  30
Gly Ala Leu Cys Ser Pro Gln Ser Gln Arg His Gly His Tyr Phe Val
                 35                  40                  45
Ala Leu Phe Asp Tyr Gln Ala Arg Thr Ala Glu Asp Leu Ser Phe Arg
                 50                  55                  60
Ala Gly Asp Lys Leu Gln Val Leu Asp Thr Leu His Glu Gly Trp Trp
 65              70                  75                  80
Phe Ala Arg His Leu Glu Lys Arg Arg Asp Gly Ser Ser Gln Gln Leu
                 85                  90                  95
Gln Gly Tyr Ile Pro Ser Asn Tyr Val Ala Glu Asp Arg Ser Leu Gln
                100                 105                 110
Ala Glu Pro Trp Phe Phe Gly Ala Ile Gly Arg Ser Asp Ala Glu Lys
                115                 120                 125
Gln Leu Leu Tyr Ser Glu Asn Lys Thr Gly Ser Phe Leu Ile Arg Glu
130                 135                 140
Ser Glu Ser Gln Lys Gly Glu Phe Ser Leu Ser Val Leu Asp Gly Ala
145                 150                 155                 160
Val Val Lys His Tyr Arg Ile Lys Arg Leu Asp Glu Gly Gly Phe Phe
                165                 170                 175
Leu Thr Arg Arg Ile Phe Ser Thr Leu Asn Glu Phe Val Ser His
                180                 185                 190
```

FIG. 5J

Tyr Thr Lys Thr Ser Asp Gly Leu Cys Val Lys Leu Gly Lys Pro Cys
195                         200                 205

Leu Lys Ile Gln Val Pro Ala Pro Phe Asp Leu Ser Tyr Lys Thr Val
210                         215                 220

Asp Gln Trp Glu Ile Asp Arg Asn Ser Ile Gln Leu Leu Lys Arg Leu
225                         230                 235                 240

Gly Ser Gly Gln Phe Gly Glu Val Trp Glu Gly Leu Trp Asn Asn Thr
245                         250                 255

Thr Pro Val Ala Val Lys Thr Leu Lys Pro Gly Ser Met Asp Pro Asn
260                         265                 270

Asp Phe Leu Arg Glu Ala Gln Ile Met Lys Asn Leu Arg His Pro Lys
275                         280                 285

Leu Ile Gln Leu Tyr Ala Val Cys Thr Leu Glu Asp Pro Ile Tyr Ile
290                         295                 300

Ile Thr Glu Leu Met Arg His Gly Ser Leu Gln Glu Tyr Leu Gln Asn
305                         310                 315                 320

Asp Thr Gly Ser Lys Ile His Leu Thr Gln Gln Val Asp Met Ala Ala
325                         330                 335

Gln Val Ala Ser Gly Met Ala Tyr Leu Glu Ser Arg Asn Tyr Ile His
340                         345                 350

Arg Asp Leu Ala Ala Arg Asn Val Leu Val Gly Glu His Asn Ile Tyr
355                         360                 365

Lys Val Ala Asp Phe Gly Leu Ala Arg Val Phe Lys Val Asp Asn Glu
370                         375                 380

FIG. 5K

Asp Ile Tyr Glu Ser Arg His Glu Ile Lys Leu Pro Val Lys Trp Thr
385                390                395                400

Ala Pro Glu Ala Ile Arg Ser Asn Lys Phe Ser Ile Lys Ser Asp Val
        405                410                415

Trp Ser Phe Gly Ile Leu Leu Tyr Glu Ile Ile Thr Tyr Gly Lys Met
        420                425                430

Pro Tyr Ser Gly Met Thr Gly Ala Gln Val Ile Gln Met Leu Ala Gln
        435                440                445

Asn Tyr Arg Leu Pro Gln Pro Ser Asn Cys Pro Gln Gln Phe Tyr Asn
        450                455                460

Ile Met Leu Glu Cys Trp Asn Ala Glu Pro Lys Glu Arg Pro Thr Phe
465                470                475                480

Glu Thr Leu Arg Trp Lys Leu Glu Asp Tyr Phe Glu Thr Asp Ser Ser
        485                490                495

Tyr Ser Asp Ala Asn Asn Phe Ile Arg *
500                505

FIG. 6

```
GCGGCCGCAG AGAAAGCAGA GGATGGGGCT TAGCAGCTGG CAGAGCCAGG AGCGGGGAGG    60
TAGCAGAAAG ACCACAAGTA CAAAGAAGTC CTGAAACTTT GGTTTTGCTG CTGCAGCCCA   120
TTGAGAGTGA CGACATGGAG CACAAGACCC TGAAGATCAC CGACTTTGGC CTGGCCCGAG   180
AGTGGCACAA AACCACACAA ATGAGTGCCG CNGGCACCTA CNCCTGGATG GCTCCTGAGG   240
TTATCAAGGC CTCCACCTTC TCTAAGGGCA GTGACGTCTG GAGTTTTGGG GTGCTGCTGT   300
GGGAACTGCT GACCGGGGAG NTGCCATACC GTGGCATTGA CTGCCTTGCT GTGGCCTATG   360
GCGTAGCTGT TAACAAGCTC ACACTGCCAT CCATCCACCT GGCC                    404
```

FIG. 7A

```
ATGAGAGCGT TGGCGCGCGA CGGCGGCCCAG CTGCCGCTGC TCGTTGTTTT TTCTGCAATG    60
ATATTTGGGA CTATTACAAA TCAAGATCTG CCTGTGATCA AGTGTGTTTT AATCAATCAT   120
AAGAACAATG ATTCATCAGT GGGGAAGTCA TCATCATATC CCATGGTATC AGAATCCCCG   180
GAAGACCTCG GGTGTGCGTT GAGACCCCAG AGCTCAGGGA CAGTGTACGA AGCTGCCGCT   240
GTGGAAGTGG ATGTATCTGC TTCCATCACA CTGCAAGTGC TGGTCGATGC CCCAGGGAAC   300
ATTCCCTGTC TCTGGGTCTT TAAGCACAGC TCCCTGAATT GCCAGCCACA TTTTGATTTA   360
CAAAACAGAG GAGTTGTTTC CATCGTCATT TTGAAAATGA CAGAAACCCA AGCTGGAGAA   420
TACCTACTTT TTATTCAGAG TGAAGCTACC AATTACACAA TATTGTTTAC AGTGAGTATA   480
AGAAATACCC TGCTTTACAC ATTAAGAAGA CCTTACTTTA GAAAAATGGA AAACCAGGAC   540
GCCCTGGTCT GCATATCTGA GAGCGTTCCA CCAGCTGTTG GCTTTGCCAT GCTTTGCGAT   600
TCACAGGGGG AAAGCTGTAA AGAAGAAAGT CCAGCTGTTG TTAAAAAGGA GGAAAAAGTG   660
CTTCATGAAT TATTGGGAC GGACATAAGG TGCTGTGCCA GAAATGAACT GGGCAGGGAA   720
TGCACCAGGC TGTTCACAAT AGATCTAAAT CAAACTCCTC AGACCACATT GCCACAATTA   780
TTTCTTAAAG TAGGGGAACC CTTATGGATA AGGTGCAAAG CTGTTCATGT GAACCATGGA   840
TTCGGGCTCA CCTGGGAATT AGAAAACAAA GCACTCGAGG AGGGCAACTA CTTTGAGATG   900
AGTACCTATT CAACAAACAG AACTATGATA CGGATTCTGT TTGCTTTTGT ATCATCAGTG   960
GCAAGAAACG ACACCGGATA CTACACTTGT TCCTCTTCAA AGCATCCCAG TCAATCAGCT  1020
TTGGTTACCA TCGTAGAAAA GGGATTTATA AATGCTACCA ATTCAAGTGA AGATTATGAA  1080
```

FIG. 7B

```
ATTGACCAAT ATGAAGAGTT TTGTTTTCT GTCAGGTTTA AAGCCTACCC ACAAATCAGA    1140
TGTACGTGGA CCTTCTCTCG AAAATCATTT CCTTGTGAGC AAAAGGGTCT TGATAACGGA    1200
TACAGCATAT CCAAGTTTTG CAATCATAAG CACCAGCCAG GAGAATATAT ATTCCATGCA    1260
GAAAATGATG ATGCCCAATT TACCAAAATG TTCACGCTGT ATATAAGAAG GAAACCTCAA    1320
GTCCTCGCAG AAGCTTCGGC AAGTCAGGCG TCCTGTTTCT CGGATGGATA CCCATTACCA    1380
TCTTGGACCT GGAAGAAGTG TTCAGACAAG TCTCCCAACT GCACAGAAGA GATCACAGAA    1440
GGAGTCTGGA ATAGAAAGGC TAACAGAAAA GTGTTTGGAC AGTGGGTGTC GAGCAGTACT    1500
CTAAACATGA GTGAAGCCAT AAAAGGGTTC CTGGTCAAGT GCTGTGCATA CAATTCCCTT    1560
GGCACATCTT GTGAGACGAT CCTTTTAAAC TCTCCAGGCC CCTTCCCTTT CATCCAAGAC    1620
AACATCTCAT TCTATGCAAC AATTGGTGTT TGTCTCCTCT TCATTGTCGT TTTAACCCTG    1680
CTAATTTGTC ACAAGTACAA AAAGCAATTT AGTATGAAA GCCAGCTACA GATGGTACAG     1740
GTGACCGGAT CCTCAGATTA TGAGTACTTC TACGTTGATT TCAGAGAATA TGAATATGAT    1800
GTCAAATGGG AGTTTCCAAG AGAAAATTTA GAGTTTGGGA AGGTACTAGG ATCAGGTGCT    1860
TTTGGAAAAG TGATGAACGC AACAGCTTAT GGAATTAGCA AAACAGGAGT CTCAATCCAG    1920
GTTACCGTCA AAATGCTGAA AGAAAAAGCA GACAGCTCTG AAAGAGAGGC ACTCATGTCA    1980
GAACTCAAGA TGATGACCCA GCTGGGAAGC CACGAGAATA TTGTGAACCT GCTGGGGGCG    2040
TGCACACTGT CAGGACCAAT TTACTTGATT TTTGAATACT GTTGCTATGG TGATCTTCTC    2100
AACTATCTAA GAAGTAAAAG AGAAAAATTT CACAGGACTT GGACAGAGAT TTTCAAGGAA    2160
```

FIG. 7C

```
CACAATTTCA GTTTTTACCC CACTTTCCAA TCACATCCAA ATTCCAGCAT GCCTGGTTCA  2220
AGAGAAGTTC AGATACACCC GGACTCGGAT CAAATCTCAG GGCTTCATGG GAATTCATTT  2280
CACTCTGAAG ATGAAATTGA ATATGAAAAC CAAAAAAGGC TGGAAGAAGA GGAGGACTTG  2340
AATGTGCTTA CATTTGAAGA TCTTCTTTGC TTTGCATATC AAGTTGCCAA AGGAATGGAA  2400
TTTCTGGAAT TTAAGTCGTG TGTTCACAGA GACCTGGCCG CCAGGAACGT GCTTGTCACC  2460
CACGGGAAAG TGGTGAAGAT ATGTGACTTT GGATTGGCTC GAGATATCAT GAGTGATTCC  2520
AACTATGTTG TCAGGGGCAA TGCCCCGTCTG CCTGTAAAAT GGATGGCCCCC CGAAAGCCTG  2580
TTTGAAGGCA TCTACACCAT TAAGAGTGAT GTCTGGTCAT ATGGAATATT ACTGTGGGAA  2640
ATCTTCTCAC TTGGTGTGAA TCCTTACCCT GGCATTCCGG TTGATGCTAA CTTCTACAAA  2700
CTGATTCAAA ATGGATTTAA AATGGATCAG CCATTTTATG CTACAGAAGA AATATACATT  2760
ATAATGCAAT CCTGCTGGGC TTTTGACTCA AGGAAACGGC CATCCTTCCC TAATTTGACT  2820
TCGTTTTTAG GATGTCAGCT GGCAGATGCA GAAGAAGCGA TGTATCAGAA TGTGGATGGC  2880
CGTGTTTCGG AATGTCCTCA CACCTACCAA AACAGGCGAC CTTTCAGCAG AGAGATGGAT  2940
TTGGGCTAC TCTCTCCGCA GGCTCAGGTC GAAGATTCGT AGAGGAACAA TTTAGTTTTA  3000
AGGACTTCAT CCCTCCACCT ATCCCTAACA GGCTGTAGAT TACCAAAACA AGGTAATTT   3060
CATCACTAAA AGAAAATCTA TTATCAACTG CTGCTTCACC AGACTTTTCT CTAGAGAGCG  3120
```

FIG. 8A

```
TCGGGTCCA CCCGCCCAGG GAGAGTCAGA CCTGGGGGGG CGAGGGCCCC CCAAACTCAG                    60

TTCGGATCCT ACCCGAGTGA GGCGGCGCC ATG GAG CTC CGG GTG CTG CTC TGC                    113
                                Met Glu Leu Arg Val Leu Leu Cys
                                 1                           5

TGG GCT TCG TTG GCC GCA GCT TTG GAA GAG ACC CTG AAC ACA AAA                         161
Trp Ala Ser Leu Ala Ala Ala Leu Glu Glu Thr Leu Asn Thr Lys
         10                  15                  20

TTG GAA ACT GCT GAT CTG AAG TGG GTG ACA TTC CCT CAG GTG GAC GGG                     209
Leu Glu Thr Ala Asp Leu Lys Trp Val Thr Phe Pro Gln Val Asp Gly
 25                  30                  35                  40

CAG TGG GAG GAA CTG AGC GGC CTG GAT GAG GAA CAG CAG CAC AGC GTG CGC                 257
Gln Trp Glu Glu Leu Ser Gly Leu Asp Glu Glu Gln Gln His Ser Val Arg
                 45                  50                  55

ACC TAC GAA GTG TGT GAC GTG CAG CGT GCC CCG GGC CAG GCC CAC TGG                     305
Thr Tyr Glu Val Cys Asp Val Gln Arg Ala Pro Gly Gln Ala His Trp
                     60                  65                  70

CTT CGC ACA GGT TGG GTC CCA CGG CGG GCC GTC CAC GTG TAC GCC                         353
Leu Arg Thr Gly Trp Val Pro Arg Arg Ala Val His Val Tyr Ala
                 75                  80                  85

ACG CTG CGC TTC ACC ATG CTC GAG TGC CTG TCC CTG CCT CGG GCT GGG                     401
Thr Leu Arg Phe Thr Met Leu Glu Cys Leu Ser Leu Pro Arg Ala Gly
                     90                  95                 100

CGC TCC TGC AAG GAG ACC TTC ACC GTC TTC TAC TAT GAG AGC GAT GCG                     449
Arg Ser Cys Lys Glu Thr Phe Thr Val Phe Tyr Tyr Glu Ser Asp Ala
105                 110                 115                 120

GAC ACG GCC ACG GCC CTC ACG CCA TGG ATG GAG AAC CCC TAC ATC                         497
Asp Thr Ala Thr Ala Leu Thr Pro Ala Trp Met Glu Asn Pro Tyr Ile
                125                 130                 135
```

FIG. 8B

```
AAG GTG GAC ACG GTG GCC GCG GAG CAT CTC ACC CGG AAG CGC CCT GGG    545
Lys Val Asp Thr Val Ala Ala Glu His Leu Thr Arg Lys Arg Pro Gly
            140                 145                 150

GCC GAG GCC ACC GGG AAG GTG AAT GTC AAG ACG CTG CGT CTG GGA CCG    593
Ala Glu Ala Thr Gly Lys Val Asn Val Lys Thr Leu Arg Leu Gly Pro
        155                 160                 165

CTC AGC AAG GCT GGC TTC TAC CTG GCC TTC CAG GAC CAG GGT GCC TGC    641
Leu Ser Lys Ala Gly Phe Tyr Leu Ala Phe Gln Asp Gln Gly Ala Cys
    170                 175                 180

ATG GCC CTG CTA TCC CAC CTC TTC TAC AAA AAG TGC GCC CAG CTG        689
Met Ala Leu Leu Ser His Leu Phe Tyr Lys Lys Cys Ala Gln Leu
185                 190                 195                 200

ACT GTG AAC CTG ACT CGA TTC CCG GAG ACT GTG CCT CGG GAG CTG GTT    737
Thr Val Asn Leu Thr Arg Phe Pro Glu Thr Val Pro Arg Glu Leu Val
            205                 210                 215

GTG CCC GTG GCC GGT AGC TGC GTG GTG GAT GCC GTC CCC GCC CCT GGC    785
Val Pro Val Ala Gly Ser Cys Val Val Asp Ala Val Pro Ala Pro Gly
        220                 225                 230

CCC AGC CCC AGC CTC TAC TGC AGC GAT GAT GGC CAG TGG GCC GAA CAG    833
Pro Ser Pro Ser Leu Tyr Cys Ser Asp Asp Gly Gln Trp Ala Glu Gln
    235                 240                 245

CCG GTC ACG GGC TGC AGC TGT GCT CCG GGG TTC GAG GCA GCT GAG GGG    881
Pro Val Thr Gly Cys Ser Cys Ala Pro Gly Phe Glu Ala Ala Glu Gly
250                 255                 260

AAC ACC AAG TGC CGA GCC CAG GGC ACC TTC AAG CCC CTG TCA            929
Asn Thr Lys Cys Arg Ala Gln Gly Thr Phe Lys Pro Leu Ser
            265                 270                 275                 280
```

FIG. 8C

```
GGA GAA GGG TCC TGC CAG CCA TGC AAT AGC CAC TCT AAC ACC                     977
Gly Glu Gly Ser Cys Gln Pro Cys Asn Ser His Ser Asn Thr
                285                                 295

ATT GGA TCA GCC GTC TGC CAG TGC CGC GTC GGG TAC TTC CGG GCA CGC            1025
Ile Gly Ser Ala Val Cys Gln Cys Arg Val Gly Tyr Phe Arg Ala Arg
            300                             305                310

ACA GAC CCC CGG GGT GCA CCC TGC ACC ACC CCT CCT TCG GCT CCG CGG            1073
Thr Asp Pro Arg Gly Ala Pro Cys Thr Thr Pro Pro Ser Ala Pro Arg
        315                             320              325

AGC GTG GTT TCC CGC CTG AAC GGC TCC TCC CTG CAC CTG GAA TGG AGT            1121
Ser Val Val Ser Arg Leu Asn Gly Ser Ser Leu His Leu Glu Trp Ser
    330                             335                340

GCC CCC CTG GAG TCT GGT GGC CGA GAG GAC CTC ACC TAC GCC CTC CGC            1169
Ala Pro Leu Glu Ser Gly Gly Arg Glu Asp Leu Thr Tyr Ala Leu Arg
345                             350                355              360

TGC CGG GAG TGC CGA CCC GGA GGC TCC TGT GCG CCC TGC GGG GGA GAC            1217
Cys Arg Glu Cys Arg Pro Gly Gly Ser Cys Ala Pro Cys Gly Gly Asp
            365                             370                375

CTG ACT TTT GAC CCC GGC GAC CTG GTG GAG CCC TGG CCC GTG GTG               1265
Leu Thr Phe Asp Pro Gly Asp Leu Val Glu Pro Trp Val Val
        380                             385                390

GTT CGA GGG CTA CGT CCT GAC TTC ACC TAT ACC TTT GAG GTC ACT GCA            1313
Val Arg Gly Leu Arg Pro Asp Phe Thr Tyr Thr Phe Glu Val Thr Ala
    395                             400                405

TTG AAC GGG GTA TCC TCC TTA GCC ACG GGG CCC GTC CCA TTT GAG CCT            1361
Leu Asn Gly Val Ser Ser Leu Ala Thr Gly Pro Val Pro Phe Glu Pro
410                             415                420
```

FIG. 8D

```
GTC AAT GTC ACC ACT GAC CGA GAG GTA CCT GCA GTG TCT GAC ATC    1409
Val Asn Val Thr Thr Asp Arg Glu Val Pro Ala Val Ser Asp Ile
425                 430                 435                 440

CGG GTG ACG CGG TCC TCA CCC AGC AGC TTG AGC CTG GCC TGG GCT GTT    1457
Arg Val Thr Arg Ser Ser Pro Ser Ser Leu Ser Leu Ala Trp Ala Val
            445                 450                 455

CCC CGG GCA CCC AGT GGG GCT GTG CTG GAC TAC GAG GTC AAA TAC CAT    1505
Pro Arg Ala Pro Ser Gly Ala Val Leu Asp Tyr Glu Val Lys Tyr His
    460                 465                 470

GAG AAG GGC GCC GAG GGT CCC AGC AGC GTG CGG TTC CTG AAG ACG TCA    1553
Glu Lys Gly Ala Glu Gly Pro Ser Ser Val Arg Phe Leu Lys Thr Ser
475                 480                 485

GAA AAC CGG GCA GAG CTG CGG AAG CGG GGA GCC AGC TAC CTG    1601
Glu Asn Arg Ala Glu Leu Arg Lys Arg Gly Ala Ser Tyr Leu
        490                 495                 500

GTG CAG GTA CGG GCG TCT GAG GCC GGC TAC GGG CCC TTC GGC CAG    1649
Val Gln Val Arg Ala Ser Glu Ala Gly Tyr Gly Pro Phe Gly Gln
505                 510                 515                 520

GAA CAT CAC AGC CAG ACC CAA CTG GAT GAG AGC GAG GGC TGG CGG GAG    1697
Glu His His Ser Gln Thr Gln Leu Asp Glu Ser Glu Gly Trp Arg Glu
            525                 530                 535

CAG CTG GCC CTG ATT GCG GGG ACG GCA GTC GTG GGT GTG GTC CTG GTC    1745
Gln Leu Ala Leu Ile Ala Gly Thr Ala Val Val Gly Val Val Leu Val
    540                 545                 550

CTG GTC GTC ATT GTG GTC GCA GTT CTC TGC CTC AGG AAG CAG AGC AAT    1793
Leu Val Val Ile Val Val Ala Val Leu Cys Leu Arg Lys Gln Ser Asn
555                 560                 565
```

FIG. 8E

```
GGG AGA GAA GCA GAA TAT TCG GAC AAA CAC GGA CAG TAT CTC ATC GGA   1841
Gly Arg Glu Ala Glu Tyr Ser Asp Lys His Gly Gln Tyr Leu Ile Gly
570                     575                 580

CAT GGT ACT AAG GTC TAC ATC GAC CCC TTC ACT TAT GAA GAC CCT AAT   1889
His Gly Thr Lys Val Tyr Ile Asp Pro Phe Thr Tyr Glu Asp Pro Asn
585                     590                 595             600

GAG GCT GTG AGG GAA TTT GCA AAA GAG ATC GAT GTC TCC TAC GTC AAG   1937
Glu Ala Val Arg Glu Phe Ala Lys Glu Ile Asp Val Ser Tyr Val Lys
        605                 610                 615

ATT GAA GAG GTG ATT GGT GCA GGT GAG TTT GGC GAG GTG TGC CGG GGG   1985
Ile Glu Glu Val Ile Gly Ala Gly Glu Phe Gly Glu Val Cys Arg Gly
        620                 625                 630

CGG CTC AAG GCC CCA GGG AAG AAG AGC TGT GTG GCA ATC AAG ACC       2033
Arg Leu Lys Ala Pro Gly Lys Lys Ser Cys Val Ala Ile Lys Thr
635                 640                 645

CTG AAG GGT GGC TAC ACG GAG CGG CAG CGT GAG TTT CTG AGC GAG       2081
Leu Lys Gly Gly Tyr Thr Glu Arg Gln Arg Glu Phe Leu Ser Glu
650                 655                 660

GCC TCC ATC ATG GGC CAG TTC GAG CAC CCC AAT ATC ATC CGC CTG GAG   2129
Ala Ser Ile Met Gly Gln Phe Glu His Pro Asn Ile Ile Arg Leu Glu
665                 670                 675                 680

GGC GTG GTC ACC AAC AGC ATG CCC GTC ATG CCC GTC ATG CCC GTC ATG   2177
Gly Val Val Thr Asn Ser Met Pro Val Met Ile Leu Thr Glu Phe Met
685                 690                 695

GAG AAC GGC GCC CTG GAC TCC TTC CTG CGG CTA AAC GAC GGA CAG TTC   2225
Glu Asn Gly Ala Leu Asp Ser Phe Leu Arg Leu Asn Asp Gly Gln Phe
700                 705                 710
```

FIG. 8F

```
ACA GTC ATC CAG CTC GTG GGC ATG CTG CGG GGC ATC GCC TCG GGC ATG     2273
Thr Val Ile Gln Leu Val Gly Met Leu Arg Gly Ile Ala Ser Gly Met
             715                 720                 725

CGG TAC CTT GCC GAG ATG AGC TAC GTC CAC CGA GAC CTG GCT GCT CGC     2321
Arg Tyr Leu Ala Glu Met Ser Tyr Val His Arg Asp Leu Ala Ala Arg
         730                 735                 740

AAC ATC CTA GTC AAC AGC AAC CTC GTC TGC AAA GTG TCT GAC TTT GGC     2369
Asn Ile Leu Val Asn Ser Asn Leu Val Cys Lys Val Ser Asp Phe Gly
745                 750                 755                 760

CTT TCC CGA TTC CTG GAG GAG AAC TCT TCC GAT CCC ACC TAC ACG AGC     2417
Leu Ser Arg Phe Leu Glu Glu Asn Ser Ser Asp Pro Thr Tyr Thr Ser
             765                 770                 775

TCC CTG GGA GGA AAG ATT CCC ATC CGA TGG ACT GCC CCG GAG GCC ATT     2465
Ser Leu Gly Gly Lys Ile Pro Ile Arg Trp Thr Ala Pro Glu Ala Ile
         780                 785                 790

GCC TTC CGG AAG TTC ACT TCC GCC AGT GAT GCC TGG AGT TAC GGG ATT     2513
Ala Phe Arg Lys Phe Thr Ser Ala Ser Asp Ala Trp Ser Tyr Gly Ile
     795                 800                 805

GTG ATG TGG GAG GTG ATG TCA TTT GGG GAG AGG CCG TAC TGG GAC ATG     2561
Val Met Trp Glu Val Met Ser Phe Gly Glu Arg Pro Tyr Trp Asp Met
810                 815                 820

AGC AAT CAG GAC GTG ATC AAT GCC ATT GAA CAG GAC TAC CGG CTG CCC     2609
Ser Asn Gln Asp Val Ile Asn Ala Ile Glu Gln Asp Tyr Arg Leu Pro
825                 830                 835                 840

CCG CCC CCA GAC TGT CCC ACC TCC CTC CAC CAG CTC ATG CTG GAC TGT     2657
Pro Pro Pro Asp Cys Pro Thr Ser Leu His Gln Leu Met Leu Asp Cys
         845                 850                 855
```

FIG. 8G

```
TGG CAG AAA GAC CGG AAT GCC CGG TTC CCC CAG GTG GTC AGC    2705
Trp Gln Lys Asp Arg Asn Ala Arg Phe Pro Gln Val Val Ser
                860                 865                 870

GCC CTG GAC AAG ATG ATC CGG AAC CCC GCC AGC CTC AAA ATC GTG GCC    2753
Ala Leu Asp Lys Met Ile Arg Asn Pro Ala Ser Leu Lys Ile Val Ala
            875                 880                 885

CGG GAG AAT GGC GGG GCC TCA CAC CCT CTC CTG GAC CAG CGG CAG CCT    2801
Arg Glu Asn Gly Gly Ala Ser His Pro Leu Leu Asp Gln Arg Gln Pro
        890                 895                 900

CAC TAC TCA GCT TTT GGC TCT GTG GGC GAG TGG CTT CGG GCC ATC AAA    2849
His Tyr Ser Ala Phe Gly Ser Val Gly Glu Trp Leu Arg Ala Ile Lys
    905                 910                 915                 920

ATG GGA AGA TAC GAA GAA AGT TTC GCA GCC GCT GGC TTT GGC TCC TTC    2897
Met Gly Arg Tyr Glu Glu Ser Phe Ala Ala Gly Phe Gly Ser Phe
            925                 930                 935

GAG CTG GTC AGC CAG ATC TCT GCT GAG GAC CTG CTC CGA ATC GGA GTC    2945
Glu Leu Val Ser Gln Ile Ser Ala Glu Asp Leu Leu Arg Ile Gly Val
        940                 945                 950

ACT CTG GCG GGA CAC CAG AAG AAA ATC TTG GCC AGT GTC CAG CAC ATG    2993
Thr Leu Ala Gly His Gln Lys Lys Ile Leu Ala Ser Val Gln His Met
    955                 960                 965

AAG TCC CAG GCC AAG GCC ACC CCG GGT GGG ACA GGA GGA CCG GCC    3041
Lys Ser Gln Ala Lys Pro Gly Thr Pro Gly Gly Thr Gly Gly Pro Ala
        970                 975                 980

CCG CAG TAC TGA CCT GCA GGA ACT CCC CAC CCC AGG GAC ACC GCC TCC    3089
Pro Gln Tyr *     Pro Ala Gly Thr Pro His Pro Arg Asp Thr Ala Ser
    985                 990                 995                 1000
```

FIG. 8H

```
CCA TTT TCC GGG GCA GAG TGG GGA CTC ACA GAG GCC CCC AGC CCT GTG      3137
Pro Phe Ser Gly Ala Glu Trp Gly Leu Thr Glu Ala Pro Ser Pro Val
                        1005                         1010                         1015

CCC CGC TGG ATT GCA CTT TGA GCC CGT GGG GTG AGG AGT TGG CAA TTT      3185
Pro Arg Trp Ile Ala Leu  *  Ala Arg Gly Val Arg Ser Trp Gln Phe
                        1020                         1025                         1030

GGA GAG ACA GGA TTT GGG GGT TCT GCC ATA ATA GGA GGG GAA AAT CAC      3233
Gly Glu Thr Gly Phe Gly Gly Ser Ala Ile Ile Gly Gly Glu Asn His
                        1035                         1040                         1045

CCC CCA GCC ACC TCG GGG AAC TCC AGA CCA AGG GTG AGG GCG CCT TTC      3281
Pro Pro Ala Thr Ser Gly Asn Ser Arg Pro Arg Val Arg Ala Pro Phe
                        1050                         1055                         1060

CCT CAG GAC TGG GTG TGA CCA GAG GAA AAG GTG CCC AAC ATC TCC          3329
Pro Gln Asp Trp Val  *  Pro Glu Glu Lys Val Pro Asn Ile Ser
                        1065                         1070                         1075                    1080

CAG CCT CCC CAG GTG CCC CCC TCA CCT TGA TGG GTG CGT TCC CGC AGA      3377
Gln Pro Pro Gln Val Pro Pro Ser Pro  *  Trp Val Arg Ser Arg Arg
                        1085                         1090                         1095

CCA AAG AGA GTG TGA CTC CCT TGC CAG CTC CAG AGT GGG GGG GCT GTC      3425
Pro Lys Arg Val  *  Leu Pro Cys Gln Leu Gln Ser Gly Gly Ala Val
                        1100                         1105                         1110

CCA GGG GGC AAG AAG GGG TGT CAG GGC CCA GTG ACA AAA TCA TTG GGG      3473
Pro Gly Gly Lys Lys Gly Cys Gln Gly Pro Val Thr Lys Ser Leu Gly
                        1115                         1120                         1125

TTT GTA GTC CCA ACT TGC TGC TGT CAC CAC CAA ACT CAA TCA TTT TTT      3521
Phe Val Val Pro Thr Cys Cys Cys His His Gln Thr Gln Ser Phe Phe
                        1130                         1135                         1140
```

FIG. 8I

```
TCC CTT GTA AAT GCC CCT CCC CCA GCT GCC TTC ATA TTG AAG GTT                    3569
Ser Leu Val Asn Ala Pro Pro Pro Ala Ala Phe Ile Leu Lys Val
1145                                    1150                    1155        1160

TTT GAG TTT TGT TTT TGG TCT TAA TTT TTC TCC CCG TTC CCT TTT TGT               3617
Phe Glu Phe Cys Phe Trp Ser  *  Phe Phe Ser Pro Phe Pro Phe Cys
          1165                      1170                            1175

TTC TTC GTT TTT TTC TAC CGT CCT TGT CAT AAC TTT GTG TTG GAG                    3665
Phe Phe Val Leu Phe Phe Tyr Arg Pro Cys His Asn Phe Val Leu Glu
     1180                           1185                       1190

GGA ACC TGT TTC ACT ATG GCC TCC TTT GCC CAA GTT GAA ACA GGG GCC               3713
Gly Thr Cys Phe Thr Met Ala Ser Phe Ala Gln Val Glu Thr Gly Ala
          1195                      1200                       1205

CAT CAT CAT GTC TGT TTC CAG AAC AGT GCC TTG GTC GTC ATC CCA CAT CCC           3761
His His His Val Cys Phe Gln Asn Ser Ala Leu Val Val Ile Pro His Pro
     1210                           1215                       1220

CGG ACC CCG CCT GGG ACC CCC AAG CTG TGT CCT ATG AAG GGG TGT GGG               3809
Arg Thr Pro Pro Gly Thr Pro Lys Leu Cys Pro Met Lys Gly Cys Gly
          1225                      1230                       1235        1240

GTG AGG TAG TGA AAA GGG CGG TAG TTG GTG GTG GAA CCC AGA AAC GGA               3857
Val Arg  *   *  Lys Gly Arg  *  Leu Val Val Glu Pro Arg Asn Gly
               1245                      1250                       1255

CGC CGG TGC TTG GAG GGG TTC TTA AAT TAT ATT TAA AAA AGT AAC TTT               3905
Arg Arg Cys Leu Glu Gly Phe Leu Asn Tyr Ile  *  Lys Ser Asn Phe
          1260                      1265                       1270

TTG TAT AAA TAA AAG AAA ATG GGA CGT GTC CCA GCT CCA GGG GTA                    3950
Leu Tyr Lys  *  Lys Lys Met Gly Arg Val Pro Ala Pro Gly Val
     1275                           1280                       1285

AAAAAAAAAA AAAAAAAAA                                                           3969
```

FIG. 9

```
Ala Arg Asn Ile Leu Val Asn Ser Asn Leu Val Cys Lys Val Ser Asp
 1               5                  10                  15
Phe Gly Leu Ser Arg Phe Leu Glu Asp Thr Ser Asp Pro Thr Tyr
                20                  25                  30
Thr Ser Ala Leu Gly Gly Lys Ile Pro Met Arg Trp Thr Ala Pro Glu
                35                  40                  45
Ala Ile Gln Tyr Arg Lys Phe Ala Ser Ala Ser
                50                  55
```

FIG. 10

```
Asn Val Leu Val Lys Ser Pro Asn His Val Lys Ile Thr Asp Phe Gly
 1               5                  10                  15
Leu Ala Arg Leu Leu Glu Gly Asp Glu Lys Glu Tyr Asn Ala Asp Gly
                20                  25                  30
Gly Lys Met Pro Ile Lys Trp Met Ala Leu Glu Cys Ile His Tyr Arg
                35                  40                  45
Lys Phe Thr His Gln Ser
                50
```

FIG. 11

```
Asn Cys Met Leu Ala Gly Asp Met Thr Val Cys Val Ala Asp Phe Gly
 1                   5                  10                  15
Leu Ser Trp Lys Ile Tyr Ser Gly Ala Thr Ile Val Arg Gly Cys Ala
                20                  25                  30
Ser Lys Leu Pro Val Lys Trp Leu Ala Leu Gly Ser Leu Ala Asp Asn
            35                  40                  45
Leu Tyr Thr Val His Ser
        50
```

FIG. 12

```
Asn Cys Leu Val Gly Lys Asn Tyr Thr Ile Lys Ile Ala Asp Phe Gly
 1                   5                  10                  15
Met Ser Arg Asn Leu Tyr Ser Gly Asp Tyr Tyr
                20                  25
```

FIG. 13

```
Thr Arg Asn Ile Leu Val Glu Asn Arg Val Lys Ile Gly Asp
1               5               10              15
Phe Gly Leu Thr Lys Val Leu Pro Gln Asp Lys Glu Tyr Tyr Lys Val
        20              25              30
Lys Glu Pro Gly Glu Ser Pro Ile Phe Trp Tyr Ala Pro Glu Ser Leu
        35              40              45
Thr Glu Ser Leu Phe Ser Val Ala Ser Asp
        50              55
```

FIG. 14

```
Ala Arg Asn Ile Leu Val Asn Ser Asn Leu Val Cys Lys Val Ser Asp
1               5               10              15
Phe Gly Met Ser Arg Val Leu Glu Asp Pro Glu Ala Ala Tyr Thr
        20              25              30
Thr Arg Gly Gly Lys Ile Pro Ile Arg Trp Thr Ala Pro Glu Ala Ile
        35              40              45
Ala Tyr Arg Lys Phe Thr Ser Ala Ser Asp
        50              55
```

FIG. 15A

```
  1 TCGGGTCGGA CCCACGCGCA GCGGCCGGAG ATGCAGCGGG GCGCCGCGCT GTGCCTGCGA
    AGCCCAGCCT GGGTGCGCGT CGCCGGCCTC TACGTCGCCC CGCGGCGCGA CACGGACGCT
  1                                  M  Q  R  G   A  A  L    C  L  R

61 CTGTGGCTCT GCCTGGGACT CCTGGACGGC CTGGTGAGTG GCTACTCCAT GACCCCCCCG
    GACACCGAGA CGGACCCTGA GGACCTGCCG GACCACTCAC CGATGAGGTA CTGGGGGGGC
 11 L  W  L  C   L  G  L   L  D  G   L  V  S  G   Y  S  M   T  P  P

121 ACCTTGAACA TCACGGAGGA GTCACACGTC ATCGACACCG GTGACAGCCT GTCCATCTCC
    TGGAACTTGT AGTGCCTCCT CAGTGTGCAG TAGCTGTGGC CACTGTCGGA CAGGTAGAGG
 31 T  L  N  I   T  E  E   S  H  V   I  D  T  G   D  S  L   S  I  S

181 TGCAGGGGAC AGCACCCCCT CGAGTGGGCT TGGCCAGGAG CTCAGGAGGC GCCAGCCACC
    ACGTCCCCTG TCGTGGGGGA GCTCACCCGA ACCGGTCCTC GAGTCCTCCG CGGTCGGTGG
 51 C  R  G  Q   H  P  L   E  W  A   W  P  G  A   Q  E  A   P  A  T

241 GGAGACAAGG ACAGCGAGGA CACGGGGGTG GTGCGAGACT GCGAGGGCAC AGACGCCAGG
    CCTCTGTTCC TGTCGCTCCT GTGCCCCCAC CACGCTCTGA CGCTCCCGTG TCTGCGGTCC
 71 G  D  K  D   S  E  D   T  G  V   V  R  D  C   E  G  T   D  A  R

301 CCCTACTGCA AGGTGTTGCT GCTGCACGAG GTACATGCCA ACGACACAGG CAGCTACGTC
    GGGATGACGT TCCACAACGA CGACGTGCTC CATGTACGGT TGCTGTGTCC GTCGATGCAG
 91 P  Y  C  K   V  L  L   L  H  E   V  H  A  N   D  T  G   S  Y  V

361 TGCTACTACA AGTACATCAA GGCACGCATC GAGGGCACCA CGGCCGCCAG CTCCTACGTG
    ACGATGATGT TCATGTAGTT CCGTGCGTAG CTCCCGTGGT GCCGGCGGTC GAGGATGCAC
111 C  Y  Y  K   Y  I  K   A  R  I   E  G  T  T   A  A  S   S  Y  V

421 TTCGTGAGAG ACTTTGAGCA GCCATTCATC AACAAGCCTG ACACGCTCTT GGTCAACAGG
    AAGCACTCTC TGAAACTCGT CGGTAAGTAG TTGTTCGGAC TGTGCGAGAA CCAGTTGTCC
131 F  V  R  D   F  E  Q   P  F  I   N  K  P  D   T  L  L   V  N  R

481 AAGGACGCCA TGTGGGTGCC CTGTCTGGTG TCCATCCCCG GCCTCAATGT CACGCTGCGC
    TTCCTGCGGT ACACCCACGG GACAGACCAC AGGTAGGGGC CGGAGTTACA GTGCGACGCG
151 K  D  A  M   W  V  P   C  L  V   S  I  P  G   L  N  V   T  L  R

541 TCGCAAAGCT CGGTGCTGTG GCCAGACGGG CAGGAGGTGG TGTGGGATGA CCGGCGGGGC
    AGCGTTTCGA GCCACGACAC CGGTCTGCCC GTCCTCCACC ACACCCTACT GGCCGCCCCG
171 S  Q  S  S   V  L  W   P  D  G   Q  E  V  V   W  D  D   R  R  G

601 ATGCTCGTGT CCACGCCACT GCTGCACGAT GCCCTGTACC TGCAGTGCGA GACCACCTGG
    TACGAGCACA GGTGCGGTGA CGACGTGCTA CGGGACATGG ACGTCACGCT CTGGTGGACC
191 M  L  V  S   T  P  L   L  H  D   A  L  Y  L   Q  C  E   T  T  W

661 GGAGACCAGG ACTTCCTTTC CAACCCCTTC CTGGTGCACA TCACAGGCAA CGAGCTCTAT
    CCTCTGGTCC TGAAGGAAAG GTTGGGGAAG GACCACGTGT AGTGTCCGTT GCTCGAGATA
211 G  D  Q  D   F  L  S   N  P  F   L  V  H  I   T  G  N   E  L  Y
```

FIG. 15B

```
721 GACATCCAGC TGTTGCCCAG GAAGTCGCTG GAGCTGCTGG TAGGGGAGAA GCTGGTCCTG
    CTGTAGGTCG ACAACGGGTC CTTCAGCGAC CTCGACGACC ATCCCCTCTT CGACCAGGAC
231  D  I  Q  L    L  P  R    K  S  L    E  L  L    V  G  E  K    L  V  L

781 AACTGCACCG TGTGGGCTGA GTTTAACTCA GGTGTCACCT TTGACTGGGA CTACCCAGGG
    TTGACGTGGC ACACCCGACT CAAATTGAGT CCACAGTGGA AACTGACCCT GATGGGTCCC
251  N  C  T  V    W  A  E    F  N  S    G  V  T  F    D  W  D    Y  P  G

841 AAGCAGGCAG AGCGGGGTAA GTGGGTGCCC GAGCGACGCT CCCAGCAGAC CCACACAGAA
    TTCGTCCGTC TCGCCCCATT CACCCACGGG CTCGCTGCGA GGGTCGTCTG GGTGTGTCTT
271  K  Q  A  E    R  G  K    W  V  P    E  R  R  S    Q  Q  T    H  T  E

901 CTCTCCAGCA TCCTGACCAT CCACAACGTC AGCCAGCACG ACCTGGGCTC GTATGTGTGC
    GAGAGGTCGT AGGACTGGTA GGTGTTGCAG TCGGTCGTGC TGGACCCGAG CATACACACG
291  L  S  S  I    L  T  I    H  N  V    S  Q  H  D    L  G  S    Y  V  C

961 AAGGCCAACA ACGGCATCCA GCGATTTCGG GAGAGCACCG AGGTCATTGT GCATGAAAAT
    TTCCGGTTGT TGCCGTAGGT CGCTAAAGCC CTCTCGTGGC TCCAGTAACA CGTACTTTTA
311  K  A  N  N    G  I  Q    R  F  R    E  S  T  E    V  I  V    H  E  N

1021 CCCTTCATCA GCGTCGAGTG GCTCAAAGGA CCCATCCTGG AGGCCACGGC AGGAGACGAG
     GGGAAGTAGT CGCAGCTCAC CGAGTTTCCT GGGTAGGACC TCCGGTGCCG TCCTCTGCTC
331  P  F  I  S    V  E  W    L  K  G    P  I  L  E    A  T  A    G  D  E

1081 CTGGTGAAGC TGCCCGTGAA GCTGGCAGCG TACCCCCCGC CCGAGTTCCA GTGGTACAAG
     GACCACTTCG ACGGGCACTT CGACCGTCGC ATGGGGGGCG GGCTCAAGGT CACCATGTTC
351  L  V  K  L    P  V  K    L  A  A    Y  P  P  P    E  F  Q    W  Y  K

1141 GATGGAAAGG CACTGTCCGG GCGCCACAGT CCACATGCCC TGGTGCTCAA GGAGGTGACA
     CTACCTTTCC GTGACAGGCC CGCGGTGTCA GGTGTACGGG ACCACGAGTT CCTCCACTGT
371  D  G  K  A    L  S  G    R  H  S    P  H  A  L    V  L  K    E  V  T

1201 GAGGCCAGCA CAGGCACCTA CACCCTCGCC CTGTGGAACT CCGCTGCTGG CCTGAGGCGC
     CTCCGGTCGT GTCCGTGGAT GTGGGAGCGG GACACCTTGA GGCGACGACC GGACTCCGCG
391  E  A  S  T    G  T  Y    T  L  A    L  W  N  S    A  A  G    L  R  R

1261 AACATCAGCC TGGAGCTGGT GGTGAATGTG CCCCCCCAGA TACATGAGAA GGAGGCCTCC
     TTGTAGTCGG ACCTCGACCA CCACTTACAC GGGGGGGTCT ATGTACTCTT CCTCCGGAGG
411  N  I  S  L    E  L  V    V  N  V    P  P  Q  I    H  E  K    E  A  S

1321 TCCCCCAGCA TCTACTCGCG TCACAGCCGC CAGGCCCTCA CCTGCACGGC CTACGGGGTG
     AGGGGGTCGT AGATGAGCGC AGTGTCGGCG GTCCGGGAGT GGACGTGCCG GATGCCCCAC
431  S  P  S  I    Y  S  R    H  S  R    Q  A  L  T    C  T  A    Y  G  V

1381 CCCCTGCCTC TCAGCATCCA GTGGCACTGG CGGCCCTGGA CACCCTGCAA GATGTTTGCC
     GGGGACGGAG AGTCGTAGGT CACCGTGACC GCCGGGACCT GTGGGACGTT CTACAAACGG
451  P  L  P  L    S  I  Q    W  H  W    R  P  W  T    P  C  K    M  F  A

1441 CAGCGTAGTC TCCGGCGGCG GCAGCAGCAA GACCTCATGC CACAGTGCCG TGACTGGAGG
     GTCGCATCAG AGGCCGCCGC CGTCGTCGTT CTGGAGTACG GTGTCACGGC ACTGACCTCC
471  Q  R  S  L    R  R  R    Q  Q  Q    D  L  M  P    Q  C  R    D  W  R
```

FIG. 15C

```
1501 GCGGTGACCA CGCAGGATGC CGTGAACCCC ATCGAGAGCC TGGACACCTG GACCGAGTTT
     CGCCACTGGT GCGTCCTACG GCACTTGGGG TAGCTCTCGG ACCTGTGGAC CTGGCTCAAA
 491 A  V  T  T   Q  D  A    V  N  P    I  E  S  L   D  T  W    T  E  F

1561 GTGGAGGGAA AGAATAAGAC TGTGAGCAAG CTGGTGATCC AGAATGCCAA CGTGTCTGCC
     CACCTCCCTT TCTTATTCTG ACACTCGTTC GACCACTAGG TCTTACGGTT GCACAGACGG
 511 V  E  G  K   N  K  T    V  S  K   L  V  I  Q    N  A  N    V  S  A

1621 ATGTACAAGT GTGTGGTCTC CAACAAGGTG GGCCAGGATG AGCGGCTCAT CTACTTCTAT
     TACATGTTCA CACACCAGAG GTTGTTCCAC CCGGTCCTAC TCGCCGAGTA GATGAAGATA
 531 M  Y  K  C   V  V  S    N  K  V   G  Q  D  E    R  L  I    Y  F  Y

1681 GTGACCACCA TCCCCGACGG CTTCACCATC GAATCCAAGC CATCCGAGGA GCTACTAGAG
     CACTGGTGGT AGGGGCTGCC GAAGTGGTAG CTTAGGTTCG GTAGGCTCCT CGATGATCTC
 551 V  T  T  I   P  D  G    F  T  I   E  S  K  P    S  E  E    L  L  E

1741 GGCCAGCCGG TGCTCCTGAG CTGCCAAGCC GACAGCTACA AGTACGAGCA TCTGCGCTGG
     CCGGTCGGCC ACGAGGACTC GACGGTTCGG CTGTCGATGT TCATGCTCGT AGACGCGACC
 571 G  Q  P  V   L  L  S    C  Q  A   D  S  Y  K    Y  E  H    L  R  W

1801 TACCGCCTCA ACCTGTCCAC GCTGCACGAT GCGCACGGGA ACCCGCTTCT GCTCGACTGC
     ATGGCGGAGT TGGACAGGTG CGACGTGCTA CGCGTGCCCT TGGGCGAAGA CGAGCTGACG
 591 Y  R  L  N   L  S  T    L  H  D   A  H  G  N    P  L  L    L  D  C

1861 AAGAACGTGC ATCTGTTCGC CACCCCTCTG GCCGCCAGCC TGGAGGAGGT GGCACCTGGG
     TTCTTGCACG TAGACAAGCG GTGGGGAGAC CGGCGGTCGG ACCTCCTCCA CCGTGGACCC
 611 K  N  V  H   L  F  A    T  P  L   A  A  S  L    E  E  V    A  P  G

1921 GCGCGCCACG CCACGCTCAG CCTGAGTATC CCCCGCGTCG CGCCCGAGCA CGAGGGCCAC
     CGCGCGGTGC GGTGCGAGTC GGACTCATAG GGGGCGCAGC GCGGGCTCGT GCTCCCGGTG
 631 A  R  H  A   T  L  S    L  S  I   P  R  V  A    P  E  H    E  G  H

1981 TATGTGTGCG AAGTGCAAGA CCGGCGCAGC CATGACAAGC ACTGCCACAA GAAGTACCTG
     ATACACACGC TTCACGTTCT GGCCGCGTCG GTACTGTTCG TGACGGTGTT CTTCATGGAC
 651 Y  V  C  E   V  Q  D    R  R  S   H  D  K  H    C  H  K    K  Y  L

2041 TCGGTGCAGG CCCTGGAAGC CCCTCGGCTC ACGCAGAACT TGACCGACCT CCTGGTGAAC
     AGCCACGTCC GGGACCTTCG GGGAGCCGAG TGCGTCTTGA ACTGGCTGGA GGACCACTTG
 671 S  V  Q  A   L  E  A    P  R  L   T  Q  N  L    T  D  L    L  V  N

2101 GTGAGCGACT CGCTGGAGAT GCAGTGCTTG GTGGCCGGAG CGCACGCGCC CAGCATCGTG
     CACTCGCTGA GCGACCTCTA CGTCACGAAC CACCGGCCTC GCGTGCGCGG GTCGTAGCAC
 691 V  S  D  S   L  E  M    Q  C  L   V  A  G  A    H  A  P    S  I  V

2161 TGGTACAAAG ACGAGAGGCT GCTGGAGGAA AAGTCTGGAG TCGACTTGGC GGACTCCAAC
     ACCATGTTTC TGCTCTCCGA CGACCTCCTT TTCAGACCTC AGCTGAACCG CCTGAGGTTG
 711 W  Y  K  D   E  R  L    L  E  E   K  S  G  V    D  L  A    D  S  N

2221 CAGAAGCTGA GCATCCAGCG CGTGCGCGAG GAGGATGCGG GACGCTATCT GTGCAGCGTG
     GTCTTCGACT CGTAGGTCGC GCACGCGCTC CTCCTACGCC CTGCGATAGA CACGTCGCAC
 731 Q  K  L  S   I  Q  R    V  R  E   E  D  A  G    R  Y  L    C  S  V
```

FIG. 15D

```
2281 TGCAACGCCA AGGGCTGCGT CAACTCCTCC GCCAGCGTGG CCGTGGAAGG CTCCGAGGAT
     ACGTTGCGGT TCCCGACGCA GTTGAGGAGG CGGTCGCACC GGCACCTTCC GAGGCTCCTA
 751 C   N   A   K      G   C   V      N   S   S      A   S   V      V   E   G      S   E   D

2341 AAGGGCAGCA TGGAGATCGT GATCCTTGTC GGTACCGGCG TCATCGCTGT CTTCTTCTGG
     TTCCCGTCGT ACCTCTAGCA CTAGGAACAG CCATGGCCGC AGTAGCGACA GAAGAAGACC
 771 K   G   S      M   E   I      V   I   L      V   G   T      G   V   I      A   V   F   F   W

2401 GTCCTCCTCC TCCTCATCTT CTGTAACATG AGGAGGCCGG CCCACGCAGA CATCAAGACG
     CAGGAGGAGG AGGAGTAGAA GACATTGTAC TCCTCCGGCC GGGTGCGTCT GTAGTTCTGC
 791 V   L   L      L   I   F      C   N   M      R   R   P      A   H   A   D      I   K   T

2461 GGCTACCTGT CCATCATCAT GGACCCCGGG GAGGTGCCTC TGGAGGAGCA ATGCGAATAC
     CCGATGGACA GGTAGTAGTA CCTGGGGCCC CTCCACGGAG ACCTCCTCGT TACGCTTATG
 811 G   Y   L      S   I   I   M      D   P   G      E   V   P      L   E   E      Q   C   E   Y

2521 CTGTCCTACG ATGCCAGCCA GTGGGAATTC CCCCGAGAGC GGCTGCACCT GGGGAGAGTG
     GACAGGATGC TACGGTCGGT CACCCTTAAG GGGGCTCTCG CCGACGTGGA CCCCTCTCAC
 831 L   S   Y      D   A   S   Q      W   E   F      P   R   E   R      L   H   L      G   R   V

2581 CTCGGCTACG GCGCCTTCGG GAAGGTGGTG GAAGCCTCCG CTTTCGGCAT CCACAAGGGC
     GAGCCGATGC CGCGGAAGCC CTTCCACCAC CTTCGGAGGC GAAAGCCGTA GGTGTTCCCG
 851 L   G   Y      G   A   F   G      K   V   V      E   A   S   A      F   G   I      H   K   G

2641 AGCAGCTGTG ACACCGTGGC CGTGAAAATG CTGAAAGAGG GCGCCACGGC CAGCGAGCAC
     TCGTCGACAC TGTGGCACCG GCACTTTTAC GACTTTCTCC CGCGGTGCCG GTCGCTCGTG
 871 S   S   C      D   T   V   A      V   K   M      L   K   E   G      A   T   A      S   E   H

2701 CGCGCGCTGA TGTCGGAGCT CAAGATCCTC ATTCACATCG GCAACCACCT CAACGTGGTC
     GCGCGCGACT ACAGCCTCGA GTTCTAGGAG TAAGTGTAGC CGTTGGTGGA GTTGCACCAG
 891 R   A   L   M      S   E   L      K   I   L      I   H   I   G      N   H   L      N   V   V

2761 AACCTCCTCG GGGCGTGCAC CAAGCCGCAG GGCCCCCTCA TGGTGATCGT GGAGTTCTGC
     TTGGAGGAGC CCCGCACGTG GTTCGGCGTC CCGGGGGAGT ACCACTAGCA CCTCAAGACG
 911 N   L   L      G   A   C   T      K   P   Q      G   P   L   M      V   I   V      E   F   C

2821 AAGTACGGCA ACCTCTCCAA CTTCCTGCGC GCCAAGCGGG ACGCCTTCAG CCCCTGCGCG
     TTCATGCCGT TGGAGAGGTT GAAGGACGCG CGGTTCGCCC TGCGGAAGTC GGGGACGCGC
 931 K   Y   G      N   L   S   N      F   L   R      A   K   R   D      A   F   S      P   C   A

2881 GAGAAGTCTC CCGAGCAGCG CGGACGCTTC CGCGCCATGG TGGAGCTCGC CAGGCTGGAT
     CTCTTCAGAG GGCTCGTCGC GCCTGCGAAG GCGCGGTACC ACCTCGAGCG GTCCGACCTA
 951 E   K   S      P   E   Q   R      G   R   F      R   A   M   V      E   L   A      R   L   D

2941 CGGAGGCGGC CGGGGAGCAG CGACAGGGTC CTCTTCGCGC GGTTCTCGAA GACCGAGGGC
     GCCTCCGCCG GCCCCTCGTC GCTGTCCCAG GAGAAGCGCG CCAAGAGCTT CTGGCTCCCG
 971 R   R   R      P   G   S   S      D   R   V      L   F   A   R      F   S   K      T   E   G

3001 GGAGCGAGGC GGGCTTCTCC AGACCAAGAA GCTGAGGACC TGTGGCTGAG CCCGCTGACC
     CCTCGCTCCG CCCGAAGAGG TCTGGTTCTT CGACTCCTGG ACACCGACTC GGGCGACTGG
 991 G   A   R   R      A   S   P      D   Q   E      A   E   D   L      W   L   S      P   L   T
```

FIG. 15E

```
3061 ATGGAAGATC TTGTCTGCTA CAGCTTCCAG GTGGCCAGAG GGATGGAGTT CCTGGCTTCC
     TACCTTCTAG AACAGACGAT GTCGAAGGTC CACCGGTCTC CCTACCTCAA GGACCGAAGG
1011 M  E  D  L  V  C  Y  S  F  Q  V  A  R  G  M  E  F  L  A  S

3121 CGAAAGTGCA TCCACAGAGA CCTGGCTGCT CGGAACATTC TGCTGTCGGA AAGCGACGTG
     GCTTTCACGT AGGTGTCTCT GGACCGACGA GCCTTGTAAG ACGACAGCCT TTCGCTGCAC
1031 R  K  C  I  H  R  D  L  A  A  R  N  I  L  L  S  E  S  D  V

3181 GTGAAGATCT GTGACTTTGG CCTTGCCCGG GACATCTACA AGACCCTGA CTACGTCCGC
     CACTTCTAGA CACTGAAACC GGAACGGGCC CTGTAGATGT TTCTGGGACT GATGCAGGCG
1051 V  K  I  C  D  F  G  L  A  R  D  I  Y  K  D  P  D  Y  V  R

3241 AAGGGCAGTG CCCGGCTGCC CCTGAAGTGG ATGGCCCCTG AAAGCATCTT CGACAAGGTG
     TTCCCGTCAC GGGCCGACGG GGACTTCACC TACCGGGGAC TTTCGTAGAA GCTGTTCCAC
1071 K  G  S  A  R  L  P  L  K  W  M  A  P  E  S  I  F  D  K  V

3301 TACACCACGC AGAGTGACGT GTGGTCCTTT GGGGTGCTTC TCTGGGAGAT CTTCTCTCTG
     ATGTGGTGCG TCTCACTGCA CACCAGGAAA CCCCACGAAG AGACCCTCTA GAAGAGAGAC
1091 Y  T  T  Q  S  D  V  W  S  F  G  V  L  L  W  E  I  F  S  L

3361 GGGGCCTCCC CGTACCCTGG GGTGCAGATC AATGAGGAGT TCTGCCAGCG GCTGAGAGAC
     CCCCGGAGGG GCATGGGACC CCACGTCTAG TTACTCCTCA AGACGGTCGC CGACTCTCTG
1111 G  A  S  P  Y  P  G  V  Q  I  N  E  E  F  C  Q  R  L  R  D

3421 GGCACAAGGA TGAGGGCCCC GGAGCTGGCC ACTCCCGCCA TACGCCGCAT CATGCTGAAC
     CCGTGTTCCT ACTCCCGGGG CCTCGACCGG TGAGGGCGGT ATGCGGCGTA GTACGACTTG
1131 G  T  R  M  R  A  P  E  L  A  T  P  A  I  R  R  I  M  L  N

3481 TGCTGGTCCG GAGACCCCAA GGCGAGACCT GCATTCTCGG AGCTGGTGGA GATCCTGGGG
     ACGACCAGGC CTCTGGGGTT CCGCTCTGGA CGTAAGAGCC TCGACCACCT CTAGGACCCC
1151 C  W  S  G  D  P  K  A  R  P  A  F  S  E  L  V  E  I  L  G

3541 GACCTGCTCC AGGGCAGGGG CCTGCAAGAG GAAGAGGAGG TCTGCATGGC CCCGCGCAGC
     CTGGACGAGG TCCCGTCCCC GGACGTTCTC CTTCTCCTCC AGACGTACCG GGGCGCGTCG
1171 D  L  L  Q  G  R  G  L  Q  E  E  E  E  V  C  M  A  P  R  S

3601 TCTCAGAGCT CAGAAGAGGG CAGCTTCTCG CAGGTGTCCA CCATGGCCCT ACACATCGCC
     AGAGTCTCGA GTCTTCTCCC GTCGAAGAGC GTCCACAGGT GGTACCGGGA TGTGTAGCGG
1191 S  Q  S  S  E  E  G  S  F  S  Q  V  S  T  M  A  L  H  I  A

3661 CAGGCTGACG CTGAGGACAG CCCGCCAAGC CTGCAGCGCC ACAGCCTGGC CGCCAGGTAT
     GTCCGACTGC GACTCCTGTC GGGCGGTTCG GACGTCGCGG TGTCGGACCG GCGGTCCATA
1211 Q  A  D  A  E  D  S  P  P  S  L  Q  R  H  S  L  A  A  R  Y

3721 TACAACTGGG TGTCCTTTCC CGGGTGCCTG GCCAGAGGGG CTGAGACCCG TGGTTCCTCC
     ATGTTGACCC ACAGGAAAGG GCCCACGGAC CGGTCTCCCC GACTCTGGGC ACCAAGGAGG
1231 Y  N  W  V  S  F  P  G  C  L  A  R  G  A  E  T  R  G  S  S

3781 AGGATGAAGA CATTTGAGGA ATTCCCCATG ACCCCAACGA CCTACAAAGG CTCTGTGGAC
     TCCTACTTCT GTAAACTCCT TAAGGGGTAC TGGGGTTGCT GGATGTTTCC GAGACACCTG
1251 R  M  K  T  F  E  E  F  P  M  T  P  T  T  Y  K  G  S  V  D
```

FIG. 15F

```
3841 AACCAGACAG ACAGTGGGAT GGTGCTGGCC TCGGAGGAGT TTGAGCAGAT AGAGAGCAGG
     TTGGTCTGTC TGTCACCCTA CCACGACCGG AGCCTCCTCA AACTCGTCTA TCTCTCGTCC
1271 N  Q  T  D     S  G  M     V  L  A     S  E  E  F     E  Q  I     E  S  R

3901 CATAGACAAG AAAGCGGCTT CAGGTAGCTG AAGCAGAGAG AGAGAAGGCA GCATACGTCA
     GTATCTGTTC TTTCGCCGAA GTCCATCGAC TTCGTCTCTC TCTCTTCCGT CGTATGCAGT
1291 H  R  Q  E     S  G  F     R  O

3961 GCATTTTCTT CTCTGCACTT ATAAGAAAGA TCAAAGACTT TAAGACTTTC GCTATTTCTT
     CGTAAAAGAA GAGACGTGAA TATTCTTTCT AGTTTCTGAA ATTCTGAAAG CGATAAAGAA

4021 CTGCTATCTA CTACAAACTT CAAAGAGGAA CCAGGAGGCC AAGAGGAGCA TGAAAGTGGA
     GACGATAGAT GATGTTTGAA GTTTCTCCTT GGTCCTCCGG TTCTCCTCGT ACTTTCACCT

4081 CAAGGAGTGT GACCACTGAA GCACCACAGG GAGGGGTTAG GCCTCCGGAT GACTGCGGGC
     GTTCCTCACA CTGGTGACTT CGTGGTGTCC CTCCCCAATC CGGAGGCCTA CTGACGCCCG

4141 AGGCCTGGAT AATATCCAGC CTCCCACAAG AAGCTGGTGG AGCAGAGTGT TCCCTGACTC
     TCCGGACCTA TTATAGGTCG GAGGGTGTTC TTCGACCACC TCGTCTCACA AGGGACTGAG

4201 CTCCAAGGAA AGGGAGACGC CCTTTCATGG TCTGCTGAGT AACAGGTGCC TTCCCAGACA
     GAGGTTCCTT TCCCTCTGCG GGAAAGTACC AGACGACTCA TTGTCCACGG AAGGGTCTGT

4261 CTGGCGTTAC TGCTTGACCA AAGAGCCCTC AAGCGGCCCT TATGCCAGCG TGACAGAGGG
     GACCGCAATG ACGAACTGGT TTCTCGGGAG TTCGCCGGGA ATACGGTCGC ACTGTCTCCC

4321 CTCACCTCTT GCCTTCTAGG TCACTTCTCA CAATGTCCCT TCAGCACCTG ACCCTGTGCC
     GAGTGGAGAA CGGAAGATCC AGTGAAGAGT GTTACAGGGA AGTCGTGGAC TGGGACACGG

4381 CGCCAGTTAT TCCTTGGTAA TATGAGTAAT ACATCAAAGA GTAGT
     GCGGTCAATA AGGAACCATT ATACTCATTA TGTAGTTTCT CATCA
```

FIG. 16A

```
  1 ATGGCTGGGA TTTTCTATTT CGCCCTATTT TCGTGTCTCT TCGGGATTTG
    TACCGACCCT AAAAGATAAA GCGGGATAAA AGCACAGAGA AGCCCTAAAC
  1 MetAlaGlyI lePheTyrPh eAlaLeuPhe SerCysLeuP heGlyIleCy
    CGACGCTGTC ACAGGTTCCA GGGTATACCC CGCGAATGAA GTTACCTTAT
    GCTGCGACAG TGTCCAAGGT CCCATATGGG GCGCTTACTT CAATGGAATA
    sAspAlaVal ThrGlySerA rgValTyrPr oAlaAsnGlu ValThrLeuLeu

101 TGGATTCCAG ATCTGTTCAG GGAGAACTTG GGTGGATAGC AAGCCCTCTG
    ACCTAAGGTC TAGACAAGTC CCTCTTGAAC CCACCTATCG TTCGGGAGAC
 35   AspSerAr gSerValGln GlyGluLeuG lyTrpIleAl aSerProLeu
    GAAGGAGGGT GGGAGGAAGT GAGTATCATG GATGAAAAAA ATACACCAAT
    CTTCCTCCCA CCCTCCTTCA CTCATAGTAC CTACTTTTTT TATGTGGTTA
    GluGlyGlyT rpGluGluVa lSerIleMet AspGluLysA snThrProIle

201 CCGAACCTAC CAAGTGTGCA ATGTGATGGA ACCCAGCCAG AATAACTGGC
    GGCTTGGATG GTTCACACGT TACACTACCT TGGGTCGGTC TTATTGACCG
 68   ArgThrTyr GlnValCysA snValMetGl uProSerGln AsnAsnTrpL
    TACGAACTGA TTGGATCACC CGAGAAGGGG CTCAGAGGGT GTATATTGAG
    ATGCTTGACT AACCTAGTGG GCTCTTCCCC GAGTCTCCCA CATATAACTC
    euArgThrAs pTrpIleThr ArgGluGlyA laGlnArgVa lTyrIleGlu

301 ATTAAATTCA CCTTGAGGGA CTGCAATAGT CTTCCGGGCG TCATGGGGAC
    TAATTTAAGT GGAACTCCCT GACGTTATCA GAAGGCCCGC AGTACCCCTG
101   IleLysPheT hrLeuArgAs pCysAsnSer LeuProGlyV alMetGlyTh
    TTGCAAGGAG ACGTTTAACC TGTACTACTA TGAATCAGAC AACGACAAAG
    AACGTTCCTC TGCAAATTGG ACATGATGAT ACTTAGTCTG TTGCTGTTTC
    rCysLysGlu ThrPheAsnL euTyrTyrTy rGluSerAsp AsnAspLysGlu
```

FIG. 16B

```
401 AGCGTTTCAT CAGAGAGAAC CAGTTTGTCA AAATTGACAC CATTGCTGCT
    TCGCAAAGTA GTCTCTCTTG GTCAAACAGT TTTAACTGTG GTAACGACGA
135    ArgPheIl eArgGluAsn GlnPheValL ysIleAspTh rIleAlaAla
    GATGAGAGCT TCACCCAAGT GGACATTGGT GACAGAATCA TGAAGCTGAA
    CTACTCTCGA AGTGGGTTCA CCTGTAACCA CTGTCTTAGT ACTTCGACTT
    AspGluSerP heThrGlnVa lAspIleGly AspArgIleM etLysLeuAsn
501 CACCGAGATC CGGGATGTAG GGCCATTAAG CAAAAAGGGG TTTTACCTGG
    GTGGCTCTAG GCCCTACATC CCGGTAATTC GTTTTTCCCC AAAATGGACC
168    ThrGluIle ArgAspValG lyProLeuSe rLysLysGly PheTyrLeuA
    CTTTTCAGGA TGTGGGGGCC TGCATCGCCC TGGTATCAGT CCGTGTGTTC
    GAAAAGTCCT ACACCCCCGG ACGTAGCGGG ACCATAGTCA GGCACACAAG
    laPheGlnAs pValGlyAla CysIleAlaL euValSerVa lArgValPhe
601 TATAAAAAGT GTCCACTCAC AGTCCGCAAT CTGGCCCAGT TTCCTGACAC
    ATATTTTTCA CAGGTGAGTG TCAGGCGTTA GACCGGGTCA AAGGACTGTG
201 TyrLysLysC ysProLeuTh rValArgAsn LeuAlaGlnP heProAspTh
    CATCACAGGG GCTGATACGT CTTCCCTGGT GGAAGTTCGA GGCTCCTGTG
    GTAGTGTCCC CGACTATGCA GAAGGGACCA CCTTCAAGCT CCGAGGACAC
    rIleThrGly AlaAspThrS erSerLeuVa lGluValArg GlySerCysVal
701 TCAACAACTC AGAAGAGAAA GATGTGCCAA AAATGTACTG TGGGGCAGAT
    AGTTGTTGAG TCTTCTCTTT CTACACGGTT TTTACATGAC ACCCCGTCTA
235    AsnAsnSe rGluGluLys AspValProL ysMetTyrCy sGlyAlaAsp
    GGTGAATGGC TGGTACCCAT TGGCAACTGC CTATGCAACG CTGGGCATGA
    CCACTTACCG ACCATGGGTA ACCGTTGACG GATACGTTGC GACCCGTACT
    GlyGluTrpL euValProIl eGlyAsnCys LeuCysAsnA laGlyHisGlu
801 GGAGCGGAGC GGAGAATGCC AAGCTTGCAA AATTGGATAT TACAAGGCTC
    CCTCGCCTCG CCTCTTACGG TTCGAACGTT TTAACCTATA ATGTTCCGAG
268    GluArgSer GlyGluCysG lnAlaCysLy sIleGlyTyr TyrLysAlaL
    TCTCCACGGA TGCCACCTGT GCCAAGTGCC CACCCCACAG CTACTCTGTC
    AGAGGTGCCT ACGGTGGACA CGGTTCACGG GTGGGGTGTC GATGAGACAG
    euSerThrAs pAlaThrCys AlaLysCysP roProHisSe rTyrSerVal
```

FIG. 16C

```
 901 TGGGAAGGAG CCACCTCGTG CACCTGTGAC CGAGGCTTTT TCAGAGCTGA
     ACCCTTCCTC GGTGGAGCAC GTGGACACTG GCTCCGAAAA AGTCTCGACT
 301 TrpGluGlyA laThrSerCy sThrCysAsp ArgGlyPheP heArgAlaAs
     CAACGATGCT GCCTCTATGC CCTGCACCCG TCCACCATCT GCTCCCCTGA
     GTTGCTACGA CGGAGATACG GGACGTGGGC AGGTGGTAGA CGAGGGGACT
     pAsnAspAla AlaSerMetP roCysThrAr gProProSer AlaProLeuAsn
1001 ACTTGATTTC AAATGTCAAC GAGACATCTG TGAACTTGGA ATGGAGTAGC
     TGAACTAAAG TTTACAGTTG CTCTGTAGAC ACTTGAACCT TACCTCATCG
 335    LeuIleSe rAsnValAsn GluThrSerV alAsnLeuGl uTrpSerSer
     CCTCAGAATA CAGGTGGCCG CCAGGACATT TCCTATAATG TGGTATGCAA
     GGAGTCTTAT GTCCACCGGC GGTCCTGTAA AGGATATTAC ACCATACGTT
     ProGlnAsnT hrGlyGlyAr gGlnAspIle SerTyrAsnV alValCysLys
1101 GAAATGTGGA GCTGGTGACC CCAGCAAGTG CCGACCCTGT GGAAGTGGGG
     CTTTACACCT CGACCACTGG GGTCGTTCAC GGCTGGGACA CCTTCACCCC
 368    LysCysGly AlaGlyAspP roSerLysCy sArgProCys GlySerGlyV
     TCCACTACAC CCCACAGCAG AATGGCTTGA AGACCACCAA AGGCTCCATC
     AGGTGATGTG GGGTGTCGTC TTACCGAACT TCTGGTGGTT TCCGAGGTAG
     alHisTyrTh rProGlnGln AsnGlyLeuL ysThrThrLy sGlySerIle
1201 ACTGACCTCC TAGCTCATAC CAATTACACC TTTGAAATCT GGGCTGTGAA
     TGACTGGAGG ATCGAGTATG GTTAATGTGG AAACTTTAGA CCCGACACTT
 401 ThrAspLeuL euAlaHisTh rAsnTyrThr PheGluIleT rpAlaValAs
     TGGAGTGTCC AAATATAACC CTAACCCAGA CCAATCAGTT TCTGTCACTG
     ACCTCACAGG TTTATATTGG GATTGGGTCT GGTTAGTCAA AGACAGTGAC
     nGlyValSer LysTyrAsnP roAsnProAs pGlnSerVal SerValThrVal
1301 TGACCACCAA CCAAGCAGCA CCATCATCCA TTGCTTTGGT CCAGGCTAAA
     ACTGGTGGTT GGTTCGTCGT GGTAGTAGGT AACGAAACCA GGTCCGATTT
 435    ThrThrAs nGlnAlaAla ProSerSerI leAlaLeuVa lGlnAlaLys
     GAAGTCACAA GATACAGTGT GGCACTGGCT TGGCTGGAAC CAGATCGGCC
     CTTCAGTGTT CTATGTCACA CCGTGACCGA ACCGACCTTG GTCTAGCCGG
     GluValThrA rgTyrSerVa lAlaLeuAla TrpLeuGluP roAspArgPro
```

FIG. 16D

```
1401 CAATGGGGTA ATCCTGGAAT ATGAAGTCAA GTATTATGAG AAGGATCAGA
     GTTACCCCAT TAGGACCTTA TACTTCAGTT CATAATACTC TTCCTAGTCT
 468    AsnGlyVal IleLeuGluT yrGluValLy sTyrTyrGlu LysAspGlnA
     ATGAGCGAAG CTATCGTATA GTTCGGACAG CTGCCAGGAA CACAGATATC
     TACTCGCTTC GATAGCATAT CAAGCCTGTC GACGGTCCTT GTGTCTATAG
        snGluArgSe rTyrArgIle ValArgThrA laAlaArgAs nThrAspIle
1501 AAAGGCCTGA ACCCTCTCAC TTCCTATGTT TTCCACGTGC GAGCCAGGAC
     TTTCCGGACT TGGGAGAGTG AAGGATACAA AAGGTGCACG CTCGGTCCTG
 501   LysGlyLeuA snProLeuTh rSerTyrVal PheHisValA rgAlaArgTh
     AGCAGCTGGC TATGGAGACT TCAGTGAGCC CTTGGAGGTT ACAACCAACA
     TCGTCGACCG ATACCTCTGA AGTCACTCGG GAACCTCCAA TGTTGGTTGT
        rAlaAlaGly TyrGlyAspP heSerGluPr oLeuGluVal ThrThrAsnThr
1601 CAGTGCCTTC CCGGATCATT GGAGATGGGG CTAACTCCAC AGTCCTTCTG
     GTCACGGAAG GGCCTAGTAA CCTCTACCCC GATTGAGGTG TCAGGAAGAC
 535    ValProSe rArgIleIle GlyAspGlyA laAsnSerTh rValLeuLeu
     GTCTCTGTCT CGGGCAGTGT GGTGCTGGTG GTAATTCTCA TTGCAGCTTT
     CAGAGACAGA GCCCGTCACA CCACGACCAC CATTAAGAGT AACGTCGAAA
        ValSerValS erGlySerVa lValLeuVal ValIleLeuI leAlaAlaPhe
1701 TGTCATCAGC CGGAGACGGA GTAAATACAG TAAAGCCAAA CAAGAAGCGG
     ACAGTAGTCG GCCTCTGCCT CATTTATGTC ATTTCGGTTT GTTCTTCGCC
 568    ValIleSer ArgArgArgS erLysTyrSe rLysAlaLys GlnGluAlaA
     ATGAAGAGAA ACATTTGAAT CAAGGTGTAA GAACATATGT GGACCCCTTT
     TACTTCTCTT TGTAAACTTA GTTCCACATT CTTGTATACA CCTGGGGAAA
        spGluGluLy sHisLeuAsn GlnGlyValA rgThrTyrVa lAspProPhe
```

FIG. 16E

```
1801 ACGTACGAAG ATCCCAACCA AGCAGTGCGA GAGTTTGCCA AAGAAATTGA
     TGCATGCTTC TAGGGTTGGT TCGTCACGCT CTCAAACGGT TTCTTTAACT
 601 ThrTyrGluA spProAsnGl nAlaValArg GluPheAlaL ysGluIleAs
     CGCATCCTGC ATTAAGATTG AAAAAGTTAT AGGAGTTGGT GAATTTGGTG
     GCGTAGGACG TAATTCTAAC TTTTTCAATA TCCTCAACCA CTTAAACCAC
     pAlaSerCys IleLysIleG luLysValIl eGlyValGly GluPheGlyGlu
1901 AGGTATGCAG TGGGCGTCTC AAAGTGCCTG GCAAGAGAGA GATCTGTGTG
     TCCATACGTC ACCCGCAGAG TTTCACGGAC CGTTCTCTCT CTAGACACAC
 635    ValCysSe rGlyArgLeu LysValProG lyLysArgGl uIleCysVal
     GCTATCAAGA CTCTGAAAGC TGGTTATACA GACAAACAGA GGAGAGACTT
     CGATAGTTCT GAGACTTTCG ACCAATATGT CTGTTTGTCT CCTCTCTGAA
     AlaIleLysT hrLeuLysAl aGlyTyrThr AspLysGlnA rgArgAspPhe
2001 CCTGAGTGAG GCCAGCATCA TGGGACAGTT TGACCATCCG AACATCATTC
     GGACTCACTC CGGTCGTAGT ACCCTGTCAA ACTGGTAGGC TTGTAGTAAG
 668    LeuSerGlu AlaSerIleM etGlyGlnPh eAspHisPro AsnIleIleH
     ACTTGGAAGG CGTGGTCACT AAATGTAAAC CAGTAATGAT CATAACAGAG
     TGAACCTTCC GCACCAGTGA TTTACATTTG GTCATTACTA GTATTGTCTC
     isLeuGluGl yValValThr LysCysLysP roValMetIl eIleThrGlu
2101 TACATGGAGA ATGGCTCCTT GGATGCATTC CTCAGGAAAA ATGATGGCAG
     ATGTACCTCT TACCGAGGAA CCTACGTAAG GAGTCCTTTT TACTACCGTC
 701 TyrMetGluA snGlySerLe uAspAlaPhe LeuArgLysA snAspGlyAr
     ATTTACAGTC ATTCAGCTGG TGGGCATGCT TCGTGGCATT GGGTCTGGGA
     TAAATGTCAG TAAGTCGACC ACCCGTACGA AGCACCGTAA CCCAGACCCT
     gPheThrVal IleGlnLeuV alGlyMetLe uArgGlyIle GlySerGlyMet
2201 TGAAGTATTT ATCTGATATG AGCTATGTGC ATCGTGATCT GGCCGCACGG
     ACTTCATAAA TAGACTATAC TCGATACACG TAGCACTAGA CCGGCGTGCC
 735    LysTyrLe uSerAspMet SerTyrValH isArgAspLe uAlaAlaArg
     AACATCCTGG TGAACAGCAA CTTGGTCTGC AAAGTGTCTG ATTTTGGCAT
     TTGTAGGACC ACTTGTCGTT GAACCAGACG TTTCACAGAC TAAAACCGTA
     AsnIleLeuV alAsnSerAs nLeuValCys LysValSerA spPheGlyMet
```

FIG. 16F

```
2301 GTCCCGAGTG CTTGAGGATG ATCCGGAAGC AGCTTACACC ACCAGGGGTG
     CAGGGCTCAC GAACTCCTAC TAGGCCTTCG TCGAATGTGG TGGTCCCCAC
 768   SerArgVal LeuGluAspA spProGluAl aAlaTyrThr ThrArgGlyG
     GCAAGATTCC TATCCGGTGG ACTGCGCCAG AAGCAATTGC CTATCGTAAA
     CGTTCTAAGG ATAGGCCACC TGACGCGGTC TTCGTTAACG GATAGCATTT
     lyLysIlePr oIleArgTrp ThrAlaProG luAlaIleAl aTyrArgLys
2401 TTCACATCAG CAAGTGATGT ATGGAGCTAT GGAATCGTTA TGTGGGAAGT
     AAGTGTAGTC GTTCACTACA TACCTCGATA CCTTAGCAAT ACACCCTTCA
 801 PheThrSerA laSerAspVa lTrpSerTyr GlyIleValM etTrpGluVa
     GATGTCGTAC GGGGAGAGGC CCTATTGGGA TATGTCCAAT CAAGATGTGA
     CTACAGCATG CCCCTCTCCG GGATAACCCT ATACAGGTTA GTTCTACACT
     lMetSerTyr GlyGluArgP roTyrTrpAs pMetSerAsn GlnAspValIle
2501 TTAAAGCCAT TGAGGAAGGC TATCGGTTAC CCCCTCCAAT GGACTGCCCC
     AATTTCGGTA ACTCCTTCCG ATAGCCAATG GGGGAGGTTA CCTGACGGGG
 835    LysAlaIl eGluGluGly TyrArgLeuP roProProMe tAspCysPro
     ATTGCGCTCC ACCAGCTGAT GCTAGACTGC TGGCAGAAGG AGAGGAGCGA
     TAACGCGAGG TGGTCGACTA CGATCTGACG ACCGTCTTCC TCTCCTCGCT
     IleAlaLeuH isGlnLeuMe tLeuAspCys TrpGlnLysG luArgSerAsp
2601 CAGGCCTAAA TTTGGGCAGA TTGTCAACAT GTTGGACAAA CTCATCCGCA
     GTCCGGATTT AAACCCGTCT AACAGTTGTA CAACCTGTTT GAGTAGGCGT
 868   ArgProLys PheGlyGlnI leValAsnMe tLeuAspLys LeuIleArgA
     ACCCCAACAG CTTGAAGAGG ACAGGGACGG AGAGCTCCAG ACCTAACACT
     TGGGGTTGTC GAACTTCTCC TGTCCCTGCC TCTCGAGGTC TGGATTGTGA
     snProAsnSe rLeuLysArg ThrGlyThrG luSerSerAr gProAsnThr
```

FIG. 16G

```
2701 GCCTTGTTGG ATCCAAGCTC CCCTGAATTC TCTGCTGTGG TATCAGTGGG
     CGGAACAACC TAGGTTCGAG GGGACTTAAG AGACGACACC ATAGTCACCC
 901 AlaLeuLeuA spProSerSe rProGluPhe SerAlaValV alSerValGl
     CGATTGGCTC CAGGCCATTA AAATGGACCG GTATAAGGAT AACTTCACAG
     GCTAACCGAG GTCCGGTAAT TTTACCTGGC CATATTCCTA TTGAAGTGTC
     yAspTrpLeu GlnAlaIleL ysMetAspAr gTyrLysAsp AsnPheThrAla
2801 CTGCTGGTTA TACCACACTA GAGGCTGTGG TGCACGTGAA CCAGGAGGAC
     GACGACCAAT ATGGTGTGAT CTCCGACACC ACGTGCACTT GGTCCTCCTG
 935   AlaGlyTy rThrThrLeu GluAlaValV alHisValAs nGlnGluAsp
     CTGGCAAGAA TTGGTATCAC AGCCATCACA CACCAGAATA AGATTTTGAG
     GACCGTTCTT AACCATAGTG TCGGTAGTGT GTGGTCTTAT TCTAAAACTC
     LeuAlaArgI leGlyIleTh rAlaIleThr HisGlnAsnL ysIleLeuSer
2901 CAGTGTCCAG GCAATGCGAA CCCAAATGCA GCAGATGCAC GGCAGAATGG
     GTCACAGGTC CGTTACGCTT GGGTTTACGT CGTCTACGTG CCGTCTTACC
 968   SerValGln AlaMetArgT hrGlnMetGl nGlnMetHis GlyArgMetV
     TTCCCGTCTG AGCCAGTACT GAATAAACTC AAAACTCTTG AAATTAGTTT
     AAGGGCAGAC TCGGTCATGA CTTATTTGAG TTTTGAGAAC TTTAATCAAA
     alProValOp *AlaSerThr GluOc*ThrG lnAsnSerOp *AsnAm*Phe
3001 ACCTCATCCA TGCACTTTAA TTGAAGAACT GCACTTTTTT TACTTCGTCT
     TGGAGTAGGT ACGTGAAATT AACTTCTTGA CGTGAAAAAA ATGAAGCAGA
1001 ThrSerSerM etHisPheAs nOp*ArgThr AlaLeuPheL euLeuArgLe
     TCGCCCTCTG AAATTAAAGA AATGAAAAAA AAAAAACAAT ATCTGCAGCG
     AGCGGGAGAC TTTAATTTCT TTACTTTTTT TTTTTTGTTA TAGACGTCGC
     uArgProLeu LysLeuLysL ysOp*LysLy sLysAsnAsn IleCysSerVal
```

FIG. 16H

```
3101 TTGCTTGGTG CACAGATTGC TGAAACTGTG GGGCTTACAG AAATGACTGC
     AACGAACCAC GTGTCTAACG ACTTTGACAC CCCGAATGTC TTTACTGACG
1035    AlaTrpCy sThrAspCys Op*AsnCysG lyAlaTyrAr gAsnAspCys
        CGGTCATTTG AATGAGACCT GGAACAAATC GTTTCTCAGA AGTACTTTTC
        GCCAGTAAAC TTACTCTGGA CCTTGTTTAG CAAAGAGTCT TCATGAAAAG
        ArgSerPheG luOp*AspLe uGluGlnIle ValSerGlnL ysTyrPheSer
3201 TGTTCATCAC CAGTCTGTAA AATACATGTA CCTATAGAAA TAGAACACTG
     ACAAGTAGTG GTCAGACATT TTATGTACAT GGATATCTTT ATCTTGTGAC
1068    ValHisHis GlnSerValL ysTyrMetTy rLeuAm*Lys Am*AsnThrA
        CCTCTGAGTT TTGATGCTGT ATTTGCTGCC AGACACTGAG CTTCTGAGAC
        GGAGACTCAA AACTACGACA TAAACGACGG TCTGTGACTC GAAGACTCTG
        laSerGluPh eOp*CysCys IleCysCysG lnThrLeuSe rPheOp*Asp
3301 ATCCCTGATT CTCTCTCCAT TTGGAATTAC AACGGTCGAC GAGCTCGA
     TAGGGACTAA GAGAGAGGTA AACCTTAATG TTGCCAGCTG CTCGAGCT
1101  IleProAspS erLeuSerIl eTrpAsnTyr AsnGlyArgA rgAlaArg
``` under US 6,331,302 B1

PROTEIN TYROSINE KINASE AGONIST ANTIBODIES

This application is the U.S. National phase of PCT/US95/04228 filed Apr. 4, 1995 which is a continuation-in-part of U.S. Ser. No. 08/222,616 filed Apr. 4, 1994 (now U.S. Pat. No. 5,635,177) which is a continuation-in-part of PCT/US93/00586, filed Jan. 22, 1993 (which is National stage entry U.S. Ser. No. 08/256,769 filed Sep. 15, 1994), now abandoned which is a continuation-in-part of U.S. Ser. No. 07/826,935 filed Jan. 22, 1992 (now abandoned).

BACKGROUND OF THE INVENTION

1. Field of the Invention

The present invention relates to novel protein tyrosine kinase (pTK) genes, the proteins encoded by these genes, RNA nucleic acid sequences which hybridize to the genes, antibodies specific for the encoded proteins, chimeras of the proteins and methods of use therefor.

In particular, this application relates to agonist antibodies which are able to activate the tyrosine kinase domain of the receptor pTKs disclosed herein and pTK-immunoglobulin chimeras.

2. Description of Related Art

Transduction of signals that regulate cell growth and differentiation is regulated in part by phosphorylation of various cellular proteins. Protein tyrosine kinases are enzymes that catalyze this process. Moreover, many act as growth factor receptors. The c-kit subgroup of receptor tyrosine kinases catalyze the phosphorylation of exogenous substrates, as well as tyrosine residues within their own polypeptide chains (Ullrich et al., *Cell* 61:203 [1990]). Members of the c-kit subgroup include FLT/FLK (Fetal Liver Kinase), FGF (Fibroblast Growth Factor Receptor) and NGF (Nerve Growth Factor Receptor).

The EPH tyrosine kinase subfamily, Eph, Elk, Eck, Eek, Hek, Hek2, Sek, Ehk-1, Ehk-2, Cek-4 to -10, Tyro 1, 4, 5 and 6, appears to be the largest subfamily of transmembrane tyrosine kinases (Hirai et al., *Science* 238:1717–1720 [1987]; Letwin et al., *Oncogene* 3:621–678 [1988]; Lhotak et al., *Mol. Cell. Biol.* 13:7071–7079 [1993]; Lindberg et al., *Mol. Cell. Biol.* 10:6316–6324 [1990]; Bohme et al., *Oncogene* 8:2857–2862 [1993]; and Wicks et al., *Proc. Natl. Acad. Sci. USA.* 89:1611–1615 [1992]; Pasquale et al. *Cell Regulation* 2:523–534 [1991]; Sajjadi et al., *New Biol.* 3:769–778 [1991]; Wicks et al., *Proc. Natl. Acad. Sci. USA.* 89:1611–1615 [1992]; Lhotak et al., *Mol. Cell. Bio.* 11:2496–2502 [1991]; Gilardi-Hebenstreit et al., *Oncogene* 7:2499–2506 [1992]; Lai et al., *Neuron* 6:691–704 [1991]; Sajjadi et al., *Oncogene* 8:1807–1813 [1993]; and Maisonpierre et al., *Oncogene* 8:3277–3288 [1993]).

Additional pTKs and agonist antibodies thereto are needed in order to further study growth and differentiation of cells, for use as therapeutic agents and for diagnostic purposes. Accordingly, it is an object of the present invention to provide novel pTK genes, the proteins encoded thereby, antibodies specific for the encoded proteins, chimeras of the proteins and methods of use thereof.

SUMMARY OF THE INVENTION

The genes isolated as described herein are referred to, collectively, as "protein tyrosine kinase genes" or "pTK genes". The nucleic acid sequences of some of these genes, isolated as discussed herein, show significant homology with previously identified protein tyrosine kinases containing extracellular domains, which function as growth factor receptors (e.g., pTKs of the c-kit subgroup). Some of the pTK genes have been shown to be present in both megakaryocytic and lymphocytic cells.

In particular, fourteen pTK genes have been identified. Two pTK genes, referred to as SAL-S1 and SAL-D4 were identified in megakaryocytic cells. SAL-D4 is related to the CSK family of intracellular pTKs and SAL-S1 is related to the FGF receptor family of pTKs. Five pTK genes, referred to as LpTKs, were identified in lymphocytic cells and have been shown to be present in megakaryocytes as well. One pTK gene, referred to as HpTK5, was identified in human hepatoma cells. Six pTK genes, referred to as bpTK genes, were found in human brain tissue.

The pTK genes, which are the subject of the present invention, were generally identified using two sets of degenerative oligonucleotide primers: a first set which amplifies all pTK DNA segments (SEQ ID NOS: 1–2), and a second set which amplifies highly conserved sequences present in the catalytic domain of the c-kit subgroup of pTKs (SEQ ID NOS: 3–4). The pTK genes identified in this manner are described below.

SAL-S1 is expressed in several megakaryocytic cell lines, but not in erythroid cell lines. The nucleotide sequence of part of SAL-S1 was obtained, revealing a sequence containing 160 base pairs (SEQ ID NO: 5). This isolated DNA fragment encoded an amino acid sequence (SEQ ID NO: 6) which exhibited significant sequence homology with known protein tyrosine kinases of the FLT/FLK family. The deduced amino acid sequence of SAL-S1 (SEQ ID NO: 33) contains 1298 residues.

SAL-D4, also expressed in megakaryocytic cells, is a DNA fragment containing the nucleotide sequence of 147 base pairs. (SEQ ID NO: 7). This isolated DNA fragment encoded an amino acid sequence (SEQ ID NO: 8) which exhibited significant sequence homology with known protein tyrosine kinases of the CSK intracellular pTK family.

The LpTKs, including LpTK 2, LpTK 3, LpTK 4, LpTK 13 and LpTK 25, are expressed in lymphocytic cells, as well as megakaryocytic cells. The nucleotide sequence (151 base pairs) of the LpTK 3 gene was obtained (SEQ ID NO: 11). The nucleotide sequences of the LpTK 2, LPTK 4, and LpTK 13 genes contained 149 base pairs (SEQ ID NO: 9), 137 base pairs (SEQ ID NO: 13), and 211 base pairs (SEQ ID NO: 15) respectively. LpTK 25 has a nucleotide sequence of 3120 b.p. (SEQ ID NO: 22). A full length gene sequence has been obtained for LpTK 2 (SEQ ID NO: 19) which contains 7607 b.p. Additional sequencing of LpTK 4 revealed a sequence of 404 b.p. (SEQ ID NO: 21).

The HpTK5 gene, expressed in human hepatoma cells, has a nucleotide sequence of 3969 b.p. (SEQ ID NO: 23).

Nucleotide sequences of the bpTKs, including bpTK 1, bpTK 2, bpTK 3, bpTK 4, bpTK 5 and bpTK 7, are expressed in human brain tissue and encode proteins having the amino acid sequences of SEQ ID NOS: 25–29 and 34 respectively.

Thus, the present invention includes DNA isolated from a human megakaryocytic cell line, which hybridizes to DNA encoding an amino acid sequence which is highly conserved in the catalytic domain of protein tyrosine kinases of the c-kit subgroup.

The present invention also includes the proteins encoded by the pTK genes identified as described herein, which exhibit significant sequence homology with members of the c-kit subgroup of pTKs as well as the proteins encoded by HpTK5 and the bpTKs. The present invention also includes SAL-S1, SAL-D4, LpTK, HpTK5 and bpTK homologues or equivalents (i.e., proteins which have amino acid sequences substantially similar, but not identical, to that of SAL-S1, SAL-D4, the LpTKs, HpTK5 and the bpTKs, which exhibit tyrosine kinase activity). This invention further includes peptides (SAL-S1, SAL-D4, LpTK, HpTK5 and bpTK fragments) which retain tyrosine kinase activity, yet are less than the entire SAL-S1, SAL-D4, LpTK, HpTK5 and bpTK sequences; and uses for the SAL-S1, SAL-D4, the LpTK, HpTK and the bpTK nucleic acid sequences and SAL-S1, SAL-D4, LpTK, HpTK and bpTK equivalents.

The present invention further includes nucleic acid sequences which hybridize with DNA or RNA encoding the proteins described herein, which exhibit significant sequence homology with the FLT/FLK, FGF receptor or NGF receptor family of protein tyrosine kinases contained within the c-kit subgroup. Such nucleic acid sequences are useful as probes to identify pTK genes in other vertebrates, particularly mammals. and in other cell types. They can also be used as anti-sense oligonucleotides to inhibit protein tyrosine kinase activity, both in vitro and in vivo.

The SAL-S1, SAL-D4, LpTK, HpTK and bpTK tyrosine kinases of the present invention can be used as target proteins in conjunction with the development of drugs and therapeutics to modulate cell growth, differentiation and other metabolic functions. The SAL-S1, SAL-D4, LpTK, HpTK or bpTK proteins can be used as agonists or antagonists to other tyrosine kinases. The pTKs can also be instrumental in the modulation of megakaryocyte and/or platelet adhesion interactions.

In addition, the SAL-S1, SAL-D4, LpTK, HpTK and bpTK tyrosine kinases can be used in screening assays to detect cellular growth and/or differentiation factors. Using standard laboratory techniques, the ligands of the pTKs of the present invention can be identified. In particular, the invention provides chimeric pTK-immunoglobulin fusion proteins which are useful for isolating ligands to the pTKs disclosed herein. The chimeric proteins are also useful for diagnostic assays designed to detect these ligands present endogenously, within cells, as well as exogenously, in extracellular fluids. Assays, using the chimeric proteins, can also be designed as diagnostic aids to detect these ligands in body fluids such as blood and urine.

In another aspect, the invention provides antibodies specific for SAL-S1, SAL-D4, the LpTKs, HpTK5 and the bpTKs, which are optionally agonists for their respective pTK (where the pTK is a receptor). The invention also concerns a hybridoma cell line and an isolated nucleic acid encoding a monoclonal antibody as herein defined.

Also, the invention pertains to a method for activating a pTK as herein disclosed, comprising reacting the pTK with an agonist antibody thereto. In a different aspect, the invention concerns a method for enhancing cell growth and/or differentiation comprising administering to a human patient in need of such treatment a physiologically effective amount of an agonist antibody which activates a pTK as herein disclosed.

In a still further aspect, the invention concerns a method for detecting a pTK by contacting a source suspected of containing the pTK with a detectably labeled monoclonal antibody which reacts immunologically with the pTK, and determining whether the antibody binds to the source.

BRIEF DESCRIPTION OF THE DRAWINGS

FIGS. 1A and 1B depict the nucleotide sequence of SAL-S1 (SEQ ID NO: 5) and its deduced amino acid sequence (SEQ ID NO: 6).

FIGS. 2A and 2B depict the nucleotide sequence of SAL-D4 (SEQ ID NO: 7) and its deduced amino acid sequence (SEQ ID NO: 8).

FIG. 3A depicts the nucleotide sequence of LpTK 2 (SEQ ID NO: 9) and its deduced amino acid sequence (SEQ ID NO: 10).

FIG. 3B depicts the nucleotide sequence of LpTK 3 (SEQ ID NO: 11) and its deduced amino acid sequence (SEQ ID NO: 12).

FIG. 3C depicts the nucleotide sequence of LpTK 4 (SEQ ID NO: 13) and its deduced amino acid sequence (SEQ ID NO: 14).

FIG. 3D depicts the nucleotide sequence of LpTK 13 (SEQ ID NO: 15) and its deduced amino acid sequence (SEQ ID NO: 16).

FIGS. 4A–4I depict the nucleotide sequence (SEQ ID NO: 17) of SAL-S1 and its deduced amino acid sequence (SEQ ID NO: 18).

FIGS. 5A–5K depict the full length nucleotide sequence (SEQ ID NO: 19) of LpTK2 and its deduced amino acid sequence (SEQ ID NO: 20).

FIG. 6 depicts the partial nucleotide sequence (SEQ ID NO: 21) for LpTK4.

FIGS. 7A–7C depict the full length nucleotide sequence (SEQ ID NO: 22) for LpTK25.

FIGS. 8A–8I depict the full length nucleotide sequence (SEQ ID NO: 23) and the deduced amino acid sequence of HpTK5 (SEQ ID NO: 24).

FIG. 9 depicts the amino acid sequence (SEQ ID NO: 25) of bpTK1.

FIG. 10 depicts the amino acid sequence (SEQ ID NO: 26) of bpTK2.

FIG. 11 depicts the amino acid sequence (SEQ ID NO: 27) of bpTK3.

FIG. 12 depicts the amino acid sequence (SEQ ID NO: 28) of bpTK4.

FIG. 13 depicts the amino acid sequence (SEQ ID NO: 29) of bpTK5.

FIG. 14 depicts the amino acid sequence (SEQ ID NO: 30) of bpTK7.

FIGS. 15A–15F depict the full-length nucleotide sequence of SAL-S1 (SEQ ID NO: 31) to complement (SEQ ID NO 32) and its deduced amino acid sequence (SEQ ID NO: 33).

FIGS. 16A–16H depict the full-length nucleotide sequence of bpTK7 (SEQ ID NO: 34) to complement (SEQ ID NO: 35) and its deduced amino acid sequence (SEQ ID NO: 36).

DETAILED DESCRIPTION OF THE PREFERRED EMBODIMENTS

Novel protein tyrosine kinase genes have been identified, their nucleic acid sequences determined, and the amino acid sequences of the encoded proteins deduced. The genes isolated as described herein are referred to, collectively, as "protein tyrosine kinase genes" or "pTK genes".

To facilitate the isolation and identification of these novel pTKs, two sets of DNA probes were used, as described in Example 1. The first set generally consisted of two degenerative oligonucleotide sequences, pTK 1 (SEQ ID NO: 1) and pTK 2 (SEQ ID NO: 2) (Matthews, *Cell* 65:1143 [1991]; and Wilks, *Proc. Natl. Acad. Sci. USA* 86:1603 [1989]). These sequences were used as primers in a polymerase chain reaction to amplify tyrosine kinase DNA segments (Mullis, et al., *Cold Spring Harbor Symp. Advan. Biol.* 51:263 [1986]).

The second set generally consisted of two oligonucleotide sequences, pTK 3 (SEQ ID NO: 3) and pTKKW (SEQ ID NO: 4) designed to amplify the nucleic acid sequence which encodes the highly conserved regions of the catalytic domains of the c-kit family of protein tyrosine kinases. These sequences were used as primers in the polymerase chain reaction (PCR) in a second round of DNA amplification. Using this two-step amplification procedure, DNA fragments which hybridized to these pTK primers were identified, isolated and subsequently sequenced.

In particular, fourteen pTK genes have been identified. Two pTK genes, referred to as SAL-S1 and SAL-D4, were identified in several megakaryocytic cell lines, including CMK 11-5, DAMI, UT-7 and UT-7 grown in erythropoietin, but not in the erythroid cell lines HEL, PMA stimulated HEL cells, or K562. Five pTK genes, referred to as LpTKs, were identified in lymphocytic, as well as in megakaryocytic cells. One pTK gene, referred to as HpTK5, was identified in human hepatoma cells, and six genes, referred to as bpTKs, were identified in human brain tissue.

SAL-S1 (SEQ ID NOS: 6, 18 and 33) encoded by the nucleic acid sequence of SEQ ID NOS: 5, 17 and 31 exhibits significant homology with the FLT/FLK family of pTKs. SAL-S1 has a signal peptide (i.e., amino acid residues 1 to 24 of FIG. 15); extracellular domain (i.e., amino acid residues 25 to 775 of FIG. 15); transmembrane domain (i.e., amino acid residues 776 to 800 of FIG. 15) and a cytoplasmic tyrosine kinase domain (i.e., amino acid residues 801 to 1298 of FIG. 15). SAL-D4 (SEQ ID NO: 8) encoded by SEQ ID NO: 7 is related to the CSK family of intracellular pTKs. The LpTKs, LpTK 2 (SEQ ID NOS: 10 and 20) encoded by SEQ ID NOS: 9 and 19; LpTK 3 (SEQ ID NO: 12) encoded by SEQ ID NO: 11; LpTK4 (SEQ ID NO: 14) encoded by SEQ ID NOS: 13 and 21; LpTK13 (SEQ ID NO: 16) encoded by SEQ ID NO: 15; and LpTK25 encoded by SEQ ID NO: 22, also exhibit sequence homology with known protein tyrosine kinases.

HpTK5 (SEQ ID NO: 24) encoded by SEQ ID NO: 23 and the bpTKs 1, 2, 3, 4, 5 and 7 (SEQ ID NOS: 25–29 and 36 respectively), similarly exhibit sequence homology with known protein tyrosine kinases. BpTK7 encodes a receptor pTK with a signal peptide (i.e., amino acid residues 1–19 of FIG. 16); extracellular domain (i.e., amino acid residues 20–547 of FIG. 16); and transmembrane domain (i.e., amino acid residues 548–570 of FIG. 16). The remaining sequence comprises the intracellular tyrosine kinase domain.

Thus, as described above, DNA molecules which hybridize with DNA encoding amino acid sequences present in the catalytic domain of a protein tyrosine kinase of the c-kit subgroup of protein kinases have been isolated and sequenced. These isolated DNA sequences, collectively referred to as "pTK genes", (and their deduced amino acid sequences) have been shown to exhibit significant sequence homology with known members of pTK families.

Once isolated, these DNA fragments can be amplified using known standard techniques such as PCR. These amplified fragments can then be cloned into appropriate cloning vectors and their DNA sequences determined.

These DNA sequences can be excised from the cloning vectors, labeled with a radiolabeled nucleotide such as $^{32}P$ and used to screen appropriate cDNA libraries to obtain the full-length cDNA clone.

The pTK genes as described above have been isolated from the source in which they occur naturally, e.g., megakaryocytic and lymphocytic cells. The present invention is intended to include pTK genes produced using genetic engineering techniques, such as recombinant technology, as well as pTK genes that are synthesized chemically.

The deduced amino acid sequences of the pTK genes include amino acid sequences which encode peptides exhibiting significant homology with the catalytic domain of protein tyrosine kinases of the c-kit subgroup of tyrosine kinases. These proteins, encoded by the pTK genes, can include sequences in which functionally equivalent amino acid residues are substituted for residues within the sequence, resulting in a silent change, that is a change not detected phenotypically. For example, one or more amino acid residues within the sequence can be substituted by another amino acid of a similar polarity which acts as a functional equivalent, resulting in a silent substitution.

In addition, the protein structure can be modified by deletions, additions, inversion, insertions or substitutions of one or more amino acid residues in the sequence which do not substantially detract from the desired functional tyrosine kinase properties of the peptide.

Modified pTKs of the present invention, with tyrosine kinase activity, can be made using recombinant DNA techniques, such as excising it from a vector containing a cDNA encoding such a protein, or by synthesizing DNA encoding the desired protein mechanically and/or chemically using known techniques.

An alternate approach to producing the pTKs of the present invention is to use peptide synthesis to make a peptide or polypeptide having the amino acid sequence of such a protein, depending on the length of the pTK desired. The peptides or modified equivalents thereof, can be synthesized directly by standard solid or liquid phase chemistries for peptide synthesis.

Preferably, the pTKs of the present invention will be produced by inserting DNA encoding the proteins into an appropriate vector/host system where it will be expressed. The DNA sequences can be obtained from sources in which they occur naturally, can be chemically synthesized or can be produced using standard recombinant technology.

This invention also pertains to an expression vector comprising a pTK gene of the present invention, encoding for a protein which exhibits receptor tyrosine kinase activity.

The pTK genes of the present invention can be used for a number of diagnostic and therapeutic purposes. For example, the nucleic acid sequences of the pTK genes can be used as probes to identify other protein tyrosine kinases present in other cell types, including eukaryotic and prokaryotic cell types.

The nucleic acid sequences can also be used to design drugs that directly inhibit the kinase activity of protein tyrosine kinases, or to design peptides that bind to the catalytic domain of tyrosine kinases, thus inhibiting their activity. These sequences can also be used to design anti-sense nucleotides that can also inhibit, or destroy, tyrosine kinase activity. Such inhibition of tyrosine kinase activity would be desirable in pathological states where decreased cellular proliferation would be beneficial, such as leukemias or other malignancies.

The nucleic acid sequences can also be used to design drugs, peptides or anti-sense nucleotides as above, but with enhancing, rather than inhibitory effects, on tyrosine kinases. Such enhanced tyrosine kinase activity would result in increasing the phosphorylation of substrates (exogenous, as well as endogenous tyrosine residues). Enhanced effects would be desirable in states where increased cellular proliferation would be beneficial, such as anemias, bleeding disorders and during surgical procedures.

The pTK genes of the present invention can also be used to obtain soluble fragments of receptor tyrosine kinases, capable of binding their respective ligands. pTK genes encoding soluble tyrosine kinase fragments can be produced using recombinant DNA techniques or synthetically. In either case, the DNA obtained encodes a soluble pTK fragment which lacks a substantial portion of the hydrophobic transmembrane region to permit solubilization of the fragment.

These soluble pTK protein fragments can be introduced exogenously to act as competitors with the endogenous, membrane bound pTK for their respective ligands, thus inhibiting tyrosine kinase activity. Alternately, a modified soluble pTK protein fragment can be introduced which binds the ligand but does not activate kinase activity.

These soluble pTK protein fragments can also be used in binding assays to detect ligands such as growth and differentiation factors. Once these ligands are identified, they may be altered or modified to inhibit or enhance kinase activity. For example, the ligands may be modified or attached to substances that are toxic to the cell, such a ricin, thus destroying the target cell. The substance may be a superactivating substance which, after binding to the pTK, may substantially increase the kinase activity, or activate other growth factors.

pTK genes of the present invention would also be useful to develop diagnostic tools for in vitro screening assays for ligands such as growth factors or differentiation factors that inhibit or enhance kinase activity. The proteins encoded by the pTK genes can also be used in such assays, or as immunogens to produce monoclonal or polyclonal antibodies to be used in such assays.

In one embodiment of the invention, a chimera comprising a fusion of the extracellular domain of the pTK (where the pTK is a receptor) and an immunoglobulin constant domain can be constructed which can be used to assay for ligands for the receptor and can be used for the production of antibodies against the extracellular domain of the receptor.

The expression "extracellular domain" or "ECD" when used herein refers to any polypeptide sequence that shares a ligand binding function of the extracellular domain of the naturally occurring receptor pTKs disclosed herein. Ligand binding function of the extracellular domain refers to the ability of the polypeptide to bind at least one pTK ligand. Accordingly, it is not necessary to include the entire extracellular domain since smaller segments are commonly found to be adequate for ligand binding. The truncated extracellular domain is generally soluble. The term ECD encompasses polypeptide sequences in which the hydrophobic transmembrane sequence (and, optionally, 1–20 amino acids C-terminal and/or N-terminal to the transmembrane domain) of the mature pTK has been deleted. Thus, the soluble extracellular domain-containing polypeptide can comprise the extracellular domain and the cytoplasmic domain of the pTK. Alternatively, in the preferred embodiment, the polypeptide comprises only the extracellular domain of the pTK. The extracellular and transmembrane domains of the pTK can be readily determined by the skilled practitioner by aligning the pTK of interest with known pTK amino acid sequences for which these domains have been delineated. Alternatively, the hydrophobic transmembrane domain can be readily delineated based on a hydrophobicity plot of the sequence. The extracellular domain is N-terminal to the transmembrane domain.

The term "immunoglobulin" generally refers to polypeptides comprising a light or heavy chain usually both disulfide bonded in the native "Y" configuration, although other linkage between them, including tetramers or aggregates thereof, is within the scope hereof.

Immunoglobulins (Ig) and certain variants thereof are known and many have been prepared in recombinant cell culture. For example, see U.S. Pat. No. 4,745,055; EP 256,654; Faulkner et al., *Nature* 298:286 [1982]; EP 120, 694; EP 125,023; Morrison, *J. Immun.* 123:793 [1979]; Köhler et al., *Proc. Nat'l. Acad. Sci. USA* 77:2197 [1980]; Raso et al., *Cancer Res.* 41:2073 [1981]; Morrison et al., *Ann. Rev. Immunol.* 2:239 [1984]; Morrison, *Science* 229:1202 [1985]; Morrison et al., *Proc. Nat'l. Acad. Sci. USA* 81:6851 [1984]; EP 255,694; EP 266,663; and WO 88/03559. Reassorted immunoglobulin chains also are known. See for example U.S. Pat. No. 4,444,878; WO 88/03565; and EP 68,763 and references cited therein. The immunoglobulin moiety in the chimera of the present invention may be obtained from $IgG_1$, $IgG_2$, $IgG_3$, or $IgG_4$ subtypes, IgA, IgE, IgD or IgM, but preferably $IgG_1$ or $IgG_3$. Most preferably, the immunoglobulin moiety is the Fc portion of IgG-γ.

The terms "chimera comprising a fusion of an extracellular domain of a pTK with an immunoglobulin constant domain sequence" or "pTK-immunoglobulin chimera" refer to a polypeptide comprising an extracellular domain coding amino acid sequence of a pTK conjugated to an immunoglobulin constant domain sequence. This definition includes chimeras in monomeric, homo- or heteromultimeric, and particularly homo- or heterodimeric, or -tetrameric forms.

A preferred embodiment is the fusion of the C-terminus of the extracellular domain of a pTK, to the N-terminus of the C-terminal portion of an antibody (in particular the Fc domain), containing the effector functions of immunoglobulin $G_1$. In a preferred embodiment, the entire heavy chain constant region is fused to the extracellular domain. In another preferred embodiment, a sequence beginning in the hinge region just upstream of the papain cleavage site (which defines IgG Fc chemically; residue 216, taking the first residue of heavy chain constant region to be 114 (Kabat et al., *Sequences of Immunological Interest*, National Institutes of Health, Bethesda, Md., [1987]), or analogous sites of other immunoglobulins) is fused to the ECD of the pTK.

In a particularly preferred embodiment, the pTK extracellular domain is fused to the hinge region and $C_H2$ and $C_H3$ or $C_H1$, hinge, $C_H2$ and $C_H3$ domains of an $IgG_1$, $IgG_2$ or IgG3 heavy chain. The precise site at which the fusion is made is not critical, and the optimal site can be determined by routine experimentation. A principal advantage of the chimeras is that they are secreted into the culture medium of recombinant hosts, although the degree of secretion might be different for various expression systems.

In general, the chimeras of the present invention are constructed in a fashion similar to chimeric antibodies in which a variable domain from an antibody of one species is substituted for the variable domain of another species. See, for example, EP 0 125 023; EP 173,494; Munro, *Nature* 312: [Dec. 13, 1984]; Neuberger et al., *Nature* 312: [Dec. 13, 1984]; Sharon et al., *Nature* 309: [May 24, 1984]; Morrison et al., *Proc. Nat'l. Acad. Sci. USA* 81:6851–6855 [1984]; Morrison et al. *Science* 229:1202–1207 [1985]; Boulianne et al., *Nature* 312:643–646 [Dec. 13, 1984]; Capon et al., *Nature* 337, 525–531 [1989]; Traunecker et al., *Nature* 339, 68–70 [1989].

To prepare the pTK-Ig chimeric polypeptides, the DNA including a region encoding the desired pTK sequence is cleaved by a restriction enzyme at or proximal to the 3' end of the DNA encoding the immunoglobulin-like domain(s) and at a point at or near the DNA encoding the N-terminal end of the mature pTK (where use of a different leader is contemplated) or at or proximal to the N-terminal coding region for the pTK (where the native signal is employed). This DNA fragment then is readily inserted proximal to DNA encoding an immunoglobulin light or heavy chain constant region and, if necessary, the resulting construct tailored by deletional mutagenesis. Preferably, the Ig is a human immunoglobulin when the variant is intended for in vivo therapy for humans. DNA encoding immunoglobulin light or heavy chain constant regions is known or readily available from cDNA libraries or is synthesized. See for example, Adams et al., *Biochemistry* 19:2711–2719 [1980]; Gough et al., *Biochemistry* 19:2702–2710 [1980]; Dolby et al., *P.N.A.S. USA,* 77:6027–6031 [1980]; Rice et al., *P.N.A.S. USA* 79:7862–7865 [1982]; Falkner et al., *Nature* 298:286–288 [1982]; and Morrison et al., *Ann. Rev. Immunol.* 2:239–256 [1984].

The chimeric proteins disclosed herein are useful as diagnostics for isolating or screening ligands for the pTK of interest using the techniques of Lyman et al., *Cell* 75:1157–1167 [1993], for example. Also, the chimeric proteins are useful for diagnostic purposes for studying the interaction of various ligands with the extracellular domain of the various pTKs (see, e.g., Bennett et al., *J. Biol. Chem.* 266(34):23060–23067 [1991]). The chimeric proteins are further useful for the production of antibodies against the extracellular domain of the pTK (see Examples 3 and 5 herein). The chimeric proteins also have an additional therapeutic utility insofar as they provide a soluble form of the extracellular domain of the pTK which generally has an enhanced plasma half life (compared to the extracellular domain only) and therefore can be formulated in a pharmaceutically acceptable carrier and administered to a patient. The chimeric proteins are believed to find use as therapeutic agents for removal of excess systemic or tissue-localized pTK ligand which has been administered to a patient. Removal of excess ligand is particularly desirably where the ligand may be toxic to the patient. The chimeric protein acts to bind the ligand in competition with the endogenous pTK in the patient. Similarly, it is contemplated that the chimeric protein can be administered to a patient simultaneously, or subsequent to, administration of the ligand in the form of a sustained release composition. The chimeric protein acts as a soluble binding protein for the ligand, thereby extending the half-life of the ligand.

The term "antibody" is used herein in the broadest sense and specifically covers polyclonal antibodies, monoclonal antibodies, immunoglobulin chains or fragments thereof, which react immunologically with a pTK.

In the preferred embodiment of the invention, the antibodies are monoclonal antibodies produced using techniques which are well known in the art. For example, the hybridoma technique described originally by Kohler and Milstein, *Eur. J. Immunol.,* 6:511 [1976], and also described by Hammerling et al., In: *Monoclonal Antibodies and T-Cell Hybridomas,* Elsevier, N.Y., pp. 563–681 [1981] can be used. The techniques of Cote et al. and Boerner et al. are also available for the preparation of human monoclonal antibodies [Cote et al., *Monoclonal Antibodies and Cancer Therapy,* Alan R. Liss, p. 77 [1985] and Boerner et al., *J. Immunol.,* 147(1):86–95 [1991]).

The term "monoclonal antibody" as used herein refers to an antibody (as hereinabove defined) obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they can be synthesized by a hybridoma culture, uncontaminated by other immunoglobulins.

"Humanized" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal amino acid residues derived from a non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, a humanized antibody may comprise residues which are found neither in the recipient antibody nor in the imported CDR or framework sequences. These modifications are made to further refine and optimize antibody performance.

The monoclonal antibodies herein include hybrid (chimeric) and recombinant antibodies produced by splicing a variable (including hypervariable) domain of an anti-pTK antibody with a constant domain (e.g., "humanized" antibodies), only one of which is directed against a pTK, or a light chain with a heavy chain, or a chain from one species with a chain from another species, or fusions with heterologous proteins, regardless of species of origin or immunoglobulin class or subclass designation, so long as they are able to bind to the pTK of interest [See, e.g., Cabilly, et al., U.S. Pat. No. 4,816,567; and Mage & Lamoyi, in *Monoclonal Antibody Production Techniques and Applications,* pp. 79–97 (Marcel Dekker, Inc., New York [1987]).

For "chimeric" and "humanized" antibodies see, for example, U.S. Pat. No. 4,816,567; WO 91/09968; EP 452, 508; and WO 91/16927.

Thus, the modifier "monoclonal" indicates the character of the antibody as being obtained from a substantially homogeneous population of antibodies, and is not to be construed as requiring production of the antibody by any particular method.

In the most preferred embodiment of the invention, the antibodies are agonist antibodies. By "agonist antibody" is meant an antibody which is able to bind to, and activate, a particular pTK. For example, the agonist may bind to the extracellular domain of the pTK and thereby cause dimerization of the pTK, resulting in transphosphorylation and activation of the intracellular catalytic kinase domain. Consequently, this may result in stimulation of growth and/or differentiation of cells expressing the receptor in vitro and/or in vivo. The agonist antibodies herein are preferably against epitopes within the extracellular domain of the pTK, and preferably have the same biological characteristics as the monoclonal antibody produced by the hybridoma cell line deposited under American Type Culture Collection Accession No. ATCC HB 11,583. By "biological characteristics" is meant the in vitro and/or in vivo activities of the monoclonal antibody, e.g., ability to activate the kinase domain of a particular pTK, ability to stimulate cell growth and/or differentiation of cells expressing the pTK, and binding characteristics of the antibody, etc. Accordingly, the antibody preferably binds to substantially the same epitope as the anti-HpTK5 monoclonal antibody specifically disclosed herein. Most preferably, the antibody will also have substantially the same or greater antigen binding affinity of the anti-HpTK5 monoclonal antibody disclosed herein. To determine whether a monoclonal antibody has the same specificity as the anti-HpTK5 antibody specifically disclosed (i.e., the antibody having the ATCC deposit No. HB 11,583), one can, for example, use a competitive ELISA binding assay.

DNA encoding the monoclonal antibodies useful in the method of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells.

The agonist antibodies disclosed herein are useful for in vitro diagnostic assays for activating the pTK receptor of interest. This is useful in order to study the role of the receptor in cell growth and/or differentiation.

The pTK agonist antibodies have a further therapeutic utility in a method for enhancing cell growth and/or differentiation comprising administering to a human patient in need of such treatment a physiologically effective amount of an exogenous pTK agonist antibody. Agonist antibodies to the SAL-S1 pTK may find utility in treating bleeding disorders and anemias, since this pTK was found to be expressed in megakaryocytic cells. The bpTK agonist antibodies may similarly be used to enhance differentiation and/or proliferation of brain cells in neurodegenerative diseases (such as Alzheimers disease) based on the expression of these receptors in brain tissue. Finally, HpTK5 agonist antibodies may be used to enhance proliferation of primitive hematopoietic cells in patients having undergone chemo- or radiation therapy or bone marrow transplantation.

An "exogenous" therapeutic compound is defined herein to mean a therapeutic compound that is foreign to the mammalian patient, or homologous to a compound found in the mammalian patient but produced outside the mammalian patient.

The antibodies of the present invention are also suitable for detecting a pTK by contacting a source suspected to contain the pTK with a detectably labeled monoclonal antibody, and determining whether the antibody binds to the source. There are many different labels and methods of labeling known in the art. Suitable labels include, for example, enzymes, radioisotopes, fluorescent compounds, chemi- and bioluminescent compounds, paramagnetic isotopes. The pTK may be present in biological samples, such as biological fluids or tissues. For analytical or diagnostic purposes, the antibodies of the present invention are administered in an amount sufficient to enable the detection of a site on a pTK for which the monoclonal antibody is specific. The concentration of the detectably labeled monoclonal antibody should be sufficient to give a detectable signal above background, when bound to a pTK epitope.

The pTK agonist antibodies disclosed herein may be administered to a mammal, preferably a human, in a pharmaceutically acceptable dosage form, including those that may be administered to a human intravenously as a bolus or by continuous infusion over a period of time, by intramuscular, subcutaneous, intra-articular, intrasynovial, intrathecal, oral, topical, or inhalation routes.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/ml to 100 mg/ml.

Pharmaceutical compositions may be prepared and formulated in dosage forms by methods known in the art; for example, see Remington's Pharmaceutical Sciences, Mack Publishing Company, Easton, Pa., 15th Edition 1975.

An effective amount of the pTK agonist antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 1000 mg/kg or more, depending on the factors mentioned above. Typically, the clinician will administer the molecule until a dosage is reached that achieves the desired effect. The progress of this therapy is easily monitored by conventional assays.

Depending on the type and severity of the disease, from about 0.001 mg/kg to about 1000 mg/kg, more preferably about 0.01 mg to 100 mg/kg, more preferably about 0.010 to 20 mg/kg of the agonist antibody might be an initial candidate dosage for administration to the patient, whether, for example, by one or more separate administrations, or by continuous infusion. For repeated administrations over several days or longer, depending on the condition, the treatment is repeated until a desired suppression of disease symptoms occurs or the desired improvement in the patient's condition is achieved. However, other dosage regimens may also be useful.

The present invention will now be illustrated by the following Examples, which are not intended to be limiting in any way. The disclosures of all literature references cited in the specification are expressly incorporated herein by reference.

EXAMPLE 1

Identification and Isolation of pTK Genes

To facilitate the isolation and identification of these novel pTK genes, two sets of DNA probes were generally used (see Table 1).

The first set consisted of two degenerate oligonucleotide sequences, pTK 1 (SEQ ID NO: 1) and pTK 2 (SEQ ID NO: 2). These sequences were used as polymerase chain reaction (PCR) primers, using standard PCR techniques, to amplify tyrosine kinase DNA segments.

The second set consisted of two oligonucleotide sequences, pTK 3 (SEQ ID NO: 3) and pTKKW (SEQ ID NO: 4) selected from the highly conserved regions of the catalytic domains of the c-kit subgroup of protein tyrosine kinases. These sequences were also used as polymerase chain reaction primers in a second round of DNA amplification. Using this two-step amplification procedure, DNA fragments which hybridized to these pTK primers were identified, isolated and subsequently sequenced using known laboratory techniques.

(Schleicher & Schuell) digested with EcoR1 and BamH1, and subcloned into pUC19.

Recombinants were sequenced by the Sanger dideoxy method and evaluated by the FASTA nucleic acid sequence analysis program. One clone termed HpTK5 (214 bp) was radiolabelled by random priming and used to screen an oligo dT-primed lambda gt10 Hep3B cDNA library. DNA was isolated from 17 positive phage plaques and inserts were subcloned into the EcoR1 site of pBluescript (Stratagene La Jolla, Calif.). The largest insert, a 3969 bp cDNA, was sonicated to an average size of 800–2000 bp and cloned into the SmaI site of M13. Overlapping clones were sequenced using the Taq Dye Primer Cycle Method (CABI) on the Catalyst 800 Molecular Biology Lab Station (ABI). Sequencing reactions were then analyzed on the ABI 373A Automated DNA Sequenator.

TABLE 1

| Probe name | Sequence | |
|---|---|---|
| | First Round of Amplification | |
| pTK1 | 5'-CGGATCCACAGNGACCT-3' | (SEQ ID NO: 1) |
| PTK2 | 5'-GGAATTCCAAAGGACCAGACGTC-3' | (SEQ ID NO: 2) |
| | Second Round of Amplification | |
| pTK3 (kit family specific) | 5'-CGGATCCATCCACAGAGATGT-3' | (SEQ ID NO: 3) |
| pTKKW (kit family specific) | 5'-GGAATTCCTTCAGGAGCCATCCACTT-3' | (SEQ ID NO: 4) |

EXAMPLE 2

Isolation and Characterization of HpTK5

A. DNA Amplification and Cloning of HpTK5

Light density human bone marrow mononuclear cells, obtained from normal volunteers using Deaconess Hospital Institutional Review Board approved protocols and with voluntary written informed consent, were separated by anti-CD34 antibody (AMAC, Westbrook, Me.) and immunomagnetic beads (Dynal, Oslo, Norway). Flow cytometric analysis using FITC-conjugated anti-CD34 antibody (AMAC) confirmed ~95% CD34 positivity of isolated cells. The hepatoma cell line, Hep3B, was cultured in alpha medium (Gibco, Grand Island, N.Y.) supplemented with penicillin (100 U/mL), streptomycin (100 µg/mL) and 10% fetal bovine serum (Gibco) at 37° C. in a 5% $CO_2$ incubator. Total RNA extracted from CD34+ bone marrow mononuclear or Hep3B cells was reverse transcribed with random primers and the Moloney murine leukemia virus reverse transcriptase (RT) following the conditions of the manufacturer (Gibco-BRL) in a 20 µl reaction. PCR was performed on the RT reaction product in a 100 µl reaction containing 50 mM KCl, 10 mM Tris-HCl (pH 8.4), 1.5 mM MgCl, 20 µg/ml gelatin, 0.2 mM dNTPs, 2.5 units Taq polymerase (Perkin-Elmer/Cetus) and 50 pmol each of pTK-specific degenerate primers [pTK1 5'TCGGATCCACA/CGNGAC/TC/TTGGC 3' (SEQ ID NO. 37), pTK1B 5'TCGGATCCAC/TC/AGNGAC/TC/TTNGCNGC 3' (SEQ ID NO. 38), pTK2 5'CTCGAATTCCA/GA/TAA/GC/GT/ACCAG/CACA/GTC 3' (SEQ ID NO. 39), pTK2B 5'CTCGAATTCCA/GA/TAT/CC/GT/ACCAT/AACA/GTC 3' (SEQ ID NO. 40)] derived from consensus regions among known pTKs as previously reported by others (Hanks et al., *Science*, 241:42–52 [1988]; Wilks, *Proc. Nat. Acad. Sci., USA* 86:1603–1607 [1989]; and Matthews et al., *Cell* 65:1143–1152 [1991]). The PCR cycle was 1.5 min at 95° C., 2 min at 37° C. and 3 min at 63° C. repeated 35 times. The reaction product was electrophoretically separated on a 2% low-melting agarose gel, purified on an Elutip-D column A single full-length 3969 bp cDNA was isolated and sequenced. (FIGS. 8A–8F). The full length clone, named hepatoma transmembrane kinase (HTK) or HpTK5, included an open reading frame extending from nucleotide 90 to 3050 predicted to encode a 987 amino acid protein of 108,270 Dalton. The putative initiation codon is preceded by an in-frame stop codon beginning at base 78. Preceding the open reading frame is a 5' untranslated region which is GC-rich as is characteristic for many growth factors or growth factor receptors (Kozak, *J. Cell Biol.* 115:887–903 [1991]).

The predicted protein sequence includes a transmembrane region (aa 538–563) which divides HpTK5 into extracellular (ECD) and intracellular domains (ICD). The ECD of 538 amino acids includes a signal peptide of 15 amino acids and a cysteine-rich box containing 20 Cys residues. In addition, there are two fibronectin type III repeats spanning aa 321 to 425 and 435 to 526. Asn at positions 208, 340 and 431 are possible sites for N-glycosylation.

The putative intracellular domain (ICD) contains a kinase consensus region from position 613 through 881. This kinase region includes a putative ATP-binding consensus (Gly-X-Gly-X-X-Gly) in subdomain I at positions 622–627. A Lys at position 647 (subdomain II) corresponds to an invariant Lys among tyrosine kinases thought to be critical for the phosphotransfer reaction. Signature regions indicative of substrate specificity suggest that HpTK5 is a tyrosine rather than a serine/threonine kinase. These include the sequence at positions 740–745 in subdomain VI and the sequence at positions 783–790 in subdomain VIII. Tyrosine residues at positions 601, 619 and 741 are possible substrates for tyrosine kinase activity.

The predicted amino acid sequence of HpTK5 most closely resembles that of the subfamily originally defined by EPH. The pattern of expression of the EPH subfamily is suggestive of a role in differentiation and development. In particular, the emergence of neural elements corresponds with the expression of certain EPH-related genes. The EPH family receptors, Hek2 and Elk, are the most closely related pTKs to HpTK5. They share 79.3 and 76.5% identity within the ICD respectively and 45 and 42% identity within the ECD respectively.

B. Chromosome Mapping of HpTK5

Somatic cell hybrid DNAs from a panel of 25 human-hamster cell lines (Bios, New Haven, Conn.) were used for chromosome localization by PCR. Two sets of primers from the 3' untranslated region of HpTK5 were chosen. PCR was performed with 250 ng DNA and 50 pmol each of the 5' and 3' primers, 50 mM KCl, 1.5 mM $MgCl_2$, 20 μg/ml gelatin, 0.2 mM dNTPs and 2.5 units Taq polymerase in a final volume of 100 μl. Cycles of 94° C. for 30 sec, 60° C. for 30 sec and 72° C. for 30 sec were repeated 30 times. A portion of each sample (15 μl) was electrophoresed through a 1.5% agarose gel, transferred to a nylon membrane and hybridized to a $^{32}$P-labelled full length HpTK5 cDNA probe prior to 5 hour autoradiography. Positives were scored and compared to a matrix summary of human chromosomal material present in each of the somatic cell hybrid DNAs.

The 3'-untranslated region characteristically contains few, if any, intervening sequences and has a high degree of diversity among members of gene families making it preferred in this type of analysis. Both sets of primers gave results that were consistent with human chromosome 7 only. Human chromosome 7 also includes the genes for the EGF receptor, hepatocyte growth factor (HGF) receptor, HGF, platelet-derived growth factor (PDGF) and interleukin-6. Karyotypic abnormalities involving this chromosome are common among human leukemias, particularly in aggressive myeloid leukemias that occur following radiation, alkylating agent chemotherapy or a pre-existing myelodysplastic condition (Baer et al., *Curr. Opin. Oncol.* 4:24–32 [1992]).

C. Northern Blotting of HpTK5

Poly-A selected RNA was electrophoresed through a 1.2% agarose, 2.2M formaldehyde gel and transferred to a nylon filter. Prepared or commercially obtained filters were hybridized in 50% formamide at 42° C. to $^{32}$-P labeled HpTK5, glyceraldehyde-3-phosphate dehydrogenase (GAPDH) or actin cDNA inserts and washed under stringent conditions (final wash: 0.1×SSC, 0.2% SDS at 65° C.). SSC is 0.15 M NaCl/0.015M $Na_3$citrate, pH 7.6. Northern blots of human fetal or adult tissue RNA were obtained from Clontech (Palo Alto, Calif.) and contained 2 μg/lane of poly A selected RNA.

Northern blot analysis of human fetal tissues revealed a single transcript of ~4 Kb in heart, lung, liver and kidney, with a lesser signal detectable in brain. In adult human tissue, no signal was detectable in brain, while placenta had a particularly intense signal followed by kidney, liver, lung and pancreas. Skeletal muscle and heart were of lower signal intensity.

HpTK5 expression in human tumor cell lines was also analyzed by Northern blot analysis performed as discussed above. Cell lines derived from liver, breast (MCF 7), colon (Colo 205), lung (NCI 69), melanocyte (HM-1) or cervix (HeLa) had detectable signal of appropriate size. Message was present in select cell lines of hematopoietic origin. K562 (a primitive myeloid cell with multipotential), THP-1 (a monocytoid cell), U937 (a myelomonocytic cell line), Hep3B (a human hepatocarcinoma cell line), and CMK (of megakaryocytic origin) were all positive for HpTK5 message, but lymphoid (H9, Jurkat, JH-1, Raji, Ramos) or select other myeloid cells (KG-1 or KMT2) had no detectable transcript by Northern analysis.

Differential expression of the HpTK5 transcript in fetal versus adult brain suggests that HpTK5 may share, with other EPH subfamily members, a role in events related to neural development. However, unlike some members of the EPH subfamily which are exclusively expressed in neurons (Maisonpierre et al., supra), HpTK5 is widely expressed in other tissues. In particular, HpTK5 is expressed in hematopoietic cells including CD34+ hematopoietic progenitor cells. The presence of the HpTK5 message in early hematopoietic cells and cell lines of myeloid lineage, but not in cell lines derived from lymphoid cells, suggests that HpTK5 may have lineage restricted expression.

EXAMPLE 3

Production of Polyclonal Antibodies to HpTK5

An HpTK5 extracellular domain (ECD)-human $IgG_1$ Fc fusion gene was constructed and fusion protein produced as previously described (Bennett et al., *J. Biol. Chem.* 266:23060–23067 [1991]). Polyclonal antibodies were generated in New Zealand White rabbits against the fusion protein; 4 μg in 100 μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.* 93:3–12 [1983]). For subsequent boosts, the protein was injected into subcutaneous and intramuscular sites. 1.3 μg protein/kg body weight was injected every 3 weeks with bleeds taken 1 and 2 weeks following each boost. HpTK5 specificity of the immunized rabbit serum was assessed by flow cytometric analysis of NIH3T3 cells transfected with full length HpTK5 or vector alone using a 1:200 dilution of pre-immune serum or anti-HpTK5-IgG Fc serum. Significant peak shifts were observed in several HpTK5 expressing clones as compared to either pre-immune serum or vector alone transfectant controls.

EXAMPLE 4

Utility and Agonist Activity of Polyclonal Antibodies to HPTK5

A. FLAG-HpTK5 Fusion Construct

Overlapping oligonucleotides encoding a 12 amino acid peptide having the sequence MDYKDDDDKKLAM (SEQ ID NO: 41) which includes the 4 amino acid antibody recognition site "FLAG" (IBI, New Haven, Conn.) a 5'-EcoRV restriction site and a 3'-NcoI restriction site (5'-CCGGATATCATGGACTACAAGGACGAC-GATGACAAGAAGCTTGCCATGGAGCTC; SEQ ID NO: 42), were ligated into the NcoI site (base 88) of HpTK5 in the EcoRV digested Bluescript (Stratagene, La Jolla, Calif.) vector.

B. In vitro Transcription and Translation

Transcription was performed on 2 pmol of linearized HpTK5 or FLAG-HpTK5 containing plasmid at 37° C. for 1 h in 50 μl volume containing 10 mM dithiothreitol, 2.5 μg bovine serum albumin, 0.25 mM each dNTP, 0.5 M m7GRNA cap (New England Biolabs, Beverly, Mass.), 2.5 units RNasin (Promega, Madison, Wis.), 3 units T3 RNA polymerase (Pharmacia, Piscataway, N.J.). 1 μg of DNAase (New England Biolabs, Beverly Mass.) was added for 15 min at 37° C. prior to phenol/chloroform extraction and ethanol precipitation. Translation was performed using the Promega rabbit reticulocyte lysate kit according to the manufacturer's specifications with or without $^{35}$S-methionine (350 μCi) labeling. Sample buffer containing SDS and beta-mercaptoethanol (2-ME) was added before boiling and 10% SDS-PAGE.

C. HpTK5 Expression in NIH3T3 Cells

A 4038 bp Cla1-Xba1 cDNA fragment containing 32 bp of linker sequence, 37 bp of pBluescript (Stratagene La Jolla, Calif.) polylinker and the entire 3969 bp HpTK5 cDNA was subcloned into the expression vector pRIS (Genentech, Inc.) under the control of the Rous sarcoma virus LTR promoter. NIH3T3 cells maintained in high glucose Dulbecco's Modified Eagle's Medium (DMEM) supplemented with 10% FCS were co-transfected with pRIS-HpTK5 and pNeo (an SV40 based vector containing the neomycin resistance marker) by the calcium phosphate method as described by Gorman et al., in *DNA Prot. Engineer. Tech.* 2:3–10 [1990]. Neomycin resistant colonies were selected 48 hours after transfection with Geneticin (Gibco/BRL) at 400 µg/ml. Fourteen days later individual resistant colonies were isolated, expanded and analyzed by flow cytometry for HpTK5 expression using rabbit polyclonal antiserum.

D. Immunoprecioitation

Cells (Hep3B, control NIH3T3 or HpTK5 transfected NIH3T3) or in vitro translated protein (HpTK5 or FLAG-HpTK5) were used for immunoprecipitation with either serum (pre-immune or anti-HpTK5-IgG Fc) or monoclonal antibody (FLAG-specific, M2, or isotype control) (IBI, Rochester, N.Y.). Subconfluent cells were labeled with 200 µCi/ml $^{35}$S-methionione for 18 hours and lysed in lysis buffer (150 mM NaCl, 50M Tris-HCl pH8.0, 1 mM EDTA, 0.025 Na azide, 1% NP-40, 0.1% SDS, 10% Glycerol, 0.5% Na deoxycholate, 1 mM phenylmethylsulfonyl fluoride (PMSF), 10 µg/ml aprotinin, 10 µg/ml leupeptin and 50 µM Na vanadate) for 30 min on ice. The cell lysate was centrifuged (12,000×g) for 10 min at 4° C. Cell lysate supernatant or in vitro translation mixture was precleared with 0.05 volume of normal rabbit serum and adsorbed with 0.05 volume of Staphylococcus aureus protein-A Sepharose CL4B. After centrifugation, preimmune or immune serum (1:100 dilution), or monoclonal antibody, was added and rocked overnight at 4° C. before 100 µl of protein-A Sepharose CL4B was added and the solution rocked 4° C. for additional 2 h. Immunoprecipitates were washed, suspended in SDS/PAGE loading buffer (109 glycerol, 5% 2-ME, 2.3% SDS and 62.5 mM Tris-HCl pH 6.8), heated to 95° C. for 5 min and analyzed by 7.5% SDS-PAGE.

E. Cell Fractionation

Cell fractionation of Hep3B cells was performed to confirm the membrane localization of HpTK5 predicted by its amino acid sequence. Hep-3B cells (1 ×10$^7$) were labeled with 200 µCi/ml $^{35}$S-methionine in alpha MEM medium containing 10% dialyzed FCS overnight. The cells were washed twice with cold PBS, scraped into 1 ml of cold buffer (20 mM Tris-HCl pH 7.5, 2 mM EDTA, 5 mM EGTA, 0.25M sucrose, 0.01% leupeptin, 4 mM PMSF, 10 mM 2-ME) and disrupted by sonication for 40 seconds. Whole homogenates were centrifuged at 12,000×g for 15 min, the nuclear pellets isolated and the decanted supernatant centrifuged at 140,000×g for 40 min at 4° C. to pellet membranes. The resultant supernatant served as the cytosolic (C) fraction. Nuclear (N) and membrane (M) fractions were washed and dissolved in buffer containing 0.5% NP-40 prior to immunoprecipitation. The C, N or M fractions were immunoprecipitated with an anti-HpTK5 or pre-immune (control) serum, subjected to 12% SDS-PAGE and autoradiographed. HpTK5 segregated predominantly with the membrane fraction, though immunoprecipitated material was evident to a lesser extent in cytosol.

F. Protein Kinase Assay

Immunoprecipitates were washed once with kinase buffer (25 mM Hepes H7.4, 1 mM DTT, 10 mM MgCl, 10 mM MnCl), and resuspended in 40 µl of kinase buffer containing either unlabeled ATP or 10 µCi of $^{32}$P-ATP (3000 Ci/mM). After a 10 min incubation at 30° C., the reaction was stopped by adding 40 µl of 2×sample buffer and boiling the samples for 3 min prior to electrophoresis on 8.09% SDS-PAGE gel. The dried gel was covered with 4 sheets of aluminum foil to block $^{35}$S-labelled protein autoradiography and the gel was placed under film for 5 hours to overnight.

G. Western Blotting and Phosphotyrosine Assay

Proteins were electrophoretically transferred to a 0.2 µm nitrocellulose (Bio-Rad) or a 0.45 µm polyvinylidene diflouride (Millipore) membrane in a buffer containing 25 mM Tris-HCl (pH 7.5), 192 mM glycine and 20% methanol at 100 mA for 2 h. Filters were washed in TBS (10 mM Tris-HCl pH 8.0, 150 mM NaCl) blocked by incubating in TBST (TBS with 0.05% Tween-20) plus 5% BSA overnight. Filters were washed four times for 5 min each in TEST and incubated for 2 h with 4G10 anti-phosphotyrosine antibody from UBI (1:1000 dilution in TBST). Filters were washed four times for 5 min each in TBST and incubated for 1 h with the alkaline phosphatase labelled anti-mouse secondary antibody (Promega) at a 1:7500 dilution in TBST. After washing four times, the blot was developed for 30–60 min in AP buffer (100 mM Tris-HCl, 100 mM NaCl, 5 mM MgCl$_2$) plus BCIP, NBT substrates.

H. Antibody Induced Phosphorylation Assay

Rabbit antisera to HpTK5-IgG Fc were tested for their ability to induce HpTK5 phosphorylation in HPTK5 transfected NIH3T3 cells. Cells were plated at a density of 5×10$^5$ cells/well in a 6-well plate and, after 24 hours, were serum starved for 1 hour prior to adding pre-immune or immune serum at a 1:50 dilution for 30 minutes. Cells were then washed in PBS and lysed in either 2×sample buffer or NP-40 lysis buffer as described above. Either crude lysates or immunoprecipitated cell lysates were then separated via 4–12% gradient SDS-PAGE and analyzed by anti-phosphotyrosine immunoblot as described above. HpTK5 expressing cells were exposed to antisera and separated by SDS-PAGE either with or without immunoprecipitation. The electrotransferred gel was immunoblotted with anti-phosphotyrosine antibody. Enhanced tyrosine phosphorylation of HpTK5 was observed following exposure to polyclonal antiserum showing an agonist-like effect of antibody binding. Interaction of HpTK5 with an antibody directed against its ECD induces phosphorylation. This provides further support that HpTK5 may serve as a receptor for a ligand that triggers kinase activation. Details of the signaling pathway of HpTK5 may be further explored using antisera as a surrogate ligand.

I. Conclusions

An HpTK5 ECD-IgG Fc fusion protein was expressed, purified and used to generate rabbit anti-serum which immunoprecipitated a 120 kD protein from Hep3B cells. The specificity of the antiserum was confirmed by immunoprecipitation of in vitro translated HpTK5 RNA and HpTK5 transfected NIH3T3 cells. To determine the functional capacity of HpTK5, in vitro translated HpTK5 was immunoprecipitated, exposed to kinase conditions and immunoblotted using a phosphotyrosine specific monoclonal antibody. The data obtained indicated that HpTK5 is phosphorylated on tyrosine. However, the presence of other bands consistently appearing in the $^{32}$P-labelled immunoprecipitation suggested that HpTK5 protein was only partially purified and therefore, it could not be concluded that HpTK5 was enzymatically active. To overcome this problem, a fusion construct was generated in which an 8 amino acid epitope (FLAG) was added to the N-terminus of HpTK5. The FLAG-HpTK5 fusion was in vitro translated and immunoprecipitated with a FLAG-specific monoclonal antibody resulting in a single protein of appropriate size (~120 kD). When subjected to kinase conditions in the presence of $^{32}$P-ATP, the HpTK5-FLAG fusion protein was labelled on tyrosine confirming tyrosine autophosphorylation and thereby, the kinase function of HpTK5.

EXAMPLE 5

Production of Monoclonal Antibodies to HpTK5

Anti-HpTK5 monoclonal antibodies were produced by hyperimmunizing BALB/c mice intraperitoneally with the HpTK5 extracellular domain (ECD)-human IgG$_1$ Fc fusion protein (produced using the techniques disclosed above) in RIBI adjuvant (RIBI ImmunoChem Research, Hamilton, Mont.) and fusing splenocytes with the mouse myeloma cell line X63-Ag8.653 (Kearney et al., *J. Immunol.* 123:1548–1550 [1979]). The antibodies were purified from ascites fluid using protein A-Sepharose (Repligen Corp., Cambridge, Mass.) and established affinity chromatography methods (Goding, J. W., *J. Immunol. Methods* 20:241–253 [1978]).

Monoclonal antibodies were screened for their ability to bind the HpTK5 antigen. Starting on day 15 post fusion, culture supernatants were harvested from the fusion plates and assayed for their ability to specifically "capture" HpTK5-IgG. In this ELISA assay, goat anti-mouse IgG was coated onto 96 well microtiter plates. The culture supernatants (100 µl) were added to the wells and the mouse IgG present was bound by the goat anti-mouse IgG antibodies. The plates were washed and either HpTK5-IgG or CD4-IgG (100 µl at 6 nM) was added. The "captured" immunoadhesin was detected using a goat anti-hu (Fc specific) horseradish peroxidase conjugate and orthophenylene diamine substrate. Quantitation of substrate catalysis was determined by optical density at 490 nm.

Agonist antibodies were then screened for using the techniques disclosed in Example 6 below. Two agonist monoclonal antibodies were identified, one of which has been deposited with the ATCC.

EXAMPLE 6

Agonist Activity of Monoclonal Antibodies to HpTK5

The monoclonal antibodies produced using the techniques disclosed in Example 5 were tested for their ability to induce HpTK5 phosphorylation in HpTK5 transfected NIH3T3 cells. Cells were plated at a density of 5×10$^5$ cells/well in a 6-well plate and, after 24 hours, were serum starved for 1 hour prior to adding pre-immune serum or anti-HpTK5 monoclonal antibody (undiluted conditioned hybridoma media was used) for 30 minutes. Cells were then washed in PBS and lysed in either 2×sample buffer or NP-40 lysis buffer as described above. Either crude lysates or immunoprecipitated cell lysates were then separated via 4–12% gradient SDS-PAGE and analyzed by anti-phosphotyrosine immunoblot as described above. HpTK5 expressing cells were exposed to the monoclonal antibody and separated by SDS-PAGE either with or without immunoprecipitation. The electrotransferred gel was immunoblotted with anti-phosphotyrosine antibody. Enhanced tyrosine phosphorylation of HpTK5 was observed following exposure to monoclonal antibodies showing an agonist-like effect of antibody binding. Accordingly, interaction of HpTK5 with a monoclonal antibody directed against its ECD is able to induce phosphorylation of the kinase domain thereof.

EXAMPLE 7

Production of Polyclonal Antibodies to Sal-S1

A SAL-S1 extracellular domain (ECD)-human IgG$_1$ Fc fusion gene was constructed and fusion protein produced as previously described in Bennett et al., *J. Biol. Chem.* 26:23060–23067 [1991]. Briefly, PCR primers otk 1.41.1 (SEQ ID NO: 43) and otk 1.41.2 (SEQ ID NO: 44) were employed in the PCR technique using plasmid pRK5.tk1-1.1 (SEQ ID NO: 45) containing SAL-S1 nucleic acid as a template to create a DNA fragment which, when digested with SalI/BstEII, generated an 155bp SalI/BstEII fragment. This 155 bp fragment was combined with a 6839 bp SalI/HindIII fragment isolated from pRK5.tk1-1.1 and a 719 bp BstEII/HindIII fragment isolated from pBSSK-CH2-CH3 (Bennett et al., supra). These fragments were ligated together to create a plasmid pRK5.tk1.ig1.1 (7713 bp in size) which, when transfected into 293 cells, was used to produce a SAL-S1 extracellular domain (ECD)-human IgG Fc fusion protein. Fusion protein was prepared and purified as described in Bennett et al., supra. Polyclonal antibodies were generated in female New Zealand White rabbits against the fusion protein. Briefly, 12.5 µg of fusion protein in 0.625 ml PBS was emulsified with 0.625 ml Freund's adjuvant (complete adjuvant for the primary injection and incomplete adjuvant for all boosts). The primary injection and all boosts were intramuscular at two sites and subcutaneous at multiple sites. Boosts were carried out at 3 week intervals with bleeds taken 1 and 2 weeks following each boost. SAL-S1 specificity of the immunized rabbit serum was assessed by flow cytometric analysis of 293 (ATCC CRL 1593) and COS7 (ATCC CRL 1651) cells transfected with full length SAL-S1 or vector alone (see below) using a 1:200 dilution of pre-immune serum or anti-SAL-S1-IgG Fc serum. Significant peak shifts were observed in several SAL-S1 expressing clones as compared to either pre-immune serum or vector alone transfectant controls.

EXAMPLE 8

Utility and Agonist Activity of Sal-S1 Polyclonal Antibodies

A. Immunoprecipitation

Control 293 and COS7 cells as well as SAL-S1 transfected 293 and COS7 cells were used for immunoprecipitation with either pre-immune serum or anti-SAL-S1-IgG Fc polyclonal antibody. COS7 and 293 cells were transfected using a CaPO$_4$ procedure as described by Gorman, C. *DNA Cloning*, Glover D. Ed., IRL Press, Oxford, vol2: 143–190 (1985). For transient expression, 293 cells were transfected as described by Gearing et al. *EMBO* 8: 3667–3676 (1989). Subconfluent cells were labeled with 200 µCi/ml $^{35}$S-methionine for 18 hours and lysed in lysis buffer (150 mM NaCl, 50 mM HEPES, pH 7.5, 1 mM EGTA, 0.025 Na azide, 1% Triton-X 100, 1.5 mM MgCl$_2$, 10% Glycerol, 1 mM phenylmethylsulfonyl flouride [PMSF], 10 µg/ml aprotinin, 10 µg/ml leupeptin and 50 µM Na vanadate) for 10 min on ice. The cell lysate was centrifuged (12,000×g) for 10 min at 4° C. After centrifugation, preimmune or polyclonal antibody was added to the supernatant and rocked for 4 hrs at 4° C. before 100 µl of protein-A Sepharose CL4B was added and the solution rocked 4° C. for additional 2 h. Immunoprecipitates were washed, suspended in SDS/PAGE loading buffer (10% glycerol, 5% 2-ME, 2.3% SDS and 62.5 mM Tris-HCl pH 6.8), heated to 95° C. for 5 min and analyzed by 7.5% SDS-PAGE.

B. Western Blotting and Phosphotyrosine Assay

Proteins were electrophoretically transferred to a 0.2 μm nitrocellulose (Bio-Rad) or a 0.45 μm polyvinylidene diflouride (Millipore) membrane in a buffer containing 25 mM Tris-HCl (pH 7.5), 192 mM glycine and 20% methanol at 100 mA for 2 h. Filters were washed in TBS (10 mM Tris-HCl pH 8.0, 150 mM NaCl) blocked by incubating in TBST (TBS with 0.05% Tween-20) plus 5% BSA overnight. Filters were washed four times for 5 min each in TBST and incubated for 2 h with 4G10 anti-phosphotyrosine antibody from UBI (1:1000 dilution in TBST). Filters were washed four times for 5 min each in TBST and incubated for 1 h with the alkaline phosphatase labelled anti-mouse secondary antibody (Promega) at a 1:5000 dilution in TBST. After washing four times, the blot was developed for 30–60 min in AP buffer (100 mM Tris-HCl, 100 mM NaCl, 5 mM $MgCl_2$) plus BCIP, NBT substrates.

C. Antibody Induced Phosphorylation Assay

Rabbit antisera to SAL-S1-IgG Fc were tested for their ability to induce SAL-S1 phosphorylation in SAL-S1 transfected 293 cells. Cells were plated at a density of $5\times10^5$ cells/well in a 6-well plate and, after 24 hours, were serum starved for 12 hours prior to adding pre-immune or immune serum at a 1:5 dilution for 30 minutes. Cells were then washed in PBS and lysed in either sample buffer or Triton-X lysis buffer as described above. Either crude lysates or immunoprecipitated cell lysates were then separated via 8% or 4–12% gradient SDS-PAGE and analyzed by anti-phosphotyrosine immunoblot as described above. SAL-S1 expressing cells were exposed to antisera and separated by SDS-PAGE either with or without immunoprecipitation. The electrotransferred gel was immunoblotted with anti-phosphotyrosine antibody. Enhanced tyrosine phosphorylation of SAL-S1 was observed following exposure to polyclonal antiserum showing an agonist-like effect of antibody binding. Interaction of SAL-S1 with an antibody directed against its ECD induces phosphorylation.

EXAMPLE 9

Production of Monoclonal Antibodies to Sal-S1

Anti-SAL-S1 monoclonal antibodies were produced by hyperimmunizing BALB/c mice in the foot pad with the SAL-S1 extracellular domain-human $IgG_1$ Fc fusion protein in RIBI adjuvant (RIBI Immunochem Research, Hamilton, Mont.) and fusing lymphocyte from lymph nodes with the mouse myeloma cell line X63-Ag8U1.

Starting on day 10 post fusion, cultured supernatants were harvest from the fusion plates and assayed for their ability to bind to SAL-S1. In this ELISA assay, SAL-S1 $IgG_1$ was coated onto 96 microtiter plates. The cultured supernatants (100 μl) were added to the wells and the mouse antibodies present were bound to Sal-S1 $IgG_1$. The plates were washed and mouse IgG was detected using a goat anti-mouse IgG (Fc specific with no cross reactivity against human IgG Fc) horseradish peroxidase conjugate and orthophenylene diamine substrate. Quantitation of substrate catalysis was determined by optical density at 490 nm.

Cultured supernatants which were positive from ELISA were then tested for their ability to specifically bind to 293 transfected with SAL-S1 receptor and analyzed by flow cytometry. Agonist antibodies were then screened for using the techniques disclosed in Example 10 below. Six agonist monoclonal antibodies were identified.

EXAMPLE 10

Agonist Activity of Monoclonal Antibodies to Sal-S1

The monoclonal antibodies were tested for their ability to induce SAL-S1 phosphorylation in SAL-S1 transfected 293 cells. Cells were harvested from tissue culture dish by assay buffer and washed 2×with the same buffer. $1\times10^5$ cells were added to a 96 U-bottom plate which was centrifuged and assay buffer was removed. 150 μl of cultured supernatants was added to each well followed by incubation at 37° C. for 30 minutes, the plate was centrifuged and cultured supernatants were removed. 100 μl of Fixing solution was added, the cells were fixed for 30 minutes at −20° C., cells were washed with buffer 2× and stained with anti-phosphotyrosine conjugate with FITC for 60 minutes at 4° C. Cells were analyzed by flow cytometry (FACScan Becton Dickinson, Milplitas, Calif.). The six anti-SAL-S1 monoclonal antibodies were able to induce SAL-S1 phosphorylation in SAL-S1 transfected 293 cells.

Deposit of Materials

The following culture has been deposited with the American Type Culture Collection, 12301 Parklawn Drive, Rockville, Md., USA (ATCC):

| Hybridoma | ATCC No. | Deposit Date |
|---|---|---|
| Anti-HpTK5 | HB 11,583 | March 15, 1994 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the culture deposited, since the deposited embodiment is intended as a single illustration of one aspect of the invention and any culture that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

Equivalents

Those skilled in the art will recognize, or be able to ascertain using no more than routine experimentation, many equivalents to the specific embodiments of the invention described herein. Such equivalents are intended to be encompassed by the following claims.

```
                          SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (xi) SEQUENCE DESCRIPTION: SEQ ID NO:1:

CGGATCCACA GNGACCT                                                      17

(2) INFORMATION FOR SEQ ID NO:2:

(i) SEQUENCE CHARACTERISTICS:
        (A) LENGTH: 23 base pairs
        (B) TYPE: Nucleic Acid
        (C) STRANDEDNESS: Single
        (D) TOPOLOGY: Linear (xi) SEQUENCE DESCRIPTION: SEQ ID NO:2:

GGAATTCCAA AGGACCAGAC GTC                                               23

(2) INFORMATION FOR SEQ ID NO:3:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO:3:

CGGATCCATC CACAGAGATG T                                                 21

(2) INFORMATION FOR SEQ ID NO:4:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (xi) SEQUENCE DESCRIPTION: SEQ ID NO:4:

GGAATTCCTT CAGGAGCCAT CCACTT                                            26

(2) INFORMATION FOR SEQ ID NO:5:

(i) SEQUENCE CHARACTERISTICS:
        (A) LENGTH: 160 base pairs
        (B) TYPE: Nucleic Acid
        (C) STRANDEDNESS: Single
        (D) TOPOLOGY: Linear (xi) SEQUENCE DESCRIPTION: SEQ ID NO:5:

GGATCCTGTG CATCAGTGAC TTAGGGCTAG GAACATTCTG CTGTCGGAAA                  50

GCGACGTGGT GAAGATCTGT GACTTTGGCC TTGCCCGGGA CATCTACAAA                 100
```

```
GACCCCAGCT ACGTCCGCAA GCATGCCCGG CTGCCCCTGA AGTGGATGGC          150

GCCAGAATTC                                                      160
```

(2) INFORMATION FOR SEQ ID NO:6:

(i) SEQUENCE CHARACTERISTICS:
        (A) LENGTH: 53 amino acids
        (B) TYPE: Amino Acid
        (D) TOPOLOGY: Linear (xi) SEQUENCE DESCRIPTION: SEQ ID NO:6:

```
Asp Pro Val His Gln Xaa Leu Arg Ala Arg Asn Ile Leu Leu Ser
 1               5                  10                  15

Glu Ser Asp Val Val Lys Ile Cys Asp Phe Gly Leu Ala Arg Asp
                20                  25                  30

Ile Tyr Lys Asp Pro Ser Tyr Val Arg Lys His Ala Arg Leu Pro
                35                  40                  45

Leu Lys Trp Met Ala Pro Glu Phe
                50          53
```

(2) INFORMATION FOR SEQ ID NO:7:

(i) SEQUENCE CHARACTERISTICS:
        (A) LENGTH: 147 base pairs
        (B) TYPE: Nucleic Acid
        (C) STRANDEDNESS: Single
        (D) TOPOLOGY: Linear (xi) SEQUENCE DESCRIPTION: SEQ ID NO:7:

```
GGATCCATTC ACAGAGACCT AGCAGCACGC AACATCCTGG TCTCAGAGGA          50

CCTGGTAACC AAGGTCAGCG ACTTTGGCCT GGCCAAAGCC GAGCGGAAGG          100

GGCTAGACTC AAGCCGGCTG CCCGTCAAAT GGATGGCTCC CGAATTC             147
```

(2) INFORMATION FOR SEQ ID NO:8:

(i) SEQUENCE CHARACTERISTICS:
        (A) LENGTH: 49 amino acids
        (B) TYPE: Amino Acid
        (D) TOPOLOGY: Linear (xi) SEQUENCE DESCRIPTION: SEQ ID NO:8:

```
Gly Ser Ile His Arg Asp Leu Ala Ala Arg Asn Ile Leu Val Ser
 1               5                  10                  15

Glu Asp Leu Val Thr Lys Val Ser Asp Phe Gly Leu Ala Lys Ala
                20                  25                  30

Glu Arg Lys Gly Leu Asp Ser Ser Arg Leu Pro Val Lys Trp Met
                35                  40                  45

Ala Pro Glu Phe
            49
```

(2) INFORMATION FOR SEQ ID NO:9:

(i) SEQUENCE CHARACTERISTICS:
        (A) LENGTH: 149 base pairs
        (B) TYPE: Nucleic Acid
        (C) STRANDEDNESS: Single
        (D) TOPOLOGY: Linear (xi) SEQUENCE DESCRIPTION: SEQ ID NO:9:

```
GTTGGAATTC CTTCCGGCGC CATCCATTTC ACCGGCAGCT TTATTTCGTG          50
```

```
TCTAGATTCA TAGATGTCTT CATTATCTAC CTTAAAAACT CTGGCAAGTC          100

CAAAATCTGC TACTTTGTAG ATATTATGTT CACCAACGAG GACATTCCT          149
```

(2) INFORMATION FOR SEQ ID NO:10:

(i) SEQUENCE CHARACTERISTICS:
        (A) LENGTH: 47 amino acids
        (B) TYPE: Amino Acid
        (D) TOPOLOGY: Linear (xi) SEQUENCE DESCRIPTION: SEQ ID NO:10:

```
Val Gly Ile Pro Ser Gly Ala Ile His Phe Thr Gly Ser Phe Ile
 1               5                  10                  15

Ser Cys Leu Asp Ser Met Ser Ser Leu Ser Thr Leu Lys Thr Leu
                20                  25                  30

Ala Ser Pro Lys Ser Ala Thr Leu Ile Leu Cys Ser Pro Thr Arg
                35                  40                  45

Thr Phe
    47
```

(2) INFORMATION FOR SEQ ID NO:11:

(i) SEQUENCE CHARACTERISTICS:
        (A) LENGTH: 151 base pairs
        (B) TYPE: Nucleic Acid
        (C) STRANDEDNESS: Single
        (D) TOPOLOGY: Linear (xi) SEQUENCE DESCRIPTION: SEQ ID NO:11:

```
GTGCACAGGG ATCTCGCGGC TCGGAACATC CTCGTCGGGG AAAACACCCT          50

CTCGAAAGTT GGGGACTTCG GGTTAGCCAG GCTTATCAAG GAGGACGTCT         100

ACCTCTCCCA TGACCACAAT ATCCCCTACA AATGGATGGC CCCTGAGGGA         150

A                                                              151
```

(2) INFORMATION FOR SEQ ID NO:12:

(i) SEQUENCE CHARACTERISTICS:
        (A) LENGTH: 50 amino acids
        (B) TYPE: Amino Acid
        (D) TOPOLOGY: Linear (xi) SEQUENCE DESCRIPTION: SEQ ID NO:12:

```
Val His Arg Asp Leu Ala Ala Arg Asn Ile Leu Val Gly Glu Asn
 1               5                  10                  15

Thr Leu Ser Lys Val Gly Asp Phe Gly Leu Ala Arg Leu Ile Lys
                20                  25                  30

Glu Asp Val Tyr Leu Ser His Asp His Asn Ile Pro Tyr Lys Trp
                35                  40                  45

Met Ala Pro Glu Gly
                50
```

(2) INFORMATION FOR SEQ ID NO:13:

(i) SEQUENCE CHARACTERISTICS:
        (A) LENGTH: 137 base pairs
        (B) TYPE: Nucleic Acid
        (C) STRANDEDNESS: Single
        (D) TOPOLOGY: Linear (xi) SEQUENCE DESCRIPTION: SEQ ID NO:13:

```
GTTCACCGAG ATCTCAAGTC CAACAACATT TTGCTGCTGC AGCCCATTGA          50
```

```
GAGTGACGAC ATGGAGCACA AGACCCTGAA GATCACCGAC TTTGGCCTGG         100

CCCGAGAGTG GCACAAAACC ACACAAATGA GTGCCGC                       137
```

(2) INFORMATION FOR SEQ ID NO:14:

(i) SEQUENCE CHARACTERISTICS:
        (A) LENGTH: 45 amino acids
        (B) TYPE: Amino Acid
        (D) TOPOLOGY: Linear (xi) SEQUENCE DESCRIPTION: SEQ ID NO:14:

```
Val His Arg Asp Leu Lys Ser Asn Asn Ile Leu Leu Gln Pro
 1           5                  10                  15

Ile Glu Ser Asp Asp Met Glu His Lys Thr Leu Lys Ile Thr Asp
            20                  25                  30

Phe Gly Leu Ala Arg Glu Trp His Lys Thr Thr Gln Met Ser Ala
            35                  40                  45
```

(2) INFORMATION FOR SEQ ID NO:15:

(i) SEQUENCE CHARACTERISTICS:
        (A) LENGTH: 211 base pairs
        (B) TYPE: Nucleic Acid
        (C) STRANDEDNESS: Single
        (D) TOPOLOGY: Linear (xi) SEQUENCE DESCRIPTION: SEQ ID NO:15:

```
GTCAATCGTG ACCTCGCCGC CGAAATGTGT TGCTAGTTA CCCAACATTA          50

CGCCAAGATC AGTGATTTCG GACTTTCCAA AGCACTGCGT GCTGATGAAA         100

ACTACTACAA GGCCCAGACC CATGGAAAGT GGCCTGTCAA GTGGTACGCT         150

CCGGAATGCA TCAACTACTA CAAGTTCTCC AGCAAAAGCG ATGTCTGGTC         200

CTTTGGAATT C                                                   211
```

(2) INFORMATION FOR SEQ ID NO:16:

(i) SEQUENCE CHARACTERISTICS:
        (A) LENGTH: 70 amino acids
        (B) TYPE: Amino Acid
        (D) TOPOLOGY: Linear (xi) SEQUENCE DESCRIPTION: SEQ ID NO:16:

```
Val Asn Arg Asp Leu Ala Ala Arg Asn Val Leu Leu Val Thr Gln
 1           5                  10                  15

His Tyr Ala Lys Ile Ser Asp Phe Gly Leu Ser Lys Ala Leu Arg
            20                  25                  30

Ala Asp Glu Asn Tyr Tyr Lys Ala Gln Thr His Gly Lys Trp Pro
            35                  40                  45

Val Lys Trp Tyr Ala Pro Glu Cys Ile Asn Tyr Tyr Lys Phe Ser
            50                  55                  60

Ser Lys Ser Asp Val Trp Ser Phe Gly Ile
            65                  70
```

(2) INFORMATION FOR SEQ ID NO:17:

(i) SEQUENCE CHARACTERISTICS:
        (A) LENGTH: 6827 base pairs
        (B) TYPE: Nucleic Acid
        (C) STRANDEDNESS: Single
        (D) TOPOLOGY: Linear -continued (xi) SEQUENCE DESCRIPTION: SEQ ID NO:17:

```
TTCGAGCTCG CCCGACATTG ATTATTGACT AGTTATTAAT AGTAATCAAT        50

TACGGGGTCA TTAGTTCATA GCCCATATAT GGAGTTCCGC GTTACATAAC       100

TTACGGTAAA TGGCCCGCCT GGCTGACCGC CCAACGACCC CCGCCCATTG       150

ACGTCAATAA TGACGTATGT TCCCATAGTA ACGCCAATAG GGACTTTCCA       200

TTGACGTCAA TGGGTGGAGT ATTTACGGTA AACTGCCCAC TTGGCAGTAC       250

ATCAAGTGTA TCATATGCCA AGTACGCCCC CTATTGACGT CAATGACGGT       300

AAATGGCCCG CCTGGCATTA TGCCCAGTAC ATGACCTTAT GGGACTTTCC       350

TACTTGGCAG TACATCTACG TATTAGTCAT CGCTATTACC ATGGTGATGC       400

GGTTTTGGCA GTACATCAAT GGGCGTGGAT AGCGGTTTGA CTCACGGGGA       450

TTTCCAAGTC TCCACCCCAT TGACGTCAAT GGGAGTTTGT TTTGGCACCA       500

AAATCAACGG GACTTTCCAA AATGTCGTAA CAACTCCGCC CCATTGACGC       550

AAATGGGCGG TAGGCGTGTA CGGTGGGAGG TCTATATAAG CAGAGCTCGT       600

TTAGTGAACC GTCAGATCGC CTGGAGACGC CATCCACGCT GTTTTGACCT       650

CCATAGAAGA CACCGGGACC GATCCAGCCT CCGCGGCCGG GAACGGTGCA       700

TTGGAACGCG GATTCCCCGT GCCAAGAGTG ACGTAAGTAC CGCCTATAGA       750

GTCTATAGGC CCACTTGGCT TCGTTAGAAC GCGGCTACAA TTAATACATA       800

ACCTTATGTA TCATACACAT ACGATTTAGG TGACACTATA GAATAACATC       850

CACTTTGCCT TTCTCTCCAC AGGTGTCCAC TCCCAGGTCC AACTGCACCT       900

CGGTTCTATC GATTGAATTC CCCGGGGATC CTCTAGAGAT CCCTCGACCT       950

CGAGATCCAT TGTGCTGGCG CGGATTCTTT ATCACTGATA AGTTGGTGGA      1000

CATATTATGT TTATCAGTGA TAAAGTGTCA AGCATGACAA AGTTGCAGCC      1050

GAATACAGTG ATCCGTGCCG CCCTAGACCT GTTGAACGAG GTCGGCGTAG      1100

ACGGTCTGAC GACACGCAAA CTGGCGGAAC GGTTGGGGGT TCAGCAGCCG      1150

GCGCTTTACT GGCACTTCAG GAACAAGCGG GCGCTGCTCG ACGCACTGGC      1200

CGAAGCCATG CTGGCGGAGA ATCATAGCAC TTCGGTGCCG AGAGCCGACG      1250

ACGACTGGCG CTCATTTCTG ACTGGGAATG CCCGCAGCTT CAGGCAGGCG      1300

CTGCTCGCCT ACCGCCAGCA CAATGGATCT CGAGGGATCT TCCATACCTA      1350

CCAGTTCTGC GCCTGCAGGT CGCGGCCGCA CTACTCTTTG ATGTATTACT      1400

CATATTACCA AGGAATAACT GGCGGGCACA GGGTCAGGTG CTGAAGGGAC      1450

ATTGTGAGAA GTGACCTAGA AGGCAAGAGG TGAGCCCTCT GTCACGCTGG      1500

CATAAGGGCC GCTTGAGGGC TCTTTGGTCA AGCAGTAACG CCAGTGTCTG      1550

GGAAGGCACC TGTTACTCAG CAGACCATGA AAGGGCGTCT CCCTTTCCTT      1600

GGAGCAGTCA GGGAACACTC TGCTCCACCA GCTTCTTGTG GGAGCCTGGA      1650

TATTATCCAG GCCTGCCCGC AGTCATCCGG AGGCCTAACC CCTCCCTGTG      1700

GTGCTTCAGT GGTCACACTC CTTGTCCACT TTCATGCTCC TCTTGGCCTC      1750

CTGGTTCCTC TTGGAAGTTT GTAGTAGATA GCAGAAGAAA TAGCGAAAGT      1800

CTTAAAGTCT TTGATCTTTC TTATAAGTGC AGAGAAGAAA TGCTGACGTA      1850

TGCTGCCTTC TCTCTCTCTG CTTCAGCTAC CTGAAGCCGC TTTCTTGTCT      1900

ATACCTGCTC TCTATCTGCT CACACTCCTC CGAGGCCAGC ACCATCCCAC      1950
```

```
TGTCTGTCTG GTTGTCCACA GAGCCTTTGT AGGTCGTTGG GGTCATGGGG           2000

AATTCCTCAA ATGTCTTCAT CCTGGAGGAA CCACGGGTCT CAGCCCCTCT           2050

GGCCAGGCAC CCGGGAAAGG ACACCCAGTT GTAATACCTG GCGGCCAGGC           2100

TGTGGCGCTG CAGGCTTGGC GGGCTGTCCT CAGCGTCAGC CTGGGCGATG           2150

TGTAGGGCCA TGGTGGACAC CTGCGAGAAG CTGCCCTCTT CTGAGCTCTG           2200

AGAGCTGCGC GGGGCCATGC AGACCTCCTC TTCCTCTTGC AGGCCCCTGC           2250

CCTGGAGCAG GTCCCCCAGG ATCTCCACCA GCTCCGAGAA TGCAGGTCTC           2300

GCCTTGGGGT CTCCGGACCA GCAGTTCAGC ATGATGCGGC GTATGGCGGG           2350

AGTGGCCAGC TCCGGGGCCC TCATCCTTGT GCCGTCTCTC AGCCGCTGGC           2400

AGAACTCCTC ATTGATCTGC ACCCCAGGGT ACGGGAGGC  CCCCAGAGAG           2450

AAGATCTCCC AGAGAAGCAC CCCAAAGGAC ACACGTCAC  TCTGCGTGGT           2500

GTACACCTTG TCGAAGATGC TTTCAGGGGC CATCCACTTC AGGGGCAGCC           2550

GGGCACTGCC CTTGCGGACG TAGTCGGGGT CTTTGTAGAT GTCCCGGGCA           2600

AGGCCAAAGT CACAGATCTT CACCACGTCG CTTTCCGACA GCAGAATGTT           2650

CCGAGCAGCC AGGTCTCTGT GGATGCACTT TCGGGAAGCC AGGAACTCCA           2700

TCCCTCTGGC CACCTGGAAG CTGTAGCAGA CAAGATCTTC CATGGTCAGC           2750

GGGCTCAGCC ACAGGTCCTC AGCTTCTTGG TCTGGAGAAG CCCGCCTCGC           2800

TCCGCCCTCG GTCTTCGAGA ACCGCGCGAA GAGGACCCTG TCGCTGCTCC           2850

CCGGCCGCCT CCGATCCAGC CTGGCGAGCT CCACCATGGC GCGGAAGCGT           2900

CCGCGCTGCT CGGGAGACTT CTCCTGCGGA TGCACGAAGC TGGCTCGAGG           2950

GCGCCCAGTC GTCCGCCGCA GAGGCGCCTC CATTCCCCCG CCGCCCGCGG           3000

CGCCCCGCAG GCCGCCCGCT CACCGNGCAG GGGCTGCGGC CGCGACTCTA           3050

GAGTCGACCT GCAGAAGCTT GGCCGCCATG GCCCAACTTG TTTATTGCAG           3100

CTTATAATGG TTACAAATAA AGCAATAGCA TCACAAATTT CACAAATAAA           3150

GCATTTTTTT CACTGCATTC TAGTTGTGGT TTGTCCAAAC TCATCAATGT           3200

ATCTTATCAT GTCTGGATCG ATCGGGAATT AATTCGGCGC AGCACCATGG           3250

CCTGAAATAA CCTCTGAAAG AGGAACTTGG TTAGGTACCT TCTGAGGCGG           3300

AAAGAACCAG CTGTGGAATG TGTGTCAGTT AGGGTGTGGA AAGTCCCCAG           3350

GCTCCCCAGC AGGCAGAAGT ATGCAAAGCA TGCATCTCAA TTAGTCAGCA           3400

ACCAGGTGTG GAAAGTCCCC AGGCTCCCCA GCAGGCAGAA GTATGCAAAG           3450

CATGCATCTC AATTAGTCAG CAACCATAGT CCCGCCCCTA ACTCCGCCCA           3500

TCCCGCCCCT AACTCCGCCC AGTTCCGCCC ATTCTCCGCC CCATGGCTGA           3550

CTAATTTTTT TTATTTATGC AGAGGCCGAG GCCGCCTCGG CCTCTGAGCT           3600

ATTCCAGAAG TAGTGAGGAG GCTTTTTTGG AGGCCTAGGC TTTTGCAAAA           3650

AGCTGTTAAC AGCTTGGCAC TGGCCGTCGT TTTACAACGT CGTGACTGGG           3700

AAAACCCTGG CGTTACCCAA CTTAATCGCC TTGCAGCACA TCCCCCCTTC           3750

GCCAGCTGGC GTAATAGCGA AGAGGCCCGC ACCGATCGCC CTTCCCAACA           3800

GTTGCGTAGC CTGAATGGCG AATGGCGCCT GATGCGGTAT TTTCTCCTTA           3850

CGCATCTGTG CGGTATTTCA CACCGCATAC GTCAAAGCAA CCATAGTACG           3900
```

```
CGCCCTGTAG CGGCGCATTA AGCGCGGCGG GTGTGGTGGT TACGCGCAGC      3950

GTGACCGCTA CACTTGCCAG CGCCCTAGCG CCCGCTCCTT TCGCTTTCTT      4000

CCCTTCCTTT CTCGCCACGT TCGCCGGCTT TCCCCGTCAA GCTCTAAATC      4050

GGGGGCTCCC TTTAGGGTTC CGATTTAGTG CTTTACGGCA CCTCGACCCC      4100

AAAAAACTTG ATTTGGGTGA TGGTTCACGT AGTGGGCCAT CGCCCTGATA      4150

GACGGTTTTT CGCCCTTTGA CGTTGGAGTC CACGTTCTTT AATAGTGGAC      4200

TCTTGTTCCA AACTGGAACA ACACTCAACC CTATCTCGGG CTATTCTTTT      4250

GATTTATAAG GGATTTTGCC GATTTCGGCC TATTGGTTAA AAAATGAGCT      4300

GATTTAACAA AAATTTAACG CGAATTTTAA CAAAATATTA ACGTTTACAA      4350

TTTTATGGTG CACTCTCAGT ACAATCTGCT CTGATGCCGC ATAGTTAAGC      4400

CAACTCCGCT ATCGCTACGT GACTGGGTCA TGGCTGCGCC CCGACACCCG      4450

CCAACACCCG CTGACGCGCC CTGACGGGCT TGTCTGCTCC CGGCATCCGC      4500

TTACAGACAA GCTGTGACCG TCTCCGGGAG CTGCATGTGT CAGAGGTTTT      4550

CACCGTCATC ACCGAAACGC GCGAGGCAGT ATTCTTGAAG ACGAAAGGGC      4600

CTCGTGATAC GCCTATTTTT ATAGGTTAAT GTCATGATAA TAATGGTTTC      4650

TTAGACGTCA GGTGGCACTT TTCGGGGAAA TGTGCGCGGA ACCCCTATTT      4700

GTTTATTTTT CTAAATACAT TCAAATATGT ATCCGCTCAT GAGACAATAA      4750

CCCTGATAAA TCTTCAATAA TATTGAAAAA GGAAGAGTAT GAGTATTCAA      4800

ACATTTCCGT GTCGCCCTTA TTCCCTTTTT GGCGGCATTT TGCCTTCCTG      4850

TTTTTGCTCA CCCAGAAACG CTGGTGAAAG TAAAAGATGC TGAAGATCAG      4900

TTGGGTGCAC GAGTGGGTTA CATCGAACTG GATCTCAACA GCGGTAAGAT      4950

CCTTGAGAGT TTTCGCCCCG AAGAACGTTT TCCAATGATG AGCACTTTTA      5000

AAGTTCTGCT ATGTGGCGCG GTATTATCCC GTGATGACGC CGGGCAAGAG      5050

CAACTCGGTC GCCGCATACA CTATTCTCAG AATGACTTGG TTGAGTACTC      5100

ACCAGTCACA GAAAAGCATC TTACGGATGG CATGACAGTA AGAGAATTAT      5150

GCAGTGCTGC CATAACCATG AGTGATAACA CTGCGGCCAA CTTACTTCTG      5200

ACAACGATCG GAGGACCGAA GGAGCTAACC GCTTTTTTGC ACAACATGGG      5250

GGATCATGTA ACTCGCCTTG ATCGTTGGGA ACCGGAGCTG AATGAAGCCA      5300

TACCAAACGA CGAGCGTGAC ACCACGATGC CAGCAGCAAT GGCAACAACG      5350

TTGCGCAAAC TATTAACTGG CGAACTACTT ACTCTAGCTT CCCGGCAACA      5400

ATTAATAGAC TGGATGGAGG CGGATAAAGT TGCAGGACCA CTTCTGCGCT      5450

CGGCCCTTCC GGCTGGCTGG TTTATTGCTG ATAAATCTGG AGCCGGTGAG      5500

CGTGGGTCTC GCGGTATCAT TGCAGCACTG GGGCCAGATG GTAAGCCCTC      5550

CCGTATCGTA GTTATCTACA CGACGGGGAG TCAGCAACT ATGGATGAAC       5600

GAAATAGACA GATCGCTGAG ATAGGTGCCT CACTGATTAA GCATTGGTAA      5650

CTGTCAGACC AAGTTTACTC ATATATACTT TAGATTGATT TAAAACTTCA      5700

TTTTTAATTT AAAAGGATCT AGGTGAAGAT CCTTTTTGAT AATCTCATGA      5750

CCAAAATCCC TTAACGTGAG TTTTCGTTCC ACTGAGCGTC AGACCCCGTA      5800

GAAAAGATCA AAGGATCTTC TTGAGATCCT TTTTTTCTGC GCGTAATCTG      5850

CTGCTTGCAA ACAAAAAAAC CACCGCTACC AGCGGTGGTT TGTTTGCCGG      5900
```

| | |
|---|---|
| ATCAAGAGCT ACCAACTCTT TTTCCGAAGG TAACTGGCTT CAGCAGAGCG | 5950 |
| CAGATACCAA ATACTGTCCT TCTAGTGTAG CCGTAGTTAG GCCACCACTT | 6000 |
| CAAGAACTCT GTAGCACCGC CTACATACCT CGCTCTGCTA ATCCTGTTAC | 6050 |
| CAGTGGCTGC TGCCAGTGGC GATAAGTCGT GTCTTACCGG GTTGGACTCA | 6100 |
| AGACGATAGT TACCGGATAA GGCGCAGCGG TCGGGCTGAA CCGGGGGTTC | 6150 |
| GTGCACACAG CCCAGCTTGG AGCGAACGAC CTACACCGAA CTGAGATACC | 6200 |
| TACAGCGTGA GCATTGAGAA AGCGCCACGC TTCCCGAAGG GAGAAAGGCG | 6250 |
| GACAGGTATC CGGTAAGCGG CAGGGTCGGA ACAGGAGAGC GCACGAGGGA | 6300 |
| GCTTCCAGGG GGAAACGCCT GGTATCTTTA TAGTCCTGTC GGGTTTCGCC | 6350 |
| ACCTCTGACT TGAGCGTCGA TTTTTGTGAT GCTCGTCAGG GGGGCGGAGC | 6400 |
| CTATGGAAAA ACGCCAGCAA CGCGGCCTTT TTACGGTTCC TGGCCTTTTG | 6450 |
| CTGGCCTTTT GCTCACATGT TCTTTCCTGC GTTATCCCCT GATTCTGTGG | 6500 |
| ATAACCGTAT TACCGCCTTT GAGTGAGCTG ATACCGCTCG CCGCAGCCGA | 6550 |
| ACGACCGAGC GCAGCGAGTC AGTGAGCGAG GAAGCGGAAG AGCGCCCAAT | 6600 |
| ACGCAAACCG CCTCTCCCCG CGCGTTGGCC GATTCATTAA TCCAGCTGGC | 6650 |
| ACGACAGGTT TCCCGACTGG AAAGCGGGCA GTGAGCGCAA CGCAATTAAT | 6700 |
| GTGAGTTACC TCACTCATTA GGCACCCCAG GCTTTACACT TTATGCTTCC | 6750 |
| GGCTCGTATG TTGTGTGGAA TTGTGAGCGG ATAACAATTT CACACAGGAA | 6800 |
| ACAGCTATGA CCATGATTAC GAATTAA | 6827 |

(2) INFORMATION FOR SEQ ID NO:18:

(i) SEQUENCE CHARACTERISTICS:
        (A) LENGTH: 348 amino acids
        (B) TYPE: Amino Acid
        (D) TOPOLOGY: Linear (xi) SEQUENCE DESCRIPTION: SEQ ID NO:18:

```
Glu Lys Ser Pro Glu Gln Arg Gly Arg Phe Arg Ala Met Val Glu
 1               5                  10                  15

Leu Ala Arg Leu Asp Arg Arg Pro Gly Ser Ser Asp Arg Val
                20                  25                  30

Leu Phe Ala Arg Phe Ser Lys Thr Glu Gly Gly Ala Arg Arg Ala
                35                  40                  45

Ser Pro Asp Gln Glu Ala Glu Asp Leu Trp Leu Ser Pro Leu Thr
                50                  55                  60

Met Glu Asp Leu Val Cys Tyr Ser Phe Gln Val Ala Arg Gly Met
                65                  70                  75

Glu Phe Leu Ala Ser Arg Lys Cys Ile His Arg Asp Leu Ala Ala
                80                  85                  90

Arg Asn Ile Leu Leu Ser Glu Ser Asp Val Val Lys Ile Cys Asp
                95                  100                 105

Phe Gly Leu Ala Arg Asp Ile Tyr Lys Asp Pro Asp Tyr Val Arg
                110                 115                 120

Lys Gly Ser Ala Arg Leu Pro Leu Lys Trp Met Ala Pro Glu Ser
                125                 130                 135

Ile Phe Asp Lys Val Tyr Thr Thr Gln Ser Asp Val Trp Ser Phe
                140                 145                 150
```

```
Gly Val Leu Leu Trp Glu Ile Phe Ser Leu Gly Ala Ser Pro Tyr
            155                 160                 165

Pro Gly Val Gln Ile Asn Glu Glu Phe Cys Gln Arg Leu Arg Asp
            170                 175                 180

Gly Thr Arg Met Arg Ala Pro Glu Leu Ala Thr Pro Ala Ile Arg
            185                 190                 195

Arg Ile Met Leu Asn Cys Trp Ser Gly Asp Pro Lys Ala Arg Pro
            200                 205                 210

Ala Phe Ser Glu Leu Val Glu Ile Leu Gly Asp Leu Leu Gln Gly
            215                 220                 225

Arg Gly Leu Gln Glu Glu Glu Val Cys Met Ala Pro Arg Ser
            230                 235                 240

Ser Gln Ser Ser Glu Glu Gly Ser Phe Ser Gln Val Ser Thr Met
            245                 250                 255

Ala Leu His Ile Ala Gln Ala Asp Ala Glu Asp Ser Pro Pro Ser
            260                 265                 270

Leu Gln Arg His Ser Leu Ala Ala Arg Tyr Tyr Asn Trp Val Ser
            275                 280                 285

Phe Pro Gly Cys Leu Ala Arg Gly Ala Glu Thr Arg Gly Ser Ser
            290                 295                 300

Arg Met Lys Thr Phe Glu Glu Phe Pro Met Thr Pro Thr Thr Tyr
            305                 310                 315

Lys Gly Ser Val Asp Asn Gln Thr Asp Ser Gly Met Val Leu Ala
            320                 325                 330

Ser Glu Glu Cys Glu Gln Ile Glu Ser Arg Tyr Arg Gln Glu Ser
            335                 340                 345

Gly Phe Arg
    348

(2) INFORMATION FOR SEQ ID NO:19:

(i) SEQUENCE CHARACTERISTICS:
        (A) LENGTH: 7607 base pairs
        (B) TYPE: Nucleic Acid
        (C) STRANDEDNESS: Single
        (D) TOPOLOGY: Linear (xi) SEQUENCE DESCRIPTION: SEQ ID NO:19:

TTCGAGCTCG CCCGACATTG ATTATTGACT AGTTATTAAT AGTAATCAAT              50

TACGGGGTCA TTAGTTCATA GCCCATATAT GGAGTTCCGC GTTACATAAC             100

TTACGGTAAA TGGCCCGCCT GGCTGACCGC CCAACGACCC CCGCCCATTG             150

ACGTCAATAA TGACGTATGT TCCCATAGTA ACGCCAATAG GGACTTTCCA             200

TTGACGTCAA TGGGTGGAGT ATTTACGGTA AACTGCCCAC TTGGCAGTAC             250

ATCAAGTGTA TCATATGCCA AGTACGCCCC CTATTGACGT CAATGACGGT             300

AAATGGCCCG CCTGGCATTA TGCCCAGTAC ATGACCTTAT GGGACTTTCC             350

TACTTGGCAG TACATCTACG TATTAGTCAT CGCTATTACC ATGGTGATGC             400

GGTTTTGGCA GTACATCAAT GGGCGTGGAT AGCGGTTTGA CTCACGGGGA             450

TTTCCAAGTC TCCACCCCAT TGACGTCAAT GGGAGTTTGT TTTGGCACCA             500

AAATCAACGG GACTTTCCAA AATGTCGTAA CAACTCCGCC CCATTGACGC             550

AAATGGGCGG TAGGCGTGTA CGGTGGGAGG TCTATATAAG CAGAGCTCGT             600

TTAGTGAACC GTCAGATCGC CTGGAGACGC CATCCACGCT GTTTTGACCT             650
```

-continued

| | |
|---|---|
| CCATAGAAGA CACCGGGACC GATCCAGCCT CCGCGGCCGG GAACGGTGCA | 700 |
| TTGGAACGCG GATTCCCCGT GCCAAGAGTG ACGTAAGTAC CGCCTATAGA | 750 |
| GTCTATAGGC CCACTTGGCT TCGTTAGAAC GCGGCTACAA TTAATACATA | 800 |
| ACCTTATGTA TCATACACAT ACGATTTAGG TGACACTATA GAATAACATC | 850 |
| CACTTTGCCT TTCTCTCCAC AGGTGTCCAC TCCCAGGTCC AACTGCACCT | 900 |
| CGGTTCTATC GATTGAATTC CCCGGGGATC CTCTAGAGAT CCCTCGACCT | 950 |
| CGAGTCGACT TTTTTTTTTT TTTTTGTAGG CCAAAGGGTA CTTCTTTTTC | 1000 |
| TTTATTAATT ACTCAGAAGT CTAGGCCACA GCAATCTACT GTTCTCCTCT | 1050 |
| CATTTTCCTA AACTATTTTG ATACCTATTT CTCAGACTTT ATGGGCTATT | 1100 |
| AGACATTTCT CACATTTCCA TAGATAATAA CTCATCCGTT TTGCAACCTG | 1150 |
| ATTCTCAATA TTAAGAGATT AAAACTAATG TATATGACTC TCAGTTGACA | 1200 |
| CATACTGAAG TACAGAAAAA TTCCATCATT TCCTTCTGCA AAATGAAAAA | 1250 |
| GACTTCGTTT TCTCAACAGC TGCATCATTT TTTTATGCAT AGAAAAAAAT | 1300 |
| GTGCAATTAC TCCAAGTACA ATCAAGTCAT TTAACATGGC TTTACCATCA | 1350 |
| TTGTAGTTAC AGGATATTTT AAAAGAGAAA AAAAAATCTC AAAGCACAGG | 1400 |
| TCCTGCTGTG CAGCAAAGCA ATCAAATTCC TTCATAATAA CAGCCTGATG | 1450 |
| GGATTCAGCA ATCTGAGGAA TAATGAATAA CCACTCTAAT CAGTAAACAG | 1500 |
| GAAAATGCTA CAACAGTCAC TGAGTAAAAA TTGGACTATC ATCTGTTGAT | 1550 |
| TCTCTTGATC GACATTTCAA ACAATAAATG GAAATGTAAG TATCTCTTAA | 1600 |
| AAAGAAAAAT AACTTGGTTT AGTGTGCTTA ATTTTACCAG GCAGTGAGGA | 1650 |
| AATTATATAT CACCTTGACT GTCCTGCAGT GTTGCCCAGT CAATAAAATG | 1700 |
| CACAAATAAT CTTTTTCATA ATACATGGCC AACTTTATCC TATCACTTGA | 1750 |
| ATATGTCAGG ATAAACTGAT TGTGCAGTTG GTTGATAACA TTGTATTTTG | 1800 |
| GAATGGATTA TTTGAATTTG TTTTGCTACT TTATTATTTG ATATTCTTCT | 1850 |
| CCAGTGTTCA TCTTATGAAG TTATTTGCAT CTGAATATGA AGAGTCTGTT | 1900 |
| TCAAAATAGT CTTCAAGTTT CCAACGCAGT GTCTCAAATG TAGGTCGTTC | 1950 |
| CTTAGGCTCT GCATTCCAGC ACTCCAACAT GATGTTGTAA AATTGCTGTG | 2000 |
| GACAGTTGGA TGGTTGCGGA AGTCTATAGT TTTGAGCCAA CATCTGGATT | 2050 |
| ACCTGGGCAC CTGTCATACC ACTGTAAGGC ATTTTGCCAT AAGTAATGAT | 2100 |
| TTCATAAAGA AGGATTCCAA ATGACCATAC ATCGGACTTA ATGCTGAATT | 2150 |
| TATTACTACG AATGGCTTCG GGCGCAGTCC ACTTCACCGG CAGCTTTATT | 2200 |
| TCGTGTCTAG ATTCATAGAT GTCTTCATTA TCTACCTTAA AAACTCTGGC | 2250 |
| AAGTCCAAAA TCTGCTACTT TGTAGATATT ATGTTCACCA ACGAGGACAT | 2300 |
| TTCTGGCAGC CAGATCTCTG TGAATGTAGT TCCGAGACTC CAGATAGGCC | 2350 |
| ATTCCAGAGG CAACCTGTGC CGCCATGTCT ACCTGTTGAG TCAGATGGAT | 2400 |
| TTTTGATCCA GTGTCATTTT GGAGATATTC TTGCAGACTT CCATGTCTCA | 2450 |
| TCAACTCTGT AATAATATAA ATTGGATCTT CTAAAGTGCA AACAGCATAA | 2500 |
| AGCTGGATAA GCTTTGGATG TCTTAGGTTC TTCATTATCT GTGCCTCCCT | 2550 |
| CAGGAAGTCA TTTGGATCCA TTGAACCTGG TTTTAATGTT TTCACTGCTA | 2600 |
| CTGGAGTGGT ATTGTTCCAC AGACCTTCCC ATACTTCGCC AAACTGACCA | 2650 |

| | |
|---|---|
| GATCCCAATC GCTTCAGAAG CTGTATGGAG TTGCGGTCTA TCTCCCATTG | 2700 |
| GTCCACGGTT TTATACGACA AATCAAATGG AGCTGGGACC TGGATCTTTA | 2750 |
| AGCATGGTTT CCCCAGCTTG ACACACAGGC CGTCACTTGT CTTGGTGTAG | 2800 |
| TGGCTCACAA ATTCGTTCAG TGTTGAAAAG ATTCTTCTTC GCGTGAGAAA | 2850 |
| AAATCCCCCT TCATCCAGTC TTTTAATTCT GTAGTGTTTT ACAACTGCTC | 2900 |
| CATCTAAAAC TGAAAGAGAG AATTCTCCTT TTTGGCTTTC ACTTTCTCTG | 2950 |
| ATTAGAAAGG AACCGGTCTT GTTTTCTGAA TATAATAGTT GTTTCTCTGC | 3000 |
| ATCTGATCTT CCGATTGCTC CAAAGAACCA CGGCTCTGCC TGTAGGCTTC | 3050 |
| TGTCCTCAGC CACGTAGTTA GAAGGAATAT AGCCTTGTAG TTGCTGACTG | 3100 |
| GAGCCATCTC GTCTTTTCTC CAAGTGTCTG GCAAACCACC AGCCCTCATG | 3150 |
| CAAAGTGTCC AGAACTTGAA GTTTGTCACC TGCTCGGAAG CTCAAGTCCT | 3200 |
| CAGCAGTCCG AGCCTGGTAA TCAAACAAAG CCACAAAGTA GTGGCCATGC | 3250 |
| CTCTGTGACT GGGGAGAGCA AAGGGCCCCT GGATTTTCAA TCACGGTTGA | 3300 |
| CTTGTCTGCC TCCGTGGACA AACAGGGGAG ATAGGGTTCT AGGTACTCCC | 3350 |
| AGAGCCTCTG ACAGATGTTG CTCATTGTGC CTTGGTGGGG AGAAGAGGAG | 3400 |
| CAGGGCTTCT CCCTCTCCCC TTAGTCTCTG CGATCCACCT TATCTTCCTT | 3450 |
| CACCAGGCAA CTTTGAAGTC AGCACCAACT CACCATACTT CGGAGAGTAT | 3500 |
| GCAAAGTCCC GTTTCAGATC AGTCCAGCAG CTGGGTTGCA GCAAGTCCTA | 3550 |
| CCTGGAGAGA CTTACCGGCT TGCTTTCTGT GGCTGGAGGT GCTACCCCGA | 3600 |
| GGCAAAACTG AGCAGGAGCT GGGCAGCTGC TCACTAGGAA GGTGTCTTTT | 3650 |
| CTTCTTATCT GCTTAAGAAT CCCACAACAA AAATAAAATA AAATTAAAAG | 3700 |
| GGCTTTATTT AGACAAATAT CTGAGAACAG AATGGTGCCA TCTTGCCTTT | 3750 |
| TGTCCCAATA AAAAGTTAGC AAGAGGAAGC TACTAACCCC TGGTAAAACC | 3800 |
| TCCACGTCTT GCTTTCGCCA GGGTCGACTC GAGGGATCTT CCATACCTAC | 3850 |
| CAGTTCTGCG CCTGCAGGTC GCGGCCGCGA CTCTAGAGTC GACCTGCAGA | 3900 |
| AGCTTGGCCG CCATGGCCCA ACTTGTTTAT TGCAGCTTAT AATGGTTACA | 3950 |
| AATAAAGCAA TAGCATCACA AATTTCACAA ATAAAGCATT TTTTTCACTG | 4000 |
| CATTCTAGTT GTGGTTTGTC CAAACTCATC AATGTATCTT ATCATGTCTG | 4050 |
| GATCGGGAAT TAATTCGGCG CAGCACCATG GCCTGAAATA ACCTCTGAAA | 4100 |
| GAGGAACTTG GTTAGGTACC TTCTGAGGCG GAAAGAACCA GCTGTGGAAT | 4150 |
| GTGTGTCAGT TAGGGTGTGG AAAGTCCCCA GGCTCCCCAG CAGGCAGAAG | 4200 |
| TATGCAAAGC ATGCATCTCA ATTAGTCAGC AACCAGGTGT GGAAAGTCCC | 4250 |
| CAGGCTCCCC AGCAGGCAGA AGTATGCAAA GCATGCATCT CAATTAGTCA | 4300 |
| GCAACCATAG TCCCGCCCCT AACTCCGCCC ATCCCGCCCC TAACTCCGCC | 4350 |
| CAGTTCCGCC CATTCTCCGC CCCATGGCTG ACTAATTTTT TTTATTTATG | 4400 |
| CAGAGGCCGA GGCCGCCTCG GCCTCTGAGC TATTCCAGAA GTAGTGAGGA | 4450 |
| GGCTTTTTTG GAGGCCTAGG CTTTTGCAAA AAGCTGTTAA CAGCTTGGCA | 4500 |
| CTGGCCGTCG TTTTACAACG TCGTGACTGG GAAAACCCTG GCGTTACCCA | 4550 |
| ACTTAATCGC CTTGCAGCAC ATCCCCCTTT CGCCAGCTGG CGTAATAGCG | 4600 |

| | |
|---|---|
| AAGAGGCCCG CACCGATCGC CCTTCCCAAC AGTTGCGCAG CCTGAATGGC | 4650 |
| GAATGGCGCC TGATGCGGTA TTTTCTCCTT ACGCATCTGT GCGGTATTTC | 4700 |
| ACACCGCATA CGTCAAAGCA ACCATAGTAC GCGCCCTGTA GCGGCGCATT | 4750 |
| AAGCGCGGCG GGTGTGGTGG TTACGCGCAG CGTGACCGCT ACACTTGCCA | 4800 |
| GCGCCCTAGC GCCCGCTCCT TTCGCTTTCT TCCCTTCCTT TCTCGCCACG | 4850 |
| TTCGCCGGCT TTCCCCGTCA AGCTCTAAAT CGGGGGCTCC CTTTAGGGTT | 4900 |
| CCGATTTAGT GCTTTACGGC ACCTCGACCC CAAAAAACTT GATTTGGGTG | 4950 |
| ATGGTTCACG TAGTGGGCCA TCGCCCTGAT AGACGGTTTT TCGCCCTTTG | 5000 |
| ACGTTGGAGT CCACGTTCTT TAATAGTGGA CTCTTGTTCC AAACTGGAAC | 5050 |
| AACACTCAAC CCTATCTCGG GCTATTCTTT TGATTTATAA GGGATTTTGC | 5100 |
| CGATTTCGGC CTATTGGTTA AAAAATGAGC TGATTTAACA AAAATTTAAC | 5150 |
| GCGAATTTTA ACAAAATATT AACGTTTACA ATTTTATGGT GCACTCTCAG | 5200 |
| TACAATCTGC TCTGATGCCG CATAGTTAAG CCAGCCCCGA CACCCGCCAA | 5250 |
| CACCCGCTGA CGCGCCCTGA CGGGCTTGTC TGCTCCCGGC ATCCGCTTAC | 5300 |
| AGACAAGCTG TGACCGTCTC CGGGAGCTGC ATGTGTCAGA GGTTTTCACC | 5350 |
| GTCATCACCG AAACGCGCGA GACGAAAGGG CCTCGTGATA CGCCTATTTT | 5400 |
| TATAGGTTAA TGTCATGATA ATAATGGTTT CTTAGACGTC AGGTGGCACT | 5450 |
| TTTCGGGGAA ATGTGCGCGG AACCCCTATT TGTTTATTTT TCTAAATACA | 5500 |
| TTCAAATATG TATCCGCTCA TGAGACAATA ACCCTGATAA ATGCTTCAAT | 5550 |
| AATATTGAAA AAGGAAGAGT ATGAGTATTC AACATTTCCG TGTCGCCCTT | 5600 |
| ATTCCCTTTT TTGCGGCATT TTGCCTTCCT GTTTTTGCTC ACCCAGAAAC | 5650 |
| GCTGGTGAAA GTAAAAGATG CTGAAGATCA GTTGGGTGCA CGAGTGGGTT | 5700 |
| ACATCGAACT GGATCTCAAC AGCGGTAAGA TCCTTGAGAG TTTTCGCCCC | 5750 |
| GAAGAACGTT TTCCAATGAT GAGCACTTTT AAAGTTCTGC TATGTGGCGC | 5800 |
| GGTATTATCC CGTATTGACG CCGGGCAAGA GCAACTCGGT CGCCGCATAC | 5850 |
| ACTATTCTCA GAATGACTTG GTTGAGTACT CACCAGTCAC AGAAAAGCAT | 5900 |
| CTTACGGATG GCATGACAGT AAGAGAATTA TGCAGTGCTG CCATAACCAT | 5950 |
| GAGTGATAAC ACTGCGGCCA ACTTACTTCT GACAACGATC GGAGGACCGA | 6000 |
| AGGAGCTAAC CGCTTTTTTG CACAACATGG GGATCATGT AACTCGCCTT | 6050 |
| GATCGTTGGG AACCGGAGCT GAATGAAGCC ATACCAAACG ACGAGCGTGA | 6100 |
| CACCACGATG CCTGTAGCAA TGGCAACAAC GTTGCGCAAA CTATTAACTG | 6150 |
| GCGAACTACT TACTCTAGCT TCCCGGCAAC AATTAATAGA CTGGATGGAG | 6200 |
| GCGGATAAAG TTGCAGGACC ACTTCTGCGC TCGGCCCTTC CGGCTGGCTG | 6250 |
| GTTTATTGCT GATAAATCTG GAGCCGGTGA GCGTGGGTCT CGCGGTATCA | 6300 |
| TTGCAGCACT GGGGCCAGAT GGTAAGCCCT CCCGTATCGT AGTTATCTAC | 6350 |
| ACGACGGGGA GTCAGGCAAC TATGGATGAA CGAAATAGAC AGATCGCTGA | 6400 |
| GATAGGTGCC TCACTGATTA AGCATTGGTA ACTGTCAGAC CAAGTTTACT | 6450 |
| CATATATACT TTAGATTGAT TTAAAACTTC ATTTTTAATT TAAAAGGATC | 6500 |
| TAGGTGAAGA TCCTTTTTGA TAATCTCATG ACCAAAATCC CTTAACGTGA | 6550 |
| GTTTTCGTTC CACTGAGCGT CAGACCCCGT AGAAAAGATC AAAGGATCTT | 6600 |

| | |
|---|---:|
| CTTGAGATCC TTTTTTTCTG CGCGTAATCT GCTGCTTGCA AACAAAAAAA | 6650 |
| CCACCGCTAC CAGCGGTGGT TTGTTTGCCG GATCAAGAGC TACCAACTCT | 6700 |
| TTTTCCGAAG GTAACTGGCT TCAGCAGAGC GCAGATACCA AATACTGTTC | 6750 |
| TTCTAGTGTA GCCGTAGTTA GGCCACCACT TCAAGAACTC TGTAGCACCG | 6800 |
| CCTACATACC TCGCTCTGCT AATCCTGTTA CCAGTGGCTG CTGCCAGTGG | 6850 |
| CGATAAGTCG TGTCTTACCG GGTTGGACTC AAGACGATAG TTACCGGATA | 6900 |
| AGGCGCAGCG GTCGGGCTGA ACGGGGGGTT CGTGCACACA GCCCAGCTTG | 6950 |
| GAGCGAACGA CCTACACCGA ACTGAGATAC CTACAGCGTG AGCTATGAGA | 7000 |
| AAGCGCCACG CTTCCCGAAG GGAGAAAGGC GGACAGGTAT CCGGTAAGCG | 7050 |
| GCAGGGTCGG AACAGGAGAG CGCACGAGGG AGCTTCCAGG GGGAAACGCC | 7100 |
| TGGTATCTTT ATAGTCCTGT CGGGTTTCGC CACCTCTGAC TTGAGCGTCG | 7150 |
| ATTTTTGTGA TGCTCGTCAG GGGGGCGGAG CCTATGGAAA AACGCCAGCA | 7200 |
| ACGCGGCCTT TTTACGGTTC CTGGCCTTTT GCTGGCCTTT TGCTCACATG | 7250 |
| TTCTTTCCTG CGTTATCCCC TGATTCTGTG GATAACCGTA TTACCGCCTT | 7300 |
| TGAGTGAGCT GATACCGCTC GCCGCAGCCG AACGACCGAG CGCAGCGAGT | 7350 |
| CAGTGAGCGA GGAAGCGGAA GAGCGCCCAA TACGCAAACC GCCTCTCCCC | 7400 |
| GCGCGTTGGC CGATTCATTA ATGCAGCTGG CACGACAGGT TTCCCGACTG | 7450 |
| GAAAGCGGGC AGTGAGCGCA ACGCAATTAA TGTGAGTTAG CTCACTCATT | 7500 |
| AGGCACCCCA GGCTTTACAC TTTATGCTTC CGGCTCGTAT GTTGTGTGGA | 7550 |
| ATTGTGAGCG GATAACAATT TCACACAGGA AACAGCTATG ACATGATTAC | 7600 |
| GAATTAA | 7607 |

(2) INFORMATION FOR SEQ ID NO:20:

(i) SEQUENCE CHARACTERISTICS:
        (A) LENGTH: 505 amino acids
        (B) TYPE: Amino Acid
        (D) TOPOLOGY: Linear (xi) SEQUENCE DESCRIPTION: SEQ ID NO:20:

```
Met Ser Asn Ile Cys Gln Arg Leu Trp Glu Tyr Leu Glu Pro Tyr
 1               5                  10                  15

Leu Pro Cys Leu Ser Thr Glu Ala Asp Lys Ser Thr Val Ile Glu
                20                  25                  30

Asn Pro Gly Ala Leu Cys Ser Pro Gln Ser Gln Arg His Gly His
                35                  40                  45

Tyr Phe Val Ala Leu Phe Asp Tyr Gln Ala Arg Thr Ala Glu Asp
                50                  55                  60

Leu Ser Phe Arg Ala Gly Asp Lys Leu Gln Val Leu Asp Thr Leu
                65                  70                  75

His Glu Gly Trp Trp Phe Ala Arg His Leu Glu Lys Arg Arg Asp
                80                  85                  90

Gly Ser Ser Gln Gln Leu Gln Gly Tyr Ile Pro Ser Asn Tyr Val
                95                  100                 105

Ala Glu Asp Arg Ser Leu Gln Ala Glu Pro Trp Phe Phe Gly Ala
                110                 115                 120

Ile Gly Arg Ser Asp Ala Glu Lys Gln Leu Leu Tyr Ser Glu Asn
                125                 130                 135
```

-continued

```
Lys Thr Gly Ser Phe Leu Ile Arg Glu Ser Glu Ser Gln Lys Gly
            140                 145                 150

Glu Phe Ser Leu Ser Val Leu Asp Gly Ala Val Val Lys His Tyr
            155                 160                 165

Arg Ile Lys Arg Leu Asp Glu Gly Gly Phe Phe Leu Thr Arg Arg
            170                 175                 180

Arg Ile Phe Ser Thr Leu Asn Glu Phe Val Ser His Tyr Thr Lys
            185                 190                 195

Thr Ser Asp Gly Leu Cys Val Lys Leu Gly Lys Pro Cys Leu Lys
            200                 205                 210

Ile Gln Val Pro Ala Pro Phe Asp Leu Ser Tyr Lys Thr Val Asp
            215                 220                 225

Gln Trp Glu Ile Asp Arg Asn Ser Ile Gln Leu Leu Lys Arg Leu
            230                 235                 240

Gly Ser Gly Gln Phe Gly Glu Val Trp Glu Gly Leu Trp Asn Asn
            245                 250                 255

Thr Thr Pro Val Ala Val Lys Thr Leu Lys Pro Gly Ser Met Asp
            260                 265                 270

Pro Asn Asp Phe Leu Arg Glu Ala Gln Ile Met Lys Asn Leu Arg
            275                 280                 285

His Pro Lys Leu Ile Gln Leu Tyr Ala Val Cys Thr Leu Glu Asp
            290                 295                 300

Pro Ile Tyr Ile Ile Thr Glu Leu Met Arg His Gly Ser Leu Gln
            305                 310                 315

Glu Tyr Leu Gln Asn Asp Thr Gly Ser Lys Ile His Leu Thr Gln
            320                 325                 330

Gln Val Asp Met Ala Ala Gln Val Ala Ser Gly Met Ala Tyr Leu
            335                 340                 345

Glu Ser Arg Asn Tyr Ile His Arg Asp Leu Ala Ala Arg Asn Val
            350                 355                 360

Leu Val Gly Glu His Asn Ile Tyr Lys Val Ala Asp Phe Gly Leu
            365                 370                 375

Ala Arg Val Phe Lys Val Asp Asn Glu Asp Ile Tyr Glu Ser Arg
            380                 385                 390

His Glu Ile Lys Leu Pro Val Lys Trp Thr Ala Pro Glu Ala Ile
            395                 400                 405

Arg Ser Asn Lys Phe Ser Ile Lys Ser Asp Val Trp Ser Phe Gly
            410                 415                 420

Ile Leu Leu Tyr Glu Ile Ile Thr Tyr Gly Lys Met Pro Tyr Ser
            425                 430                 435

Gly Met Thr Gly Ala Gln Val Ile Gln Met Leu Ala Gln Asn Tyr
            440                 445                 450

Arg Leu Pro Gln Pro Ser Asn Cys Pro Gln Gln Phe Tyr Asn Ile
            455                 460                 465

Met Leu Glu Cys Trp Asn Ala Glu Pro Lys Glu Arg Pro Thr Phe
            470                 475                 480

Glu Thr Leu Arg Trp Lys Leu Glu Asp Tyr Phe Glu Thr Asp Ser
            485                 490                 495

Ser Tyr Ser Asp Ala Asn Asn Phe Ile Arg
            500                 505
```

(2) INFORMATION FOR SEQ ID NO:21:

(i) SEQUENCE CHARACTERISTICS:
            (A) LENGTH: 404 base pairs
            (B) TYPE: Nucleic Acid
            (C) STRANDEDNESS: Single
            (D) TOPOLOGY: Linear (xi) SEQUENCE DESCRIPTION: SEQ ID NO:21:

| | | |
|---|---|---|
| GCGGCCGCAG AGAAAGCAGA GGATGGGGCT TAGCAGCTGG CAGAGCCAGG | 50 |
| AGCGGGGAGG TAGCAGAAAG ACCACAAGTA CAAAGAAGTC CTGAAACTTT | 100 |
| GGTTTTGCTG CTGCAGCCCA TTGAGAGTGA CGACATGGAG CACAAGACCC | 150 |
| TGAAGATCAC CGACTTTGGC CTGGCCCGAG AGTGGCACAA AACCACACAA | 200 |
| ATGAGTGCCG CNGGCACCTA CNCCTGGATG GCTCCTGAGG TTATCAAGGC | 250 |
| CTCCACCTTC TCTAAGGGCA GTGACGTCTG GAGTTTTGGG GTGCTGCTGT | 300 |
| GGGAACTGCT GACCGGGGAG NTGCCATACC GTGGCATTGA CTGCCTTGCT | 350 |
| GTGGCCTATG GCGTAGCTGT TAACAAGCTC ACACTGCCAT CCATCCACCT | 400 |
| GGCC | 404 |

(2) INFORMATION FOR SEQ ID NO:22:

(i) SEQUENCE CHARACTERISTICS:
            (A) LENGTH: 3120 base pairs
            (B) TYPE: Nucleic Acid
            (C) STRANDEDNESS: Single
            (D) TOPOLOGY: Linear (xi) SEQUENCE DESCRIPTION: SEQ ID NO:22:

| | |
|---|---|
| ATGAGAGCGT TGGCGCGCGA CGGCGGCCAG CTGCCGCTGC TCGTTGTTTT | 50 |
| TTCTGCAATG ATATTTGGGA CTATTACAAA TCAAGATCTG CCTGTGATCA | 100 |
| AGTGTGTTTT AATCAATCAT AAGAACAATG ATTCATCAGT GGGGAAGTCA | 150 |
| TCATCATATC CCATGGTATC AGAATCCCCG GAAGACCTCG GGTGTGCGTT | 200 |
| GAGACCCCAG AGCTCAGGGA CAGTGTACGA AGCTGCCGCT GTGGAAGTGG | 250 |
| ATGTATCTGC TTCCATCACA CTGCAAGTGC TGGTCGATGC CCCAGGGAAC | 300 |
| ATTTCCTGTC TCTGGGTCTT TAAGCACAGC TCCCTGAATT GCCAGCCACA | 350 |
| TTTTGATTTA CAAAACAGAG GAGTTGTTTC CATGGTCATT TTGAAAATGA | 400 |
| CAGAAACCCA AGCTGGAGAA TACCTACTTT TTATTCAGAG TGAAGCTACC | 450 |
| AATTACACAA TATTGTTTAC AGTGAGTATA AGAAATACCC TGCTTTACAC | 500 |
| ATTAAGAAGA CCTTACTTTA GAAAAATGGA AAACCAGGAC GCCCTGGTCT | 550 |
| GCATATCTGA GAGCGTTCCA GAGCGGATCC TGGAATGGGT GCTTTGCGAT | 600 |
| TCACAGGGGG AAAGCTGTAA AGAAGAAAGT CCAGCTGTTG TTAAAAAGGA | 650 |
| GGAAAAAGTG CTTCATGAAT TATTTGGGAC GGACATAAGG TGCTGTGCCA | 700 |
| GAAATGAACT GGGCAGGGAA TGCACCAGGC TGTTCACAAT AGATCTAAAT | 750 |
| CAAACTCCTC AGACCACATT GCCACAATTA TTTCTTAAAG TAGGGGAACC | 800 |
| CTTATGGATA AGGTGCAAAG CTGTTCATGT GAACCATGGA TTCGGGCTCA | 850 |
| CCTGGGAATT AGAAAACAAA GCACTCGAGG AGGGCAACTA CTTTGAGATG | 900 |
| AGTACCTATT CAACAAACAG AACTATGATA CGGATTCTGT TTGCTTTTGT | 950 |
| ATCATCAGTG GCAAGAAACG ACACCGGATA CTACACTTGT TCCTCTTCAA | 1000 |
| AGCATCCCAG TCAATCAGCT TTGGTTACCA TCGTAGAAAA GGGATTTATA | 1050 |

```
AATGCTACCA ATTCAAGTGA AGATTATGAA ATTGACCAAT ATGAAGAGTT    1100

TTGTTTTTCT GTCAGGTTTA AAGCCTACCC ACAAATCAGA TGTACGTGGA    1150

CCTTCTCTCG AAAATCATTT CCTTGTGAGC AAAAGGGTCT TGATAACGGA    1200

TACAGCATAT CCAAGTTTTG CAATCATAAG CACCAGCCAG GAGAATATAT    1250

ATTCCATGCA GAAAATGATG ATGCCCAATT TACCAAAATG TTCACGCTGT    1300

ATATAAGAAG GAAACCTCAA GTCCTCGCAG AAGCTTCGGC AAGTCAGGCG    1350

TCCTGTTTCT CGGATGGATA CCCATTACCA TCTTGGACCT GGAAGAAGTG    1400

TTCAGACAAG TCTCCCAACT GCACAGAAGA GATCACAGAA GGAGTCTGGA    1450

ATAGAAAGGC TAACAGAAAA GTGTTTGGAC AGTGGGTGTC GAGCAGTACT    1500

CTAAACATGA GTGAAGCCAT AAAAGGGTTC CTGGTCAAGT GCTGTGCATA    1550

CAATTCCCTT GGCACATCTT GTGAGACGAT CCTTTTAAAC TCTCCAGGCC    1600

CCTTCCCTTT CATCCAAGAC AACATCTCAT TCTATGCAAC AATTGGTGTT    1650

TGTCTCCTCT TCATTGTCGT TTTAACCCTG CTAATTTGTC ACAAGTACAA    1700

AAAGCAATTT AGGTATGAAA GCCAGCTACA GATGGTACAG GTGACCGGAT    1750

CCTCAGATTA TGAGTACTTC TACGTTGATT TCAGAGAATA TGAATATGAT    1800

GTCAAATGGG AGTTTCCAAG AGAAAATTTA GAGTTTGGGA AGGTACTAGG    1850

ATCAGGTGCT TTTGGAAAAG TGATGAACGC AACAGCTTAT GGAATTAGCA    1900

AAACAGGAGT CTCAATCCAG GTTACCGTCA AAATGCTGAA AGAAAAAGCA    1950

GACAGCTCTG AAAGAGAGGC ACTCATGTCA GAACTCAAGA TGATGACCCA    2000

GCTGGGAAGC CACGAGAATA TTGTGAACCT GCTGGGGGCG TGCACACTGT    2050

CAGGACCAAT TTACTTGATT TTTGAATACT GTTGCTATGG TGATCTTCTC    2100

AACTATCTAA GAAGTAAAAG AGAAAAATTT CACAGGACTT GGACAGAGAT    2150

TTTCAAGGAA CACAATTTCA GTTTTTACCC CACTTTCCAA TCACATCCAA    2200

ATTCCAGCAT GCCTGGTTCA AGAGAAGTTC AGATACACCC GGACTCGGAT    2250

CAAATCTCAG GGCTTCATGG GAATTCATTT CACTCTGAAG ATGAAATTGA    2300

ATATGAAAAC CAAAAAAGGC TGGAAGAAGA GGAGGACTTG AATGTGCTTA    2350

CATTTGAAGA TCTTCTTTGC TTTGCATATC AAGTTGCCAA AGGAATGGAA    2400

TTTCTGGAAT TTAAGTCGTG TGTTCACAGA GACCTGGCCG CCAGGAACGT    2450

GCTTGTCACC CACGGGAAAG TGGTGAAGAT ATGTGACTTT GGATTGGCTC    2500

GAGATATCAT GAGTGATTCC AACTATGTTG TCAGGGGCAA TGCCCGTCTG    2550

CCTGTAAAAT GGATGGCCCC CGAAAGCCTG TTTGAAGGCA TCTACACCAT    2600

TAAGAGTGAT GTCTGGTCAT ATGGAATATT ACTGTGGGAA ATCTTCTCAC    2650

TTGGTGTGAA TCCTTACCCT GGCATTCCGG TTGATGCTAA CTTCTACAAA    2700

CTGATTCAAA ATGGATTTAA AATGGATCAG CCATTTATG CTACAGAAGA    2750

AATATACATT ATAATGCAAT CCTGCTGGGC TTTTGACTCA AGGAAACGGC    2800

CATCCTTCCC TAATTTGACT TCGTTTTTAG GATGTCAGCT GGCAGATGCA    2850

GAAGAAGCGA TGTATCAGAA TGTGGATGGC CGTGTTTCGG AATGTCCTCA    2900

CACCTACCAA AACAGGCGAC CTTTCAGCAG AGAGATGGAT TTGGGGCTAC    2950

TCTCTCCGCA GGCTCAGGTC GAAGATTCGT AGAGGAACAA TTTAGTTTTA    3000

AGGACTTCAT CCCTCCACCT ATCCCTAACA GGCTGTAGAT TACCAAAACA    3050
```

AGGTTAATTT CATCACTAAA AGAAAATCTA TTATCAACTG CTGCTTCACC      3100

AGACTTTTCT CTAGAGAGCG      3120

(2) INFORMATION FOR SEQ ID NO:23:

(i) SEQUENCE CHARACTERISTICS:
        (A) LENGTH: 3969 base pairs
        (B) TYPE: Nucleic Acid
        (C) STRANDEDNESS: Single
        (D) TOPOLOGY: Linear (xi) SEQUENCE DESCRIPTION: SEQ ID NO:23:

TCGGCGTCCA CCCGCCCAGG GAGAGTCAGA CCTGGGGGGG CGAGGGCCCC      50

CCAAACTCAG TTCGGATCCT ACCCGAGTGA GGCGGCGCCA TGGAGCTCCG      100

GGTGCTGCTC TGCTGGGCTT CGTTGGCCGC AGCTTTGGAA GAGACCCTGC      150

TGAACACAAA ATTGGAAACT GCTGATCTGA AGTGGGTGAC ATTCCCTCAG      200

GTGGACGGGC AGTGGGAGGA ACTGAGCGGC CTGGATGAGG AACAGCACAG      250

CGTGCGCACC TACGAAGTGT GTGACGTGCA GCGTGCCCCG GGCCAGGCCC      300

ACTGGCTTCG CACAGGTTGG GTCCCACGGC GGGGCGCCGT CCACGTGTAC      350

GCCACGCTGC GCTTCACCAT GCTCGAGTGC CTGTCCCTGC CTCGGGCTGG      400

GCGCTCCTGC AAGGAGACCT TCACCGTCTT CTACTATGAG AGCGATGCGG      450

ACACGGCCAC GGCCCTCACG CCAGCCTGGA TGGAGAACCC CTACATCAAG      500

GTGGACACGG TGGCCGCGGA GCATCTCACC CGGAAGCGCC CTGGGGCCGA      550

GGCCACCGGG AAGGTGAATG TCAAGACGCT GCGTCTGGGA CCGCTCAGCA      600

AGGCTGGCTT CTACCTGGCC TTCCAGGACC AGGGTGCCTG CATGGCCCTG      650

CTATCCCTGC ACCTCTTCTA CAAAAAGTGC GCCCAGCTGA CTGTGAACCT      700

GACTCGATTC CCGGAGACTG TGCCTCGGGA GCTGGTTGTG CCCGTGGCCG      750

GTAGCTGCGT GGTGGATGCC GTCCCCGCCC CTGGCCCCAG CCCCAGCCTC      800

TACTGCCGTG AGGATGGCCA GTGGGCCGAA CAGCCGGTCA CGGGCTGCAG      850

CTGTGCTCCG GGGTTCGAGG CAGCTGAGGG GAACACCAAG TGCCGAGCCT      900

GTGCCCAGGG CACCTTCAAG CCCCTGTCAG GAGAAGGGTC CTGCCAGCCA      950

TGCCCAGCCA ATAGCCACTC TAACACCATT GGATCAGCCG TCTGCCAGTG      1000

CCGCGTCGGG TACTTCCGGG CACGCACAGA CCCCCGGGGT GCACCCTGCA      1050

CCACCCCTCC TTCGGCTCCG CGGAGCGTGG TTTCCCGCCT GAACGGCTCC      1100

TCCCTGCACC TGGAATGGAG TGCCCCCCTG GAGTCTGGTG GCCGAGAGGA      1150

CCTCACCTAC GCCCTCCGCT GCCGGGAGTG CCGACCCGGA GGCTCCTGTG      1200

CGCCCTGCGG GGGAGACCTG ACTTTTGACC CCGGCCCCCG GGACCTGGTG      1250

GAGCCCTGGG TGGTGGTTCG AGGGCTACGT CCTGACTTCA CCTATACCTT      1300

TGAGGTCACT GCATTGAACG GGTATCCTC CTTAGCCACG GGGCCCGTCC      1350

CATTTGAGCC TGTCAATGTC ACCACTGACC GAGAGGTACC TCCTGCAGTG      1400

TCTGACATCC GGGTGACGCG GTCCTCACCC AGCAGCTTGA GCCTGGCCTG      1450

GGCTGTTCCC CGGGCACCCA GTGGGGCTGT GCTGGACTAC GAGGTCAAAT      1500

ACCATGAGAA GGGCGCCGAG GGTCCCAGCA GCGTGCGGTT CCTGAAGACG      1550

TCAGAAAACC GGGCAGAGCT GCGGGGGCTG AAGCGGGGAG CCAGCTACCT      1600

-continued

| | |
|---|---|
| GGTGCAGGTA CGGGCGCGCT CTGAGGCCGG CTACGGGCCC TTCGGCCAGG | 1650 |
| AACATCACAG CCAGACCCAA CTGGATGAGA GCGAGGGCTG GCGGGAGCAG | 1700 |
| CTGGCCCTGA TTGCGGGCAC GGCAGTCGTG GGTGTGGTCC TGGTCCTGGT | 1750 |
| GGTCATTGTG GTCGCAGTTC TCTGCCTCAG GAAGCAGAGC AATGGGAGAG | 1800 |
| AAGCAGAATA TTCGGACAAA CACGGACAGT ATCTCATCGG ACATGGTACT | 1850 |
| AAGGTCTACA TCGACCCCTT CACTTATGAA GACCCTAATG AGGCTGTGAG | 1900 |
| GGAATTTGCA AAAGAGATCG ATGTCTCCTA CGTCAAGATT GAAGAGGTGA | 1950 |
| TTGGTGCAGG TGAGTTTGGC GAGGTGTGCC GGGGGCGGCT CAAGGCCCCA | 2000 |
| GGGAAGAAGG AGAGCTGTGT GGCAATCAAG ACCCTGAAGG GTGGCTACAC | 2050 |
| GGAGCGGCAG CGGCGTGAGT TTCTGAGCGA GGCCTCCATC ATGGGCCAGT | 2100 |
| TCGAGCACCC CAATATCATC CGCCTGGAGG GCGTGGTCAC CAACAGCATG | 2150 |
| CCCGTCATGA TTCTCACAGA GTTCATGGAG AACGGCGCCC TGGACTCCTT | 2200 |
| CCTGCGGCTA AACGACGGAC AGTTCACAGT CATCCAGCTC GTGGGCATGC | 2250 |
| TGCGGGCAT CGCCTCGGGC ATGCGGTACC TTGCCGAGAT GAGCTACGTC | 2300 |
| CACCGAGACC TGGCTGCTCG CAACATCCTA GTCAACAGCA ACCTCGTCTG | 2350 |
| CAAAGTGTCT GACTTTGGCC TTTCCCGATT CCTGGAGGAG AACTCTTCCG | 2400 |
| ATCCCACCTA CACGAGCTCC CTGGGAGGAA AGATTCCCAT CCGATGGACT | 2450 |
| GCCCCGGAGG CCATTGCCTT CCGGAAGTTC ACTTCCGCCA GTGATGCCTG | 2500 |
| GAGTTACGGG ATTGTGATGT GGGAGGTGAT GTCATTTGGG GAGAGGCCGT | 2550 |
| ACTGGGACAT GAGCAATCAG GACGTGATCA ATGCCATTGA ACAGGACTAC | 2600 |
| CGGCTGCCCC CGCCCCCAGA CTGTCCCACC TCCCTCCACC AGCTCATGCT | 2650 |
| GGACTGTTGG CAGAAAGACC GGAATGCCCG GCCCCGCTTC CCCCAGGTGG | 2700 |
| TCAGCGCCCT GGACAAGATG ATCCGGAACC CCGCCAGCCT CAAAATCGTG | 2750 |
| GCCCGGGAGA ATGGCGGGGC CTCACACCCT CTCCTGGACC AGCGGCAGCC | 2800 |
| TCACTACTCA GCTTTTGGCT CTGTGGGCGA GTGGCTTCGG GCCATCAAAA | 2850 |
| TGGGAAGATA CGAAGAAAGT TTCGCAGCCG CTGGCTTTGG CTCCTTCGAG | 2900 |
| CTGGTCAGCC AGATCTCTGC TGAGGACCTG CTCCGAATCG GAGTCACTCT | 2950 |
| GGCGGGACAC CAGAAGAAAA TCTTGGCCAG TGTCCAGCAC ATGAAGTCCC | 3000 |
| AGGCCAAGCC GGGAACCCCG GGTGGGACAG GAGGACCGGC CCCGCAGTAC | 3050 |
| TGACCTGCAG GAACTCCCCA CCCCAGGGAC ACCGCCTCCC CATTTTCCGG | 3100 |
| GGCAGAGTGG GGACTCACAG AGGCCCCCAG CCCTGTGCCC CGCTGGATTG | 3150 |
| CACTTTGAGC CCGTGGGGTG AGGAGTTGGC AATTGGAGA GACAGGATTT | 3200 |
| GGGGGTTCTG CCATAATAGG AGGGGAAAAT CACCCCCCAG CCACCTCGGG | 3250 |
| GAACTCCAGA CCAAGGGTGA GGGCGCCTTT CCCTCAGGAC TGGGTGTGAC | 3300 |
| CAGAGGAAAA GGAAGTGCCC AACATCTCCC AGCCTCCCCA GGTGCCCCCC | 3350 |
| TCACCTTGAT GGGTGCGTTC CCGCAGACCA AAGAGAGTGT GACTCCCTTG | 3400 |
| CCAGCTCCAG AGTGGGGGGG CTGTCCCAGG GGGCAAGAAG GGGTGTCAGG | 3450 |
| GCCCAGTGAC AAAATCATTG GGGTTTGTAG TCCCAACTTG CTGCTGTCAC | 3500 |
| CACCAAACTC AATCATTTTT TTCCCTTGTA AATGCCCCTC CCCCAGCTGC | 3550 |

-continued

```
TGCCTTCATA TTGAAGGTTT TTGAGTTTTG TTTTTGGTCT TAATTTTTCT    3600

CCCCGTTCCC TTTTTGTTTC TTCGTTTTGT TTTTCTACCG TCCTTGTCAT    3650

AACTTTGTGT TGGAGGGAAC CTGTTTCACT ATGGCCTCCT TTGCCCAAGT    3700

TGAAACAGGG GCCCATCATC ATGTCTGTTT CCAGAACAGT GCCTTGGTCA    3750

TCCCACATCC CCGGACCCCG CCTGGGACCC CCAAGCTGTG TCCTATGAAG    3800

GGGTGTGGGG TGAGGTAGTG AAAAGGGCGG TAGTTGGTGG TGGAACCCAG    3850

AAACGGACGC CGGTGCTTGG AGGGGTTCTT AAATTATATT TAAAAAAGTA    3900

ACTTTTTGTA TAAATAAAAG AAAATGGGAC GTGTCCCAGC TCCAGGGGTA    3950

AAAAAAAAAA AAAAAAAA                                       3969
```

(2) INFORMATION FOR SEQ ID NO:24:

(i) SEQUENCE CHARACTERISTICS:
        (A) LENGTH: 1276 amino acids
        (B) TYPE: Amino Acid
        (D) TOPOLOGY: Linear (xi) SEQUENCE DESCRIPTION: SEQ ID NO:24:

```
Met Glu Leu Arg Val Leu Leu Cys Trp Ala Ser Leu Ala Ala Ala
 1               5                  10                  15

Leu Glu Glu Thr Leu Leu Asn Thr Lys Leu Glu Thr Ala Asp Leu
                20                  25                  30

Lys Trp Val Thr Phe Pro Gln Val Asp Gly Gln Trp Glu Glu Leu
                35                  40                  45

Ser Gly Leu Asp Glu Glu Gln His Ser Val Arg Thr Tyr Glu Val
                50                  55                  60

Cys Asp Val Gln Arg Ala Pro Gly Gln Ala His Trp Leu Arg Thr
                65                  70                  75

Gly Trp Val Pro Arg Arg Gly Ala Val His Val Tyr Ala Thr Leu
                80                  85                  90

Arg Phe Thr Met Leu Glu Cys Leu Ser Leu Pro Arg Ala Gly Arg
                95                 100                 105

Ser Cys Lys Glu Thr Phe Thr Val Phe Tyr Tyr Glu Ser Asp Ala
               110                 115                 120

Asp Thr Ala Thr Ala Leu Thr Pro Ala Trp Met Glu Asn Pro Tyr
               125                 130                 135

Ile Lys Val Asp Thr Val Ala Ala Glu His Leu Thr Arg Lys Arg
               140                 145                 150

Pro Gly Ala Glu Ala Thr Gly Lys Val Asn Val Lys Thr Leu Arg
               155                 160                 165

Leu Gly Pro Leu Ser Lys Ala Gly Phe Tyr Leu Ala Phe Gln Asp
               170                 175                 180

Gln Gly Ala Cys Met Ala Leu Leu Ser Leu His Leu Phe Tyr Lys
               185                 190                 195

Lys Cys Ala Gln Leu Thr Val Asn Leu Thr Arg Phe Pro Glu Thr
               200                 205                 210

Val Pro Arg Glu Leu Val Val Pro Val Ala Gly Ser Cys Val Val
               215                 220                 225

Asp Ala Val Pro Ala Pro Gly Pro Ser Pro Ser Leu Tyr Cys Arg
               230                 235                 240

Glu Asp Gly Gln Trp Ala Glu Gln Pro Val Thr Gly Cys Ser Cys
               245                 250                 255
```

-continued

```
Ala Pro Gly Phe Glu Ala Ala Glu Gly Asn Thr Lys Cys Arg Ala
                260                 265                 270

Cys Ala Gln Gly Thr Phe Lys Pro Leu Ser Gly Glu Gly Ser Cys
            275                 280                 285

Gln Pro Cys Pro Ala Asn Ser His Ser Asn Thr Ile Gly Ser Ala
        290                 295                 300

Val Cys Gln Cys Arg Val Gly Tyr Phe Arg Ala Arg Thr Asp Pro
    305                 310                 315

Arg Gly Ala Pro Cys Thr Thr Pro Pro Ser Ala Pro Arg Ser Val
320                 325                 330

Val Ser Arg Leu Asn Gly Ser Ser Leu His Leu Glu Trp Ser Ala
                335                 340                 345

Pro Leu Glu Ser Gly Gly Arg Glu Asp Leu Thr Tyr Ala Leu Arg
            350                 355                 360

Cys Arg Glu Cys Arg Pro Gly Gly Ser Cys Ala Pro Cys Gly Gly
        365                 370                 375

Asp Leu Thr Phe Asp Pro Gly Pro Arg Asp Leu Val Glu Pro Trp
    380                 385                 390

Val Val Val Arg Gly Leu Arg Pro Asp Phe Thr Tyr Thr Phe Glu
395                 400                 405

Val Thr Ala Leu Asn Gly Val Ser Ser Leu Ala Thr Gly Pro Val
                410                 415                 420

Pro Phe Glu Pro Val Asn Val Thr Thr Asp Arg Glu Val Pro Pro
            425                 430                 435

Ala Val Ser Asp Ile Arg Val Thr Arg Ser Ser Pro Ser Ser Leu
        440                 445                 450

Ser Leu Ala Trp Ala Val Pro Arg Ala Pro Ser Gly Ala Val Leu
    455                 460                 465

Asp Tyr Glu Val Lys Tyr His Glu Lys Gly Ala Glu Gly Pro Ser
470                 475                 480

Ser Val Arg Phe Leu Lys Thr Ser Glu Asn Arg Ala Glu Leu Arg
                485                 490                 495

Gly Leu Lys Arg Gly Ala Ser Tyr Leu Val Gln Val Arg Ala Arg
            500                 505                 510

Ser Glu Ala Gly Tyr Gly Pro Phe Gly Gln Glu His His Ser Gln
        515                 520                 525

Thr Gln Leu Asp Glu Ser Glu Gly Trp Arg Glu Gln Leu Ala Leu
    530                 535                 540

Ile Ala Gly Thr Ala Val Val Gly Val Val Leu Val Leu Val Val
545                 550                 555

Ile Val Val Ala Val Leu Cys Leu Arg Lys Gln Ser Asn Gly Arg
                560                 565                 570

Glu Ala Glu Tyr Ser Asp Lys His Gly Gln Tyr Leu Ile Gly His
            575                 580                 585

Gly Thr Lys Val Tyr Ile Asp Pro Phe Thr Tyr Glu Asp Pro Asn
        590                 595                 600

Glu Ala Val Arg Glu Phe Ala Lys Glu Ile Asp Val Ser Tyr Val
    605                 610                 615

Lys Ile Glu Glu Val Ile Gly Ala Gly Glu Phe Gly Glu Val Cys
620                 625                 630

Arg Gly Arg Leu Lys Ala Pro Gly Lys Lys Glu Ser Cys Val Ala
                635                 640                 645

Ile Lys Thr Leu Lys Gly Gly Tyr Thr Glu Arg Gln Arg Arg Glu
```

-continued

```
                650                 655                 660
Phe Leu Ser Glu Ala Ser Ile Met Gly Gln Phe Glu His Pro Asn
                665                 670                 675
Ile Ile Arg Leu Glu Gly Val Val Thr Asn Ser Met Pro Val Met
                680                 685                 690
Ile Leu Thr Glu Phe Met Glu Asn Gly Ala Leu Asp Ser Phe Leu
                695                 700                 705
Arg Leu Asn Asp Gly Gln Phe Thr Val Ile Gln Leu Val Gly Met
                710                 715                 720
Leu Arg Gly Ile Ala Ser Gly Met Arg Tyr Leu Ala Glu Met Ser
                725                 730                 735
Tyr Val His Arg Asp Leu Ala Ala Arg Asn Ile Leu Val Asn Ser
                740                 745                 750
Asn Leu Val Cys Lys Val Ser Asp Phe Gly Leu Ser Arg Phe Leu
                755                 760                 765
Glu Glu Asn Ser Ser Asp Pro Thr Tyr Thr Ser Ser Leu Gly Gly
                770                 775                 780
Lys Ile Pro Ile Arg Trp Thr Ala Pro Glu Ala Ile Ala Phe Arg
                785                 790                 795
Lys Phe Thr Ser Ala Ser Asp Ala Trp Ser Tyr Gly Ile Val Met
                800                 805                 810
Trp Glu Val Met Ser Phe Gly Glu Arg Pro Tyr Trp Asp Met Ser
                815                 820                 825
Asn Gln Asp Val Ile Asn Ala Ile Glu Gln Asp Tyr Arg Leu Pro
                830                 835                 840
Pro Pro Pro Asp Cys Pro Thr Ser Leu His Gln Leu Met Leu Asp
                845                 850                 855
Cys Trp Gln Lys Asp Arg Asn Ala Arg Pro Arg Phe Pro Gln Val
                860                 865                 870
Val Ser Ala Leu Asp Lys Met Ile Arg Asn Pro Ala Ser Leu Lys
                875                 880                 885
Ile Val Ala Arg Glu Asn Gly Gly Ala Ser His Pro Leu Leu Asp
                890                 895                 900
Gln Arg Gln Pro His Tyr Ser Ala Phe Gly Ser Val Gly Glu Trp
                905                 910                 915
Leu Arg Ala Ile Lys Met Gly Arg Tyr Glu Glu Ser Phe Ala Ala
                920                 925                 930
Ala Gly Phe Gly Ser Phe Glu Leu Val Ser Gln Ile Ser Ala Glu
                935                 940                 945
Asp Leu Leu Arg Ile Gly Val Thr Leu Ala Gly His Gln Lys Lys
                950                 955                 960
Ile Leu Ala Ser Val Gln His Met Lys Ser Gln Ala Lys Pro Gly
                965                 970                 975
Thr Pro Gly Gly Thr Gly Gly Pro Ala Pro Gln Tyr Pro Ala Gly
                980                 985                 990
Thr Pro His Pro Arg Asp Thr Ala Ser Pro Phe Ser Gly Ala Glu
                995                1000                1005
Trp Gly Leu Thr Glu Ala Pro Ser Pro Val Pro Arg Trp Ile Ala
               1010                1015                1020
Leu Ala Arg Gly Val Arg Ser Trp Gln Phe Gly Glu Thr Gly Phe
               1025                1030                1035
Gly Gly Ser Ala Ile Ile Gly Gly Glu Asn His Pro Pro Ala Thr
               1040                1045                1050
```

-continued

Ser Gly Asn Ser Arg Pro Arg Val Arg Ala Pro Phe Pro Gln Asp
              1055                1060                1065

Trp Val Pro Glu Glu Lys Glu Val Pro Asn Ile Ser Gln Pro Pro
              1070                1075                1080

Gln Val Pro Pro Ser Pro Trp Val Arg Ser Arg Arg Pro Lys Arg
              1085                1090                1095

Val Leu Pro Cys Gln Leu Gln Ser Gly Gly Ala Val Pro Gly Gly
              1100                1105                1110

Lys Lys Gly Cys Gln Gly Pro Val Thr Lys Ser Leu Gly Phe Val
              1115                1120                1125

Val Pro Thr Cys Cys His His Gln Thr Gln Ser Phe Phe Ser
              1130                1135                1140

Leu Val Asn Ala Pro Pro Pro Ala Ala Ala Phe Ile Leu Lys Val
              1145                1150                1155

Phe Glu Phe Cys Phe Trp Ser Phe Phe Ser Pro Phe Pro Phe Cys
              1160                1165                1170

Phe Phe Val Leu Phe Phe Tyr Arg Pro Cys His Asn Phe Val Leu
              1175                1180                1185

Glu Gly Thr Cys Phe Thr Met Ala Ser Phe Ala Gln Val Glu Thr
              1190                1195                1200

Gly Ala His His His Val Cys Phe Gln Asn Ser Ala Leu Val Ile
              1205                1210                1215

Pro His Pro Arg Thr Pro Pro Gly Thr Pro Lys Leu Cys Pro Met
              1220                1225                1230

Lys Gly Cys Gly Val Arg Lys Gly Arg Leu Val Val Glu Pro Arg
              1235                1240                1245

Asn Gly Arg Arg Cys Leu Glu Gly Phe Leu Asn Tyr Ile Lys Ser
              1250                1255                1260

Asn Phe Leu Tyr Lys Lys Lys Met Gly Arg Val Pro Ala Pro Gly
              1265                1270                1275

Val
1276

(2) INFORMATION FOR SEQ ID NO:25:

(i) SEQUENCE CHARACTERISTICS:
        (A) LENGTH: 59 amino acids
        (B) TYPE: Amino Acid
        (D) TOPOLOGY: Linear (xi) SEQUENCE DESCRIPTION: SEQ ID NO:25:

Ala Arg Asn Ile Leu Val Asn Ser Asn Leu Val Cys Lys Val Ser
 1               5                  10                  15

Asp Phe Gly Leu Ser Arg Phe Leu Glu Asp Asp Thr Ser Asp Pro
                20                  25                  30

Thr Tyr Thr Ser Ala Leu Gly Gly Lys Ile Pro Met Arg Trp Thr
                35                  40                  45

Ala Pro Glu Ala Ile Gln Tyr Arg Lys Phe Ala Ser Ala Ser
                50                  55              59

(2) INFORMATION FOR SEQ ID NO:26:

(i) SEQUENCE CHARACTERISTICS:
        (A) LENGTH: 54 amino acids
        (B) TYPE: Amino Acid
        (D) TOPOLOGY: Linear (xi) SEQUENCE DESCRIPTION: SEQ ID NO:26:

Asn Val Leu Val Lys Ser Pro Asn His Val Lys Ile Thr Asp Phe
1               5                   10                  15

Gly Leu Ala Arg Leu Leu Glu Gly Asp Glu Lys Glu Tyr Asn Ala
                20                  25                  30

Asp Gly Gly Lys Met Pro Ile Lys Trp Met Ala Leu Glu Cys Ile
                35                  40                  45

His Tyr Arg Lys Phe Thr His Gln Ser
                50              54

(2) INFORMATION FOR SEQ ID NO:27:

(i) SEQUENCE CHARACTERISTICS:
        (A) LENGTH: 54 amino acids
        (B) TYPE: Amino Acid
        (D) TOPOLOGY: Linear (xi) SEQUENCE DESCRIPTION: SEQ ID NO:27:

Asn Cys Met Leu Ala Gly Asp Met Thr Val Cys Val Ala Asp Phe
1               5                   10                  15

Gly Leu Ser Trp Lys Ile Tyr Ser Gly Ala Thr Ile Val Arg Gly
                20                  25                  30

Cys Ala Ser Lys Leu Pro Val Lys Trp Leu Ala Leu Gly Ser Leu
                35                  40                  45

Ala Asp Asn Leu Tyr Thr Val His Ser
                50              54

(2) INFORMATION FOR SEQ ID NO:28:

(i) SEQUENCE CHARACTERISTICS:
        (A) LENGTH: 27 amino acids
        (B) TYPE: Amino Acid
        (D) TOPOLOGY: Linear (xi) SEQUENCE DESCRIPTION: SEQ ID NO:28:

Asn Cys Leu Val Gly Lys Asn Tyr Thr Ile Lys Ile Ala Asp Phe
1               5                   10                  15

Gly Met Ser Arg Asn Leu Tyr Ser Gly Asp Tyr Tyr
                20                  25      27

(2) INFORMATION FOR SEQ ID NO:29:

(i) SEQUENCE CHARACTERISTICS:
        (A) LENGTH: 58 amino acids
        (B) TYPE: Amino Acid
        (D) TOPOLOGY: Linear (xi) SEQUENCE DESCRIPTION: SEQ ID NO:29:

Thr Arg Asn Ile Leu Val Glu Asn Glu Asn Arg Val Lys Ile Gly
1               5                   10                  15

Asp Phe Gly Leu Thr Lys Val Leu Pro Gln Asp Lys Glu Tyr Tyr
                20                  25                  30

Lys Val Lys Glu Pro Gly Glu Ser Pro Ile Phe Trp Tyr Ala Pro
                35                  40                  45

Glu Ser Leu Thr Glu Ser Leu Phe Ser Val Ala Ser Asp
                50                  55          58

(2) INFORMATION FOR SEQ ID NO:30:

(i) SEQUENCE CHARACTERISTICS:

(A) LENGTH: 58 amino acids
            (B) TYPE: Amino Acid
            (D) TOPOLOGY: Linear (xi) SEQUENCE DESCRIPTION: SEQ ID NO:30:

Ala Arg Asn Ile Leu Val Asn Ser Asn Leu Val Cys Lys Val Ser
 1               5                  10                  15

Asp Phe Gly Met Ser Arg Val Leu Glu Asp Asp Pro Glu Ala Ala
                20                  25                  30

Tyr Thr Thr Arg Gly Gly Lys Ile Pro Ile Arg Trp Thr Ala Pro
                35                  40                  45

Glu Ala Ile Ala Tyr Arg Lys Phe Thr Ser Ala Ser Asp
                50                  55      58

(2) INFORMATION FOR SEQ ID NO:31:

(i) SEQUENCE CHARACTERISTICS:
          (A) LENGTH: 4425 base pairs
          (B) TYPE: Nucleic Acid
          (C) STRANDEDNESS: Single
          (D) TOPOLOGY: Linear (xi) SEQUENCE DESCRIPTION: SEQ ID NO:31:

| | |
|---|---:|
| TCGGGTCGGA CCCACGCGCA GCGGCCGGAG ATGCAGCGGG GCGCCGCGCT | 50 |
| GTGCCTGCGA CTGTGGCTCT GCCTGGGACT CCTGGACGGC CTGGTGAGTG | 100 |
| GCTACTCCAT GACCCCCCCG ACCTTGAACA TCACGGAGGA GTCACACGTC | 150 |
| ATCGACACCG GTGACAGCCT GTCCATCTCC TGCAGGGGAC AGCACCCCCT | 200 |
| CGAGTGGGCT TGGCCAGGAG CTCAGGAGGC GCCAGCCACC GGAGACAAGG | 250 |
| ACAGCGAGGA CACGGGGGTG GTGCGAGACT GCGAGGGCAC AGACGCCAGG | 300 |
| CCCTACTGCA AGGTGTTGCT GCTGCACGAG GTACATGCCA ACGACACAGG | 350 |
| CAGCTACGTC TGCTACTACA AGTACATCAA GGCACGCATC GAGGGCACCA | 400 |
| CGGCCGCCAG CTCCTACGTG TTCGTGAGAG ACTTTGAGCA GCCATTCATC | 450 |
| AACAAGCCTG ACACGCTCTT GGTCAACAGG AAGGACGCCA TGTGGGTGCC | 500 |
| CTGTCTGGTG TCCATCCCCG GCCTCAATGT CACGCTGCGC TCGCAAAGCT | 550 |
| CGGTGCTGTG GCCAGACGGG CAGGAGGTGG TGTGGGATGA CCGGCGGGGC | 600 |
| ATGCTCGTGT CCACGCCACT GCTGCACGAT GCCCTGTACC TGCAGTGCGA | 650 |
| GACCACCTGG GGAGACCAGG ACTTCCTTTC CAACCCCTTC CTGGTGCACA | 700 |
| TCACAGGCAA CGAGCTCTAT GACATCCAGC TGTTGCCCAG GAAGTCGCTG | 750 |
| GAGCTGCTGG TAGGGGAGAA GCTGGTCCTG AACTGCACCG TGTGGGCTGA | 800 |
| GTTTAACTCA GGTGTCACCT TTGACTGGGA CTACCCAGGG AAGCAGGCAG | 850 |
| AGCGGGGTAA GTGGGTGCCC GAGCGACGCT CCCAGCAGAC CCACACAGAA | 900 |
| CTCTCCAGCA TCCTGACCAT CCACAACGTC AGCCAGCACG ACCTGGGCTC | 950 |
| GTATGTGTGC AAGGCCAACA ACGGCATCCA GCGATTTCGG GAGAGCACCG | 1000 |
| AGGTCATTGT GCATGAAAAT CCCTTCATCA GCGTCGAGTG GCTCAAAGGA | 1050 |
| CCCATCCTGG AGGCCACGGC AGGAGACGAG CTGGTGAAGC TGCCCGTGAA | 1100 |
| GCTGGCAGCG TACCCCCCGC CGAGTTCCA GTGGTACAAG GATGGAAAGG | 1150 |
| CACTGTCCGG GCGCCACAGT CCACATGCCC TGGTGCTCAA GGAGGTGACA | 1200 |
| GAGGCCAGCA CAGGCACCTA CACCCTCGCC CTGTGGAACT CCGCTGCTGG | 1250 |

```
CCTGAGGCGC AACATCAGCC TGGAGCTGGT GGTGAATGTG CCCCCCCAGA      1300

TACATGAGAA GGAGGCCTCC TCCCCCAGCA TCTACTCGCG TCACAGCCGC      1350

CAGGCCCTCA CCTGCACGGC CTACGGGGTG CCCCTGCCTC TCAGCATCCA      1400

GTGGCACTGG CGGCCCTGGA CACCCTGCAA GATGTTTGCC CAGCGTAGTC      1450

TCCGGCGGCG GCAGCAGCAA GACCTCATGC ACAGTGCCG TGACTGGAGG       1500

GCGGTGACCA CGCAGGATGC CGTGAACCCC ATCGAGAGCC TGGACACCTG      1550

GACCGAGTTT GTGGAGGGAA AGAATAAGAC TGTGAGCAAG CTGGTGATCC      1600

AGAATGCCAA CGTGTCTGCC ATGTACAAGT GTGTGGTCTC CAACAAGGTG      1650

GGCCAGGATG AGCGGCTCAT CTACTTCTAT GTGACCACCA TCCCCGACGG      1700

CTTCACCATC GAATCCAAGC CATCCGAGGA GCTACTAGAG GGCCAGCCGG      1750

TGCTCCTGAG CTGCCAAGCC GACAGCTACA AGTACGAGCA TCTGCGCTGG      1800

TACCGCCTCA ACCTGTCCAC GCTGCACGAT GCGCACGGGA ACCCGCTTCT      1850

GCTCGACTGC AAGAACGTGC ATCTGTTCGC CACCCCTCTG GCCGCCAGCC      1900

TGGAGGAGGT GGCACCTGGG GCGCGCCACG CCACGCTCAG CCTGAGTATC      1950

CCCCGCGTCG CGCCCGAGCA CGAGGGCCAC TATGTGTGCG AAGTGCAAGA      2000

CCGGCGCAGC CATGACAAGC ACTGCCACAA GAAGTACCTG TCGGTGCAGG      2050

CCCTGGAAGC CCCTCGGCTC ACGCAGAACT TGACCGACCT CCTGGTGAAC      2100

GTGAGCGACT CGCTGGAGAT GCAGTGCTTG GTGGCCGGAG CGCACGCGCC      2150

CAGCATCGTG TGGTACAAAG ACGAGAGGCT GCTGGAGGAA AAGTCTGGAG      2200

TCGACTTGGC GGACTCCAAC CAGAAGCTGA GCATCCAGCG CGTGCGCGAG      2250

GAGGATGCGG GACGCTATCT GTGCAGCGTG TGCAACGCCA AGGGCTGCGT      2300

CAACTCCTCC GCCAGCGTGG CCGTGGAAGG CTCCGAGGAT AAGGGCAGCA      2350

TGGAGATCGT GATCCTTGTC GGTACCGGCG TCATCGCTGT CTTCTTCTGG      2400

GTCCTCCTCC TCCTCATCTT CTGTAACATG AGGAGGCCGG CCCACGCAGA      2450

CATCAAGACG GGCTACCTGT CCATCATCAT GGACCCCGGG GAGGTGCCTC      2500

TGGAGGAGCA ATGCGAATAC CTGTCCTACG ATGCCAGCCA GTGGGAATTC      2550

CCCCGAGAGC GGCTGCACCT GGGGAGAGTG CTCGGCTACG GCGCCTTCGG      2600

GAAGGTGGTG GAAGCCTCCG CTTTCGGCAT CCACAAGGGC AGCAGCTGTG      2650

ACACCGTGGC CGTGAAAATG CTGAAAGAGG GCGCCACGGC CAGCGAGCAC      2700

CGCGCGCTGA TGTCGGAGCT CAAGATCCTC ATTCACATCG GCAACCACCT      2750

CAACGTGGTC AACCTCCTCG GGGCGTGCAC CAAGCCGCAG GGCCCCCTCA      2800

TGGTGATCGT GGAGTTCTGC AAGTACGGCA ACCTCTCCAA CTTCCTGCGC      2850

GCCAAGCGGG ACGCCTTCAG CCCCTGCGCG GAGAAGTCTC CCGAGCAGCG      2900

CGGACGCTTC CGCGCCATGG TGGAGCTCGC CAGGCTGGAT CGGAGGCGGC      2950

CGGGGAGCAG CGACAGGGTC CTCTTCGCGC GGTTCTCGAA GACCGAGGGC      3000

GGAGCGAGGC GGGCTTCTCC AGACCAAGAA GCTGAGGACC TGTGGCTGAG      3050

CCCGCTGACC ATGGAAGATC TTGTCTGCTA CAGCTTCCAG GTGGCCAGAG      3100

GGATGGAGTT CCTGGCTTCC CGAAAGTGCA TCCACAGAGA CCTGGCTGCT      3150

CGGAACATTC TGCTGTCGGA AAGCGACGTG GTGAAGATCT GTGACTTTGG      3200

CCTTGCCCGG GACATCTACA AAGACCCTGA CTACGTCCGC AAGGGCAGTG      3250
```

-continued

```
CCCGGCTGCC CCTGAAGTGG ATGGCCCCTG AAAGCATCTT CGACAAGGTG        3300

TACACCACGC AGAGTGACGT GTGGTCCTTT GGGGTGCTTC TCTGGGAGAT        3350

CTTCTCTCTG GGGGCCTCCC CGTACCCTGG GGTGCAGATC AATGAGGAGT        3400

TCTGCCAGCG GCTGAGAGAC GGCACAAGGA TGAGGGCCCC GGAGCTGGCC        3450

ACTCCCGCCA TACGCCGCAT CATGCTGAAC TGCTGGTCCG GAGACCCCAA        3500

GGCGAGACCT GCATTCTCGG AGCTGGTGGA GATCCTGGGG GACCTGCTCC        3550

AGGGCAGGGG CCTGCAAGAG AAGAGGAGG TCTGCATGGC CCCGCGCAGC         3600

TCTCAGAGCT CAGAAGAGGG CAGCTTCTCG CAGGTGTCCA CCATGGCCCT        3650

ACACATCGCC CAGGCTGACG CTGAGGACAG CCCGCCAAGC CTGCAGCGCC        3700

ACAGCCTGGC CGCCAGGTAT TACAACTGGG TGTCCTTTCC CGGGTGCCTG        3750

GCCAGAGGGG CTGAGACCCG TGGTTCCTCC AGGATGAAGA CATTTGAGGA        3800

ATTCCCCATG ACCCCAACGA CCTACAAAGG CTCTGTGGAC AACCAGACAG        3850

ACAGTGGGAT GGTGCTGGCC TCGGAGGAGT TTGAGCAGAT AGAGAGCAGG        3900

CATAGACAAG AAAGCGGCTT CAGGTAGCTG AAGCAGAGAG AGAGAAGGCA        3950

GCATACGTCA GCATTTTCTT CTCTGCACTT ATAAGAAAGA TCAAAGACTT        4000

TAAGACTTTC GCTATTTCTT CTGCTATCTA CTACAAACTT CAAAGAGGAA        4050

CCAGGAGGCC AAGAGGAGCA TGAAAGTGGA CAAGGAGTGT GACCACTGAA        4100

GCACCACAGG GAGGGGTTAG GCCTCCGGAT GACTGCGGGC AGGCCTGGAT        4150

AATATCCAGC CTCCCACAAG AAGCTGGTGG AGCAGAGTGT TCCCTGACTC        4200

CTCCAAGGAA AGGGAGACGC CCTTTCATGG TCTGCTGAGT AACAGGTGCC        4250

TTCCCAGACA CTGGCGTTAC TGCTTGACCA AAGAGCCCTC AAGCGGCCCT        4300

TATGCCAGCG TGACAGAGGG CTCACCTCTT GCCTTCTAGG TCACTTCTCA        4350

CAATGTCCCT TCAGCACCTG ACCCTGTGCC CGCCAGTTAT TCCTTGGTAA        4400

TATGAGTAAT ACATCAAAGA GTAGT                                  4425
```

(2) INFORMATION FOR SEQ ID NO:32:

(i) SEQUENCE CHARACTERISTICS:
        (A) LENGTH: 4425 base pairs
        (B) TYPE: Nucleic Acid
        (C) STRANDEDNESS: Single
        (D) TOPOLOGY: Linear (xi) SEQUENCE DESCRIPTION: SEQ ID NO:32:

```
AGCCCAGCCT GGGTGCGCGT CGCCGGCCTC TACGTCGCCC CGCGGCGCGA          50

CACGGACGCT GACACCGAGA CGGACCCTGA GGACCTGCCG GACCACTCAC         100

CGATGAGGTA CTGGGGGGGC TGGAACTTGT AGTGCCTCCT CAGTGTGCAG         150

TAGCTGTGGC CACTGTCGGA CAGGTAGAGG ACGTCCCCTG TCGTGGGGGA         200

GCTCACCCGA ACCGGTCCTC GAGTCCTCCG CGGTCGGTGG CCTCTGTTCC         250

TGTCGCTCCT GTGCCCCCAC CACGCTCTGA CGCTCCCGTG TCTGCGGTCC         300

GGGATGACGT TCCACAACGA CGACGTGCTC CATGTACGGT TGCTGTGTCC         350

GTCGATGCAG ACGATGATGT TCATGTAGTT CCGTGCGTAG CTCCCGTGGT         400

GCCGGCGGTC GAGGATGCAC AAGCACTCTC TGAAACTCGT CGGTAAGTAG         450

TTGTTCGGAC TGTGCGAGAA CCAGTTGTCC TTCCTGCGGT ACACCCACGG         500
```

```
GACAGACCAC AGGTAGGGGC CGGAGTTACA GTGCGACGCG AGCGTTTCGA         550

GCCACGACAC CGGTCTGCCC GTCCTCCACC ACACCCTACT GGCCGCCCCG         600

TACGAGCACA GGTGCGGTGA CGACGTGCTA CGGGACATGG ACGTCACGCT         650

CTGGTGGACC CCTCTGGTCC TGAAGGAAAG GTTGGGGAAG GACCACGTGT         700

AGTGTCCGTT GCTCGAGATA CTGTAGGTCG ACAACGGGTC CTTCAGCGAC         750

CTCGACGACC ATCCCCTCTT CGACCAGGAC TTGACGTGGC ACACCCGACT         800

CAAATTGAGT CCACAGTGGA AACTGACCCT GATGGGTCCC TTCGTCCGTC         850

TCGCCCCATT CACCCACGGG CTCGCTGCGA GGGTCGTCTG GGTGTGTCTT         900

GAGAGGTCGT AGGACTGGTA GGTGTTGCAG TCGGTCGTGC TGGACCCGAG         950

CATACACACG TTCCGGTTGT TGCCGTAGGT CGCTAAAGCC CTCTCGTGGC        1000

TCCAGTAACA CGTACTTTTA GGGAAGTAGT CGCAGCTCAC CGAGTTTCCT        1050

GGGTAGGACC TCCGGTGCCG TCCTCTGCTC GACCACTTCG ACGGGCACTT        1100

CGACCGTCGC ATGGGGGCG GGCTCAAGGT CACCATGTTC CTACCTTTCC         1150

GTGACAGGCC CGCGGTGTCA GGTGTACGGG ACCACGAGTT CCTCCACTGT        1200

CTCCGGTCGT GTCCGTGGAT GTGGGAGCGG ACACCTTGA GGCGACGACC         1250

GGACTCCGCG TTGTAGTCGG ACCTCGACCA CCACTTACAC GGGGGGGTCT        1300

ATGTACTCTT CCTCCGGAGG AGGGGTCGT AGATGAGCGC AGTGTCGGCG         1350

GTCCGGGAGT GGACGTGCCG GATGCCCCAC GGGGACGGAG AGTCGTAGGT        1400

CACCGTGACC GCCGGGACCT GTGGGACGTT CTACAAACGG GTCGCATCAG        1450

AGGCCGCCGC CGTCGTCGTT CTGGAGTACG GTGTCACGGC ACTGACCTCC        1500

CGCCACTGGT GCGTCCTACG GCACTTGGGG TAGCTCTCGG ACCTGTGGAC        1550

CTGGCTCAAA CACCTCCCTT TCTTATTCTG ACACTCGTTC GACCACTAGG        1600

TCTTACGGTT GCACAGACGG TACATGTTCA CACACCAGAG GTTGTTCCAC        1650

CCGGTCCTAC TCGCCGAGTA GATGAAGATA CACTGGTGGT AGGGGCTGCC        1700

GAAGTGGTAG CTTAGGTTCG GTAGGCTCCT CGATGATCTC CCGGTCGGCC        1750

ACGAGGACTC GACGGTTCGG CTGTCGATGT TCATGCTCGT AGACGCGACC        1800

ATGGCGGAGT TGGACAGGTG CGACGTGCTA CGCGTGCCCT TGGGCGAAGA        1850

CGAGCTGACG TTCTTGCACG TAGACAAGCG GTGGGAGAC CGGCGGTCGG         1900

ACCTCCTCCA CCGTGGACCC CGCGCGGTGC GGTGCGAGTC GGACTCATAG        1950

GGGGCGCAGC GCGGGCTCGT GCTCCCGGTG ATACACACGC TTCACGTTCT        2000

GGCCGCGTCG GTACTGTTCG TGACGGTGTT CTTCATGGAC AGCCACGTCC        2050

GGGACCTTCG GGGAGCCGAG TGCGTCTTGA ACTGGCTGGA GGACCACTTG        2100

CACTCGCTGA GCGACCTCTA CGTCACGAAC CACCGGCCTC GCGTGCGCGG        2150

GTCGTAGCAC ACCATGTTTC TGCTCTCCGA CGACCTCCTT TTCAGACCTC        2200

AGCTGAACCG CCTGAGGTTG GTCTTCGACT CGTAGGTCGC GCACGCGCTC        2250

CTCCTACGCC CTGCGATAGA CACGTCGCAC ACGTTGCGGT TCCCGACGCA        2300

GTTGAGGAGG CGGTCGCACC GGCACCTTCC GAGGCTCCTA TTCCCGTCGT        2350

ACCTCTAGCA CTAGGAACAG CCATGGCCGC AGTAGCGACA GAAGAAGACC        2400

CAGGAGGAGG AGGAGTAGAA GACATTGTAC TCCTCCGGCC GGGTGCGTCT        2450
```

-continued

| | |
|---|---|
| GTAGTTCTGC CCGATGGACA GGTAGTAGTA CCTGGGGCCC CTCCACGGAG | 2500 |
| ACCTCCTCGT TACGCTTATG GACAGGATGC TACGGTCGGT CACCCTTAAG | 2550 |
| GGGGCTCTCG CCGACGTGGA CCCCTCTCAC GAGCCGATGC CGCGGAAGCC | 2600 |
| CTTCCACCAC CTTCGGAGGC GAAAGCCGTA GGTGTTCCCG TCGTCGACAC | 2650 |
| TGTGGCACCG GCACTTTTAC GACTTTCTCC CGCGGTGCCG GTCGCTCGTG | 2700 |
| GCGCGCGACT ACAGCCTCGA GTTCTAGGAG TAAGTGTAGC CGTTGGTGGA | 2750 |
| GTTGCACCAG TTGGAGGAGC CCCGCACGTG GTTCGGCGTC CCGGGGGAGT | 2800 |
| ACCACTAGCA CCTCAAGACG TTCATGCCGT TGGAGAGGTT GAAGGACGCG | 2850 |
| CGGTTCGCCC TGCGGAAGTC GGGGACGCGC CTCTTCAGAG GGCTCGTCGC | 2900 |
| GCCTGCGAAG GCGCGGTACC ACCTCGAGCG GTCCGACCTA GCCTCCGCCG | 2950 |
| GCCCCTCGTC GCTGTCCCAG GAGAAGCGCG CCAAGAGCTT CTGGCTCCCG | 3000 |
| CCTCGCTCCG CCCGAAGAGG TCTGGTTCTT CGACTCCTGG ACACCGACTC | 3050 |
| GGGCGACTGG TACCTTCTAG AACAGACGAT GTCGAAGGTC CACCGGTCTC | 3100 |
| CCTACCTCAA GGACCGAAGG GCTTTCACGT AGGTGTCTCT GGACCGACGA | 3150 |
| GCCTTGTAAG ACGACAGCCT TTCGCTGCAC CACTTCTAGA CACTGAAACC | 3200 |
| GGAACGGGCC CTGTAGATGT TTCTGGGACT GATGCAGGCG TTCCCGTCAC | 3250 |
| GGGCCGACGG GGACTTCACC TACCGGGGAC TTTCGTAGAA GCTGTTCCAC | 3300 |
| ATGTGGTGCG TCTCACTGCA CACCAGGAAA CCCCACGAAG AGACCCTCTA | 3350 |
| GAAGAGAGAC CCCCGGAGGG GCATGGGACC CCACGTCTAG TTACTCCTCA | 3400 |
| AGACGGTCGC CGACTCTCTG CCGTGTTCCT ACTCCCGGGG CCTCGACCGG | 3450 |
| TGAGGGCGGT ATGCGGCGTA GTACGACTTG ACGACCAGGC CTCTGGGGTT | 3500 |
| CCGCTCTGGA CGTAAGAGCC TCGACCACCT CTAGGACCCC CTGGACGAGG | 3550 |
| TCCCGTCCCC GGACGTTCTC CTTCTCCTCC AGACGTACCG GGGCGCGTCG | 3600 |
| AGAGTCTCGA GTCTTCTCCC GTCGAAGAGC GTCCACAGGT GGTACCGGGA | 3650 |
| TGTGTAGCGG GTCCGACTGC GACTCCTGTC GGGCGGTTCG GACGTCGCGG | 3700 |
| TGTCGGACCG GCGGTCCATA ATGTTGACCC ACAGGAAAGG GCCCACGGAC | 3750 |
| CGGTCTCCCC GACTCTGGGC ACCAAGGAGG TCCTACTTCT GTAAACTCCT | 3800 |
| TAAGGGGTAC TGGGGTTGCT GGATGTTTCC GAGACACCTG TTGGTCTGTC | 3850 |
| TGTCACCCTA CCACGACCGG AGCCTCCTCA AACTCGTCTA TCTCTCGTCC | 3900 |
| GTATCTGTTC TTTCGCCGAA GTCCATCGAC TTCGTCTCTC TCTCTTCCGT | 3950 |
| CGTATGCAGT CGTAAAAGAA GAGACGTGAA TATTCTTTCT AGTTTCTGAA | 4000 |
| ATTCTGAAAG CGATAAAGAA GACGATAGAT GATGTTTGAA GTTTCTCCTT | 4050 |
| GGTCCTCCGG TTCTCCTCGT ACTTTCACCT GTTCCTCACA CTGGTGACTT | 4100 |
| CGTGGTGTCC CTCCCCAATC CGGAGGCCTA CTGACGCCCG TCCGGACCTA | 4150 |
| TTATAGGTCG GAGGGTGTTC TTCGACCACC TCGTCTCACA AGGGACTGAG | 4200 |
| GAGGTTCCTT TCCCTCTGCG GGAAAGTACC AGACGACTCA TTGTCCACGG | 4250 |
| AAGGGTCTGT GACCGCAATG ACGAACTGGT TTCTCGGGAG TTCGCCGGGA | 4300 |
| ATACGGTCGC ACTGTCTCCC GAGTGGAGAA CGGAAGATCC AGTGAAGAGT | 4350 |
| GTTACAGGGA AGTCGTGGAC TGGGACACGG GCGGTCAATA AGGAACCATT | 4400 |
| ATACTCATTA TGTAGTTTCT CATCA | 4425 |

(2) INFORMATION FOR SEQ ID NO:33:

(i) SEQUENCE CHARACTERISTICS:
        (A) LENGTH: 1298 amino acids
        (B) TYPE: Amino Acid
        (D) TOPOLOGY: Linear (xi) SEQUENCE DESCRIPTION: SEQ ID NO:33:

```
Met Gln Arg Gly Ala Ala Leu Cys Leu Arg Leu Trp Leu Cys Leu
 1               5                  10                  15

Gly Leu Leu Asp Gly Leu Val Ser Gly Tyr Ser Met Thr Pro Pro
                20                  25                  30

Thr Leu Asn Ile Thr Glu Glu Ser His Val Ile Asp Thr Gly Asp
                35                  40                  45

Ser Leu Ser Ile Ser Cys Arg Gly Gln His Pro Leu Glu Trp Ala
                50                  55                  60

Trp Pro Gly Ala Gln Glu Ala Pro Ala Thr Gly Asp Lys Asp Ser
                65                  70                  75

Glu Asp Thr Gly Val Val Arg Asp Cys Glu Gly Thr Asp Ala Arg
                80                  85                  90

Pro Tyr Cys Lys Val Leu Leu Leu His Glu Val His Ala Asn Asp
                95                 100                 105

Thr Gly Ser Tyr Val Cys Tyr Tyr Lys Tyr Ile Lys Ala Arg Ile
               110                 115                 120

Glu Gly Thr Thr Ala Ala Ser Ser Tyr Val Phe Val Arg Asp Phe
               125                 130                 135

Glu Gln Pro Phe Ile Asn Lys Pro Asp Thr Leu Leu Val Asn Arg
               140                 145                 150

Lys Asp Ala Met Trp Val Pro Cys Leu Val Ser Ile Pro Gly Leu
               155                 160                 165

Asn Val Thr Leu Arg Ser Gln Ser Ser Val Leu Trp Pro Asp Gly
               170                 175                 180

Gln Glu Val Val Trp Asp Asp Arg Arg Gly Met Leu Val Ser Thr
               185                 190                 195

Pro Leu Leu His Asp Ala Leu Tyr Leu Gln Cys Glu Thr Thr Trp
               200                 205                 210

Gly Asp Gln Asp Phe Leu Ser Asn Pro Phe Leu Val His Ile Thr
               215                 220                 225

Gly Asn Glu Leu Tyr Asp Ile Gln Leu Leu Pro Arg Lys Ser Leu
               230                 235                 240

Glu Leu Leu Val Gly Glu Lys Leu Val Leu Asn Cys Thr Val Trp
               245                 250                 255

Ala Glu Phe Asn Ser Gly Val Thr Phe Asp Trp Asp Tyr Pro Gly
               260                 265                 270

Lys Gln Ala Glu Arg Gly Lys Trp Val Pro Glu Arg Arg Ser Gln
               275                 280                 285

Gln Thr His Thr Glu Leu Ser Ser Ile Leu Thr Ile His Asn Val
               290                 295                 300

Ser Gln His Asp Leu Gly Ser Tyr Val Cys Lys Ala Asn Asn Gly
               305                 310                 315

Ile Gln Arg Phe Arg Glu Ser Thr Glu Val Ile Val His Glu Asn
               320                 325                 330

Pro Phe Ile Ser Val Glu Trp Leu Lys Gly Pro Ile Leu Glu Ala
               335                 340                 345
```

-continued

```
Thr Ala Gly Asp Glu Leu Val Lys Leu Pro Val Lys Leu Ala Ala
                350                 355                 360
Tyr Pro Pro Pro Glu Phe Gln Trp Tyr Lys Asp Gly Lys Ala Leu
                365                 370                 375
Ser Gly Arg His Ser Pro His Ala Leu Val Leu Lys Glu Val Thr
                380                 385                 390
Glu Ala Ser Thr Gly Thr Tyr Thr Leu Ala Leu Trp Asn Ser Ala
                395                 400                 405
Ala Gly Leu Arg Arg Asn Ile Ser Leu Glu Leu Val Val Asn Val
                410                 415                 420
Pro Pro Gln Ile His Glu Lys Glu Ala Ser Ser Pro Ser Ile Tyr
                425                 430                 435
Ser Arg His Ser Arg Gln Ala Leu Thr Cys Thr Ala Tyr Gly Val
                440                 445                 450
Pro Leu Pro Leu Ser Ile Gln Trp His Trp Arg Pro Trp Thr Pro
                455                 460                 465
Cys Lys Met Phe Ala Gln Arg Ser Leu Arg Arg Arg Gln Gln Gln
                470                 475                 480
Asp Leu Met Pro Gln Cys Arg Asp Trp Arg Ala Val Thr Thr Gln
                485                 490                 495
Asp Ala Val Asn Pro Ile Glu Ser Leu Asp Thr Trp Thr Glu Phe
                500                 505                 510
Val Glu Gly Lys Asn Lys Thr Val Ser Lys Leu Val Ile Gln Asn
                515                 520                 525
Ala Asn Val Ser Ala Met Tyr Lys Cys Val Val Ser Asn Lys Val
                530                 535                 540
Gly Gln Asp Glu Arg Leu Ile Tyr Phe Tyr Val Thr Thr Ile Pro
                545                 550                 555
Asp Gly Phe Thr Ile Glu Ser Lys Pro Ser Glu Glu Leu Leu Glu
                560                 565                 570
Gly Gln Pro Val Leu Leu Ser Cys Gln Ala Asp Ser Tyr Lys Tyr
                575                 580                 585
Glu His Leu Arg Trp Tyr Arg Leu Asn Leu Ser Thr Leu His Asp
                590                 595                 600
Ala His Gly Asn Pro Leu Leu Leu Asp Cys Lys Asn Val His Leu
                605                 610                 615
Phe Ala Thr Pro Leu Ala Ala Ser Leu Glu Glu Val Ala Pro Gly
                620                 625                 630
Ala Arg His Ala Thr Leu Ser Leu Ser Ile Pro Arg Val Ala Pro
                635                 640                 645
Glu His Glu Gly His Tyr Val Cys Glu Val Gln Asp Arg Arg Ser
                650                 655                 660
His Asp Lys His Cys His Lys Lys Tyr Leu Ser Val Gln Ala Leu
                665                 670                 675
Glu Ala Pro Arg Leu Thr Gln Asn Leu Thr Asp Leu Leu Val Asn
                680                 685                 690
Val Ser Asp Ser Leu Glu Met Gln Cys Leu Val Ala Gly Ala His
                695                 700                 705
Ala Pro Ser Ile Val Trp Tyr Lys Asp Glu Arg Leu Leu Glu Glu
                710                 715                 720
Lys Ser Gly Val Asp Leu Ala Asp Ser Asn Gln Lys Leu Ser Ile
                725                 730                 735
```

-continued

```
Gln Arg Val Arg Glu Glu Asp Ala Gly Arg Tyr Leu Cys Ser Val
            740                 745                 750
Cys Asn Ala Lys Gly Cys Val Asn Ser Ser Ala Ser Val Ala Val
            755                 760                 765
Glu Gly Ser Glu Asp Lys Gly Ser Met Glu Ile Val Ile Leu Val
            770                 775                 780
Gly Thr Gly Val Ile Ala Val Phe Phe Trp Val Leu Leu Leu Leu
            785                 790                 795
Ile Phe Cys Asn Met Arg Arg Pro Ala His Ala Asp Ile Lys Thr
            800                 805                 810
Gly Tyr Leu Ser Ile Ile Met Asp Pro Gly Glu Val Pro Leu Glu
            815                 820                 825
Glu Gln Cys Glu Tyr Leu Ser Tyr Asp Ala Ser Gln Trp Glu Phe
            830                 835                 840
Pro Arg Glu Arg Leu His Leu Gly Arg Val Leu Gly Tyr Gly Ala
            845                 850                 855
Phe Gly Lys Val Val Glu Ala Ser Ala Phe Gly Ile His Lys Gly
            860                 865                 870
Ser Ser Cys Asp Thr Val Ala Val Lys Met Leu Lys Glu Gly Ala
            875                 880                 885
Thr Ala Ser Glu His Arg Ala Leu Met Ser Glu Leu Lys Ile Leu
            890                 895                 900
Ile His Ile Gly Asn His Leu Asn Val Val Asn Leu Leu Gly Ala
            905                 910                 915
Cys Thr Lys Pro Gln Gly Pro Leu Met Val Ile Val Glu Phe Cys
            920                 925                 930
Lys Tyr Gly Asn Leu Ser Asn Phe Leu Arg Ala Lys Arg Asp Ala
            935                 940                 945
Phe Ser Pro Cys Ala Glu Lys Ser Pro Glu Gln Arg Gly Arg Phe
            950                 955                 960
Arg Ala Met Val Glu Leu Ala Arg Leu Asp Arg Arg Arg Pro Gly
            965                 970                 975
Ser Ser Asp Arg Val Leu Phe Ala Arg Phe Ser Lys Thr Glu Gly
            980                 985                 990
Gly Ala Arg Arg Ala Ser Pro Asp Gln Glu Ala Glu Asp Leu Trp
            995                 1000                1005
Leu Ser Pro Leu Thr Met Glu Asp Leu Val Cys Tyr Ser Phe Gln
            1010                1015                1020
Val Ala Arg Gly Met Glu Phe Leu Ala Ser Arg Lys Cys Ile His
            1025                1030                1035
Arg Asp Leu Ala Ala Arg Asn Ile Leu Leu Ser Glu Ser Asp Val
            1040                1045                1050
Val Lys Ile Cys Asp Phe Gly Leu Ala Arg Asp Ile Tyr Lys Asp
            1055                1060                1065
Pro Asp Tyr Val Arg Lys Gly Ser Ala Arg Leu Pro Leu Lys Trp
            1070                1075                1080
Met Ala Pro Glu Ser Ile Phe Asp Lys Val Tyr Thr Thr Gln Ser
            1085                1090                1095
Asp Val Trp Ser Phe Gly Val Leu Leu Trp Glu Ile Phe Ser Leu
            1100                1105                1110
Gly Ala Ser Pro Tyr Pro Gly Val Gln Ile Asn Glu Glu Phe Cys
            1115                1120                1125
Gln Arg Leu Arg Asp Gly Thr Arg Met Arg Ala Pro Glu Leu Ala
```

-continued

```
                    1130               1135               1140
Thr Pro Ala Ile Arg Arg Ile Met Leu Asn Cys Trp Ser Gly Asp
                    1145               1150               1155
Pro Lys Ala Arg Pro Ala Phe Ser Glu Leu Val Glu Ile Leu Gly
                    1160               1165               1170
Asp Leu Leu Gln Gly Arg Gly Leu Gln Glu Glu Glu Val Cys
                    1175               1180               1185
Met Ala Pro Arg Ser Ser Gln Ser Ser Glu Glu Gly Ser Phe Ser
                    1190               1195               1200
Gln Val Ser Thr Met Ala Leu His Ile Ala Gln Ala Asp Ala Glu
                    1205               1210               1215
Asp Ser Pro Pro Ser Leu Gln Arg His Ser Leu Ala Ala Arg Tyr
                    1220               1225               1230
Tyr Asn Trp Val Ser Phe Pro Gly Cys Leu Ala Arg Gly Ala Glu
                    1235               1240               1245
Thr Arg Gly Ser Ser Arg Met Lys Thr Phe Glu Glu Phe Pro Met
                    1250               1255               1260
Thr Pro Thr Thr Tyr Lys Gly Ser Val Asp Asn Gln Thr Asp Ser
                    1265               1270               1275
Gly Met Val Leu Ala Ser Glu Glu Phe Glu Gln Ile Glu Ser Arg
                    1280               1285               1290
His Arg Gln Glu Ser Gly Phe Arg
                    1295        1298
```

(2) INFORMATION FOR SEQ ID NO:34:

(i) SEQUENCE CHARACTERISTICS:
        (A) LENGTH: 3348 base pairs
        (B) TYPE: Nucleic Acid
        (C) STRANDEDNESS: Single
        (D) TOPOLOGY: Linear (xi) SEQUENCE DESCRIPTION: SEQ ID NO:34:

```
ATGGCTGGGA TTTTCTATTT CGCCCTATTT TCGTGTCTCT TCGGGATTTG            50

CGACGCTGTC ACAGGTTCCA GGGTATACCC CGCGAATGAA GTTACCTTAT           100

TGGATTCCAG ATCTGTTCAG GGAGAACTTG GGTGGATAGC AAGCCCTCTG           150

GAAGGAGGGT GGGAGGAAGT GAGTATCATG GATGAAAAAA ATACACCAAT           200

CCGAACCTAC CAAGTGTGCA ATGTGATGGA ACCCAGCCAG AATAACTGGC           250

TACGAACTGA TTGGATCACC CGAGAAGGGG CTCAGAGGGT GTATATTGAG           300

ATTAAATTCA CCTTGAGGGA CTGCAATAGT CTTCCGGGCG TCATGGGGAC           350

TTGCAAGGAG ACGTTTAACC TGTACTACTA TGAATCAGAC AACGACAAAG           400

AGCGTTTCAT CAGAGAGAAC CAGTTTGTCA AAATTGACAC CATTGCTGCT           450

GATGAGAGCT TCACCCAAGT GGACATTGGT GACAGAATCA TGAAGCTGAA           500

CACCGAGATC CGGGATGTAG GCCATTAAG CAAAAAGGGG TTTTACCTGG            550

CTTTTCAGGA TGTGGGGGCC TGCATCGCCC TGGTATCAGT CCGTGTGTTC           600

TATAAAAAGT GTCCACTCAC AGTCCGCAAT CTGGCCCAGT TTCCTGACAC           650

CATCACAGGG GCTGATACGT CTTCCCTGGT GGAAGTTCGA GGCTCCTGTG           700

TCAACAACTC AGAAGAGAAA GATGTGCCAA AAATGTACTG TGGGGCAGAT           750

GGTGAATGGC TGGTACCCAT TGGCAACTGC CTATGCAACG CTGGGCATGA           800

GGAGCGGAGC GGAGAATGCC AAGCTTGCAA AATTGGATAT TACAAGGCTC           850
```

-continued

```
TCTCCACGGA TGCCACCTGT GCCAAGTGCC CACCCCACAG CTACTCTGTC       900

TGGGAAGGAG CCACCTCGTG CACCTGTGAC CGAGGCTTTT TCAGAGCTGA       950

CAACGATGCT GCCTCTATGC CCTGCACCCG TCCACCATCT GCTCCCCTGA      1000

ACTTGATTTC AAATGTCAAC GAGACATCTG TGAACTTGGA ATGGAGTAGC      1050

CCTCAGAATA CAGGTGGCCG CCAGGACATT TCCTATAATG TGGTATGCAA      1100

GAAATGTGGA GCTGGTGACC CCAGCAAGTG CCGACCCTGT GGAAGTGGGG      1150

TCCACTACAC CCCACAGCAG AATGGCTTGA AGACCACCAA AGGCTCCATC      1200

ACTGACCTCC TAGCTCATAC CAATTACACC TTTGAAATCT GGGCTGTGAA      1250

TGGAGTGTCC AAATATAACC CTAACCCAGA CCAATCAGTT TCTGTCACTG      1300

TGACCACCAA CCAAGCAGCA CCATCATCCA TTGCTTTGGT CCAGGCTAAA      1350

GAAGTCACAA GATACAGTGT GGCACTGGCT TGGCTGGAAC CAGATCGGCC      1400

CAATGGGGTA ATCCTGGAAT ATGAAGTCAA GTATTATGAG AAGGATCAGA      1450

ATGAGCGAAG CTATCGTATA GTTCGGACAG CTGCCAGGAA CACAGATATC      1500

AAAGGCCTGA ACCCTCTCAC TTCCTATGTT TTCCACGTGC GAGCCAGGAC      1550

AGCAGCTGGC TATGGAGACT TCAGTGAGCC CTTGGAGGTT ACAACCAACA      1600

CAGTGCCTTC CCGGATCATT GGAGATGGGG CTAACTCCAC AGTCCTTCTG      1650

GTCTCTGTCT CGGGCAGTGT GGTGCTGGTG GTAATTCTCA TTGCAGCTTT      1700

TGTCATCAGC CGGAGACGGA GTAAATACAG TAAAGCCAAA CAAGAAGCGG      1750

ATGAAGAGAA ACATTTGAAT CAAGGTGTAA GAACATATGT GGACCCCTTT      1800

ACGTACGAAG ATCCCAACCA AGCAGTGCGA GAGTTTGCCA AGAAAATTGA      1850

CGCATCCTGC ATTAAGATTG AAAAAGTTAT AGGAGTTGGT GAATTTGGTG      1900

AGGTATGCAG TGGGCGTCTC AAAGTGCCTG GCAAGAGAGA GATCTGTGTG      1950

GCTATCAAGA CTCTGAAAGC TGGTTATACA GACAAACAGA GGAGAGACTT      2000

CCTGAGTGAG GCCAGCATCA TGGGACAGTT TGACCATCCG AACATCATTC      2050

ACTTGGAAGG CGTGGTCACT AAATGTAAAC CAGTAATGAT CATAACAGAG      2100

TACATGGAGA ATGGCTCCTT GGATGCATTC CTCAGGAAAA ATGATGGCAG      2150

ATTTACAGTC ATTCAGCTGG TGGGCATGCT TCGTGGCATT GGGTCTGGGA      2200

TGAAGTATTT ATCTGATATG AGCTATGTGC ATCGTGATCT GGCCGCACGG      2250

AACATCCTGG TGAACAGCAA CTTGGTCTGC AAAGTGTCTG ATTTTGGCAT      2300

GTCCCGAGTG CTTGAGGATG ATCCGGAAGC AGCTTACACC ACCAGGGGTG      2350

GCAAGATTCC TATCCGGTGG ACTGCGCCAG AAGCAATTGC CTATCGTAAA      2400

TTCACATCAG CAAGTGATGT ATGGAGCTAT GGAATCGTTA TGTGGGAAGT      2450

GATGTCGTAC GGGGAGAGGC CCTATTGGGA TATGTCCAAT CAAGATGTGA      2500

TTAAAGCCAT TGAGGAAGGC TATCGGTTAC CCCCTCCAAT GGACTGCCCC      2550

ATTGCGCTCC ACCAGCTGAT GCTAGACTGC TGGCAGAAGG AGAGGAGCGA      2600

CAGGCCTAAA TTTGGGCAGA TTGTCAACAT GTTGGACAAA CTCATCCGCA      2650

ACCCCAACAG CTTGAAGAGG ACAGGGACGG AGAGCTCCAG ACCTAACACT      2700

GCCTTGTTGG ATCCAAGCTC CCCTGAATTC TCTGCTGTGG TATCAGTGGG      2750

CGATTGGCTC CAGGCCATTA AAATGGACCG GTATAAGGAT AACTTCACAG      2800
```

| | |
|---|---|
| CTGCTGGTTA TACCACACTA GAGGCTGTGG TGCACGTGAA CCAGGAGGAC | 2850 |
| CTGGCAAGAA TTGGTATCAC AGCCATCACA CACCAGAATA AGATTTTGAG | 2900 |
| CAGTGTCCAG GCAATGCGAA CCCAAATGCA GCAGATGCAC GGCAGAATGG | 2950 |
| TTCCCGTCTG AGCCAGTACT GAATAAACTC AAAACTCTTG AAATTAGTTT | 3000 |
| ACCTCATCCA TGCACTTTAA TTGAAGAACT GCACTTTTTT TACTTCGTCT | 3050 |
| TCGCCCTCTG AAATTAAAGA AATGAAAAAA AAAAACAAT ATCTGCAGCG | 3100 |
| TTGCTTGGTG CACAGATTGC TGAAACTGTG GGGCTTACAG AAATGACTGC | 3150 |
| CGGTCATTTG AATGAGACCT GGAACAAATC GTTTCTCAGA AGTACTTTTC | 3200 |
| TGTTCATCAC CAGTCTGTAA AATACATGTA CCTATAGAAA TAGAACACTG | 3250 |
| CCTCTGAGTT TTGATGCTGT ATTTGCTGCC AGACACTGAG CTTCTGAGAC | 3300 |
| ATCCCTGATT CTCTCTCCAT TTGGAATTAC AACGGTCGAC GAGCTCGA | 3348 |

(2) INFORMATION FOR SEQ ID NO:35:

(i) SEQUENCE CHARACTERISTICS:
        (A) LENGTH: 3348 base pairs
        (B) TYPE: Nucleic Acid
        (C) STRANDEDNESS: Single
        (D) TOPOLOGY: Linear (xi) SEQUENCE DESCRIPTION: SEQ ID NO:35:

| | |
|---|---|
| TACCGACCCT AAAAGATAAA GCGGGATAAA AGCACAGAGA AGCCCTAAAC | 50 |
| GCTGCGACAG TGTCCAAGGT CCCATATGGG GCGCTTACTT CAATGGAATA | 100 |
| ACCTAAGGTC TAGACAAGTC CCTCTTGAAC CCACCTATCG TTCGGGAGAC | 150 |
| CTTCCTCCCA CCCTCCTTCA CTCATAGTAC CTACTTTTTT TATGTGGTTA | 200 |
| GGCTTGGATG GTTCACACGT TACACTACCT TGGGTCGGTC TTATTGACCG | 250 |
| ATGCTTGACT AACCTAGTGG GCTCTTCCCC GAGTCTCCCA CATATAACTC | 300 |
| TAATTTAAGT GGAACTCCCT GACGTTATCA GAAGGCCCGC AGTACCCCTG | 350 |
| AACGTTCCTC TGCAAATTGG ACATGATGAT ACTTAGTCTG TTGCTGTTTC | 400 |
| TCGCAAAGTA GTCTCTCTTG GTCAAACAGT TTTAACTGTG GTAACGACGA | 450 |
| CTACTCTCGA AGTGGGTTCA CCTGTAACCA CTGTCTTAGT ACTTCGACTT | 500 |
| GTGGCTCTAG GCCCTACATC CCGGTAATTC GTTTTTCCCC AAAATGGACC | 550 |
| GAAAAGTCCT ACACCCCCGG ACGTAGCGGG ACCATAGTCA GGCACACAAG | 600 |
| ATATTTTTCA CAGGTGAGTG TCAGGCGTTA GACCGGGTCA AAGGACTGTG | 650 |
| GTAGTGTCCC CGACTATGCA GAAGGGACCA CCTTCAAGCT CCGAGGACAC | 700 |
| AGTTGTTGAG TCTTCTCTTT CTACACGGTT TTTACATGAC ACCCCGTCTA | 750 |
| CCACTTACCG ACCATGGGTA ACCGTTGACG GATACGTTGC GACCCGTACT | 800 |
| CCTCGCCTCG CCTCTTACGG TTCGAACGTT TTAACCTATA ATGTTCCGAG | 850 |
| AGAGGTGCCT ACGGTGGACA CGGTTCACGG GTGGGGTGTC GATGAGACAG | 900 |
| ACCCTTCCTC GGTGGAGCAC GTGGACACTG GCTCCGAAAA AGTCTCGACT | 950 |
| GTTGCTACGA CGGAGATACG GGACGTGGGC AGGTGGTAGA CGAGGGGACT | 1000 |
| TGAACTAAAG TTTACAGTTG CTCTGTAGAC ACTTGAACCT TACCTCATCG | 1050 |
| GGAGTCTTAT GTCCACCGGC GGTCCTGTAA AGGATATTAC ACCATACGTT | 1100 |
| CTTTACACCT CGACCACTGG GGTCGTTCAC GGCTGGGACA CCTTCACCCC | 1150 |

-continued

| | |
|---|---|
| AGGTGATGTG GGGTGTCGTC TTACCGAACT TCTGGTGGTT TCCGAGGTAG | 1200 |
| TGACTGGAGG ATCGAGTATG GTTAATGTGG AAACTTTAGA CCCGACACTT | 1250 |
| ACCTCACAGG TTTATATTGG GATTGGGTCT GGTTAGTCAA AGACAGTGAC | 1300 |
| ACTGGTGGTT GGTTCGTCGT GGTAGTAGGT AACGAAACCA GGTCCGATTT | 1350 |
| CTTCAGTGTT CTATGTCACA CCGTGACCGA ACCGACCTTG GTCTAGCCGG | 1400 |
| GTTACCCCAT TAGGACCTTA TACTTCAGTT CATAATACTC TTCCTAGTCT | 1450 |
| TACTCGCTTC GATAGCATAT CAAGCCTGTC GACGGTCCTT GTGTCTATAG | 1500 |
| TTTCCGGACT TGGGAGAGTG AAGGATACAA AAGGTGCACG CTCGGTCCTG | 1550 |
| TCGTCGACCG ATACCTCTGA AGTCACTCGG GAACCTCCAA TGTTGGTTGT | 1600 |
| GTCACGGAAG GGCCTAGTAA CCTCTACCCC GATTGAGGTG TCAGGAAGAC | 1650 |
| CAGAGACAGA GCCCGTCACA CCACGACCAC CATTAAGAGT AACGTCGAAA | 1700 |
| ACAGTAGTCG GCCTCTGCCT CATTTATGTC ATTTCGGTTT GTTCTTCGCC | 1750 |
| TACTTCTCTT TGTAAACTTA GTTCCACATT CTTGTATACA CCTGGGGAAA | 1800 |
| TGCATGCTTC TAGGGTTGGT TCGTCACGCT CTCAAACGGT TTCTTTAACT | 1850 |
| GCGTAGGACG TAATTCTAAC TTTTTCAATA TCCTCAACCA CTTAAACCAC | 1900 |
| TCCATACGTC ACCCGCAGAG TTTCACGGAC CGTTCTCTCT CTAGACACAC | 1950 |
| CGATAGTTCT GAGACTTTCG ACCAATATGT CTGTTTGTCT CCTCTCTGAA | 2000 |
| GGACTCACTC CGGTCGTAGT ACCCTGTCAA ACTGGTAGGC TTGTAGTAAG | 2050 |
| TGAACCTTCC GCACCAGTGA TTTACATTTG GTCATTACTA GTATTGTCTC | 2100 |
| ATGTACCTCT TACCGAGGAA CCTACGTAAG GAGTCCTTTT TACTACCGTC | 2150 |
| TAAATGTCAG TAAGTCGACC ACCCGTACGA AGCACCGTAA CCCAGACCCT | 2200 |
| ACTTCATAAA TAGACTATAC TCGATACACG TAGCACTAGA CCGGCGTGCC | 2250 |
| TTGTAGGACC ACTTGTCGTT GAACCAGACG TTTCACAGAC TAAAACCGTA | 2300 |
| CAGGGCTCAC GAACTCCTAC TAGGCCTTCG TCGAATGTGG TGGTCCCCAC | 2350 |
| CGTTCTAAGG ATAGGCCACC TGACGCGGTC TTCGTTAACG GATAGCATTT | 2400 |
| AAGTGTAGTC GTTCACTACA TACCTCGATA CCTTAGCAAT ACACCCTTCA | 2450 |
| CTACAGCATG CCCCTCTCCG GGATAACCCT ATACAGGTTA GTTCTACACT | 2500 |
| AATTTCGGTA ACTCCTTCCG ATAGCCAATG GGGGAGGTTA CCTGACGGGG | 2550 |
| TAACGCGAGG TGGTCGACTA CGATCTGACG ACCGTCTTCC TCTCCTCGCT | 2600 |
| GTCCGGATTT AAACCCGTCT AACAGTTGTA CAACCTGTTT GAGTAGGCGT | 2650 |
| TGGGGTTGTC GAACTTCTCC TGTCCCTGCC TCTCGAGGTC TGGATTGTGA | 2700 |
| CGGAACAACC TAGGTTCGAG GGGACTTAAG AGACGACACC ATAGTCACCC | 2750 |
| GCTAACCGAG GTCCGGTAAT TTTACCTGGC CATATTCCTA TTGAAGTGTC | 2800 |
| GACGACCAAT ATGGTGTGAT CTCCGACACC ACGTGCACTT GGTCCTCCTG | 2850 |
| GACCGTTCTT AACCATAGTG TCGGTAGTGT GTGGTCTTAT TCTAAAACTC | 2900 |
| GTCACAGGTC CGTTACGCTT GGGTTTACGT CGTCTACGTG CCGTCTTACC | 2950 |
| AAGGGCAGAC TCGGTCATGA CTTATTTGAG TTTTGAGAAC TTTAATCAAA | 3000 |
| TGGAGTAGGT ACGTGAAATT AACTTCTTGA CGTGAAAAAA ATGAAGCAGA | 3050 |
| AGCGGGAGAC TTTAATTTCT TTACTTTTTT TTTTTTGTTA TAGACGTCGC | 3100 |
| AACGAACCAC GTGTCTAACG ACTTTGACAC CCCGAATGTC TTTACTGACG | 3150 |

| | |
|---|---|
| GCCAGTAAAC TTACTCTGGA CCTTGTTTAG CAAAGAGTCT TCATGAAAAG | 3200 |
| ACAAGTAGTG GTCAGACATT TTATGTACAT GGATATCTTT ATCTTGTGAC | 3250 |
| GGAGACTCAA AACTACGACA TAAACGACGG TCTGTGACTC GAAGACTCTG | 3300 |
| TAGGGACTAA GAGAGAGGTA AACCTTAATG TTGCCAGCTG CTCGAGCT | 3348 |

(2) INFORMATION FOR SEQ ID NO:36:

(i) SEQUENCE CHARACTERISTICS:
        (A) LENGTH: 1104 amino acids
        (B) TYPE: Amino Acid
        (D) TOPOLOGY: Linear (xi) SEQUENCE DESCRIPTION: SEQ ID NO:36:

```
Met Ala Gly Ile Phe Tyr Phe Ala Leu Phe Ser Cys Leu Phe Gly
 1               5                  10                  15

Ile Cys Asp Ala Val Thr Gly Ser Arg Val Tyr Pro Ala Asn Glu
                20                  25                  30

Val Thr Leu Leu Asp Ser Arg Ser Val Gln Gly Glu Leu Gly Trp
                35                  40                  45

Ile Ala Ser Pro Leu Glu Gly Gly Trp Glu Glu Val Ser Ile Met
                50                  55                  60

Asp Glu Lys Asn Thr Pro Ile Arg Thr Tyr Gln Val Cys Asn Val
                65                  70                  75

Met Glu Pro Ser Gln Asn Asn Trp Leu Arg Thr Asp Trp Ile Thr
                80                  85                  90

Arg Glu Gly Ala Gln Arg Val Tyr Ile Glu Ile Lys Phe Thr Leu
                95                 100                 105

Arg Asp Cys Asn Ser Leu Pro Gly Val Met Gly Thr Cys Lys Glu
               110                 115                 120

Thr Phe Asn Leu Tyr Tyr Tyr Glu Ser Asp Asn Asp Lys Glu Arg
               125                 130                 135

Phe Ile Arg Glu Asn Gln Phe Val Lys Ile Asp Thr Ile Ala Ala
               140                 145                 150

Asp Glu Ser Phe Thr Gln Val Asp Ile Gly Asp Arg Ile Met Lys
               155                 160                 165

Leu Asn Thr Glu Ile Arg Asp Val Gly Pro Leu Ser Lys Lys Gly
               170                 175                 180

Phe Tyr Leu Ala Phe Gln Asp Val Gly Ala Cys Ile Ala Leu Val
               185                 190                 195

Ser Val Arg Val Phe Tyr Lys Lys Cys Pro Leu Thr Val Arg Asn
               200                 205                 210

Leu Ala Gln Phe Pro Asp Thr Ile Thr Gly Ala Asp Thr Ser Ser
               215                 220                 225

Leu Val Glu Val Arg Gly Ser Cys Val Asn Asn Ser Glu Glu Lys
               230                 235                 240

Asp Val Pro Lys Met Tyr Cys Gly Ala Asp Gly Glu Trp Leu Val
               245                 250                 255

Pro Ile Gly Asn Cys Leu Cys Asn Ala Gly His Glu Glu Arg Ser
               260                 265                 270

Gly Glu Cys Gln Ala Cys Lys Ile Gly Tyr Tyr Lys Ala Leu Ser
               275                 280                 285

Thr Asp Ala Thr Cys Ala Lys Cys Pro Pro His Ser Tyr Ser Val
               290                 295                 300
```

-continued

```
Trp Glu Gly Ala Thr Ser Cys Thr Cys Asp Arg Gly Phe Phe Arg
            305                 310                 315

Ala Asp Asn Asp Ala Ala Ser Met Pro Cys Thr Arg Pro Pro Ser
            320                 325                 330

Ala Pro Leu Asn Leu Ile Ser Asn Val Asn Glu Thr Ser Val Asn
            335                 340                 345

Leu Glu Trp Ser Ser Pro Gln Asn Thr Gly Gly Arg Gln Asp Ile
            350                 355                 360

Ser Tyr Asn Val Val Cys Lys Lys Cys Gly Ala Gly Asp Pro Ser
            365                 370                 375

Lys Cys Arg Pro Cys Gly Ser Gly Val His Tyr Thr Pro Gln Gln
            380                 385                 390

Asn Gly Leu Lys Thr Thr Lys Gly Ser Ile Thr Asp Leu Leu Ala
            395                 400                 405

His Thr Asn Tyr Thr Phe Glu Ile Trp Ala Val Asn Gly Val Ser
            410                 415                 420

Lys Tyr Asn Pro Asn Pro Asp Gln Ser Val Ser Val Thr Val Thr
            425                 430                 435

Thr Asn Gln Ala Ala Pro Ser Ser Ile Ala Leu Val Gln Ala Lys
            440                 445                 450

Glu Val Thr Arg Tyr Ser Val Ala Leu Ala Trp Leu Glu Pro Asp
            455                 460                 465

Arg Pro Asn Gly Val Ile Leu Glu Tyr Glu Val Lys Tyr Tyr Glu
            470                 475                 480

Lys Asp Gln Asn Glu Arg Ser Tyr Arg Ile Val Arg Thr Ala Ala
            485                 490                 495

Arg Asn Thr Asp Ile Lys Gly Leu Asn Pro Leu Thr Ser Tyr Val
            500                 505                 510

Phe His Val Arg Ala Arg Thr Ala Ala Gly Tyr Gly Asp Phe Ser
            515                 520                 525

Glu Pro Leu Glu Val Thr Thr Asn Thr Val Pro Ser Arg Ile Ile
            530                 535                 540

Gly Asp Gly Ala Asn Ser Thr Val Leu Leu Val Ser Val Ser Gly
            545                 550                 555

Ser Val Val Leu Val Val Ile Leu Ile Ala Ala Phe Val Ile Ser
            560                 565                 570

Arg Arg Arg Ser Lys Tyr Ser Lys Ala Lys Gln Glu Ala Asp Glu
            575                 580                 585

Glu Lys His Leu Asn Gln Gly Val Arg Thr Tyr Val Asp Pro Phe
            590                 595                 600

Thr Tyr Glu Asp Pro Asn Gln Ala Val Arg Glu Phe Ala Lys Glu
            605                 610                 615

Ile Asp Ala Ser Cys Ile Lys Ile Glu Lys Val Ile Gly Val Gly
            620                 625                 630

Glu Phe Gly Glu Val Cys Ser Gly Arg Leu Lys Val Pro Gly Lys
            635                 640                 645

Arg Glu Ile Cys Val Ala Ile Lys Thr Leu Lys Ala Gly Tyr Thr
            650                 655                 660

Asp Lys Gln Arg Arg Asp Phe Leu Ser Glu Ala Ser Ile Met Gly
            665                 670                 675

Gln Phe Asp His Pro Asn Ile Ile His Leu Glu Gly Val Val Thr
            680                 685                 690

Lys Cys Lys Pro Val Met Ile Ile Thr Glu Tyr Met Glu Asn Gly
```

-continued

```
                    695                 700                 705

Ser Leu Asp Ala Phe Leu Arg Lys Asn Asp Gly Arg Phe Thr Val
                    710                 715                 720

Ile Gln Leu Val Gly Met Leu Arg Gly Ile Gly Ser Gly Met Lys
                    725                 730                 735

Tyr Leu Ser Asp Met Ser Tyr Val His Arg Asp Leu Ala Ala Arg
                    740                 745                 750

Asn Ile Leu Val Asn Ser Asn Leu Val Cys Lys Val Ser Asp Phe
                    755                 760                 765

Gly Met Ser Arg Val Leu Glu Asp Asp Pro Glu Ala Ala Tyr Thr
                    770                 775                 780

Thr Arg Gly Gly Lys Ile Pro Ile Arg Trp Thr Ala Pro Glu Ala
                    785                 790                 795

Ile Ala Tyr Arg Lys Phe Thr Ser Ala Ser Asp Val Trp Ser Tyr
                    800                 805                 810

Gly Ile Val Met Trp Glu Val Met Ser Tyr Gly Glu Arg Pro Tyr
                    815                 820                 825

Trp Asp Met Ser Asn Gln Asp Val Ile Lys Ala Ile Glu Glu Gly
                    830                 835                 840

Tyr Arg Leu Pro Pro Pro Met Asp Cys Pro Ile Ala Leu His Gln
                    845                 850                 855

Leu Met Leu Asp Cys Trp Gln Lys Glu Arg Ser Asp Arg Pro Lys
                    860                 865                 870

Phe Gly Gln Ile Val Asn Met Leu Asp Lys Leu Ile Arg Asn Pro
                    875                 880                 885

Asn Ser Leu Lys Arg Thr Gly Thr Glu Ser Ser Arg Pro Asn Thr
                    890                 895                 900

Ala Leu Leu Asp Pro Ser Ser Pro Glu Phe Ser Ala Val Val Ser
                    905                 910                 915

Val Gly Asp Trp Leu Gln Ala Ile Lys Met Asp Arg Tyr Lys Asp
                    920                 925                 930

Asn Phe Thr Ala Ala Gly Tyr Thr Thr Leu Glu Ala Val Val His
                    935                 940                 945

Val Asn Gln Glu Asp Leu Ala Arg Ile Gly Ile Thr Ala Ile Thr
                    950                 955                 960

His Gln Asn Lys Ile Leu Ser Ser Val Gln Ala Met Arg Thr Gln
                    965                 970                 975

Met Gln Gln Met His Gly Arg Met Val Pro Val Ala Ser Thr Glu
                    980                 985                 990

Thr Gln Asn Ser Asn Phe Thr Ser Ser Met His Phe Asn Arg Thr
                    995                 1000                1005

Ala Leu Phe Leu Leu Arg Leu Arg Pro Leu Lys Leu Lys Lys Lys
                    1010                1015                1020

Lys Lys Asn Asn Ile Cys Ser Val Ala Trp Cys Thr Asp Cys Asn
                    1025                1030                1035

Cys Gly Ala Tyr Arg Asn Asp Cys Arg Ser Phe Glu Asp Leu Glu
                    1040                1045                1050

Gln Ile Val Ser Gln Lys Tyr Phe Ser Val His His Gln Ser Val
                    1055                1060                1065

Lys Tyr Met Tyr Leu Lys Asn Thr Ala Ser Glu Phe Cys Cys Ile
                    1070                1075                1080

Cys Cys Gln Thr Leu Ser Phe Asp Ile Pro Asp Ser Leu Ser Ile
                    1085                1090                1095
```

Trp Asn Tyr Asn Gly Arg Arg Ala Arg
            1100            1104

(2) INFORMATION FOR SEQ ID NO:37:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (xi) SEQUENCE DESCRIPTION: SEQ ID NO:37:

TCGGATCCAC ACGNGACTCT TGGC                                              24

(2) INFORMATION FOR SEQ ID NO:38:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (xi) SEQUENCE DESCRIPTION: SEQ ID NO:38:

TCGGATCCAC TCAGNGACTC TTNGCNGC                                          28

(2) INFORMATION FOR SEQ ID NO:39:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:39:

CTCGAATTCC AGATAAGCGT ACCAGCACAG TC                                     32

(2) INFORMATION FOR SEQ ID NO:40:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:40:

CTCGAATTCC AGATATCCGT ACCATAACAG TC                                     32

(2) INFORMATION FOR SEQ ID NO:41:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO:41:

Met Asp Tyr Lys Asp Asp Asp Lys Lys Leu Ala Met
 1               5                  10       13

(2) INFORMATION FOR SEQ ID NO:42:

(i) SEQUENCE CHARACTERISTICS:
        (A) LENGTH: 54 base pairs
        (B) TYPE: Nucleic Acid
        (C) STRANDEDNESS: Single
        (D) TOPOLOGY: Linear (xi) SEQUENCE DESCRIPTION: SEQ ID NO:42:

```
CCGGATATCA TGGACTACAA GGACGACGAT GACAAGAAGC TTGCCATGGA        50

GCTC                                                         54

(2) INFORMATION FOR SEQ ID NO:43:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:43:

AGGCTGCTGG AGGAAAAGTC TG                                     22

(2) INFORMATION FOR SEQ ID NO:44:

(i) SEQUENCE CHARACTERISTICS:
        (A) LENGTH: 32 base pairs
        (B) TYPE: Nucleic Acid
        (C) STRANDEDNESS: Single
        (D) TOPOLOGY: Linear (xi) SEQUENCE DESCRIPTION: SEQ ID NO:44:

GGAGGGTGAC CTCCATGCTG CCCTTATCCT CG                          32

(2) INFORMATION FOR SEQ ID NO:45:

(i) SEQUENCE CHARACTERISTICS:
        (A) LENGTH: 9108 base pairs
        (B) TYPE: Nucleic Acid
        (C) STRANDEDNESS: Single
        (D) TOPOLOGY: Linear (xi) SEQUENCE DESCRIPTION: SEQ ID NO:45:

TTCGAGCTCG CCCGACATTG ATTATTGACT AGTTATTAAT AGTAATCAAT        50

TACGGGGTCA TTAGTTCATA GCCCATATAT GGAGTTCCGC GTTACATAAC       100

TTACGGTAAA TGGCCCGCCT GGCTGACCGC CCAACGACCC CCGCCCATTG       150

ACGTCAATAA TGACGTATGT TCCCATAGTA ACGCCAATAG GGACTTTCCA       200

TTGACGTCAA TGGGTGGAGT ATTTACGGTA AACTGCCCAC TTGGCAGTAC       250

ATCAAGTGTA TCATATGCCA AGTACGCCCC CTATTGACGT CAATGACGGT       300

AAATGGCCCG CCTGGCATTA TGCCCAGTAC ATGACCTTAT GGGACTTTCC       350

TACTTGGCAG TACATCTACG TATTAGTCAT CGCTATTACC ATGGTGATGC       400

GGTTTTGGCA GTACATCAAT GGGCGTGGAT AGCGGTTTGA CTCACGGGGA       450

TTTCCAAGTC TCCACCCCAT TGACGTCAAT GGGAGTTTGT TTTGGCACCA       500

AAATCAACGG GACTTTCCAA AATGTCGTAA CAACTCCGCC CCATTGACGC       550

AAATGGGCGG TAGGCGTGTA CGGTGGGAGG TCTATATAAG CAGAGCTCGT       600

TTAGTGAACC GTCAGATCGC CTGGAGACGC CATCCACGCT GTTTTGACCT       650

CCATAGAAGA CACCGGGACC GATCCAGCCT CCGCGGCCGG GAACGGTGCA       700

TTGGAACGCG GATTCCCCGT GCCAAGAGTG ACGTAAGTAC CGCCTATAGA       750

GTCTATAGGC CCACCCCCTT GGCTTCGTTA GAACGCGGCT ACAATTAATA       800

CATAACCTTA TGTATCATAC ACATACGATT AGGTGACAC TATAGAATAA        850

CATCCACTTT GCCTTTCTCT CCACAGGTGT CCACTCCCAG GTCCAACTGC       900

ACCTCGGTTC TATCGATTGA ATTCGCGGCC GCTCGGGTCG GACCCACGCG       950
```

-continued

| | |
|---|---|
| CAGCGGCCGG AGATGCAGCG GGGCGCCGCG CTGTGCCTGC GACTGTGGCT | 1000 |
| CTGCCTGGGA CTCCTGGACG GCCTGGTGAG TGGCTACTCC ATGACCCCCC | 1050 |
| CGACCTTGAA CATCACGGAG GAGTCACACG TCATCGACAC CGGTGACAGC | 1100 |
| CTGTCCATCT CCTGCAGGGG ACAGCACCCC CTCGAGTGGG CTTGGCCAGG | 1150 |
| AGCTCAGGAG GCGCCAGCCA CCGGAGACAA GGACAGCGAG GACACGGGGG | 1200 |
| TGGTGCGAGA CTGCGAGGGC ACAGACGCCA GGCCCTACTG CAAGGTGTTG | 1250 |
| CTGCTGCACG AGGTACATGC CAACGACACA GGCAGCTACG TCTGCTACTA | 1300 |
| CAAGTACATC AAGGCACGCA TCGAGGGCAC CACGGCCGCC AGCTCCTACG | 1350 |
| TGTTCGTGAG AGACTTTGAG CAGCCATTCA TCAACAAGCC TGACACGCTC | 1400 |
| TTGGTCAACA GGAAGGACGC CATGTGGGTG CCCTGTCTGG TGTCCATCCC | 1450 |
| CGGCCTCAAT GTCACGCTGC GCTCGCAAAG CTCGGTGCTG TGGCCAGACG | 1500 |
| GGCAGGAGGT GGTGTGGGAT GACCGGCGGG GCATGCTCGT GTCCACGCCA | 1550 |
| CTGCTGCACG ATGCCCTGTA CCTGCAGTGC GAGACCACCT GGGGAGACCA | 1600 |
| GGACTTCCTT TCCAACCCCT TCCTGGTGCA CATCACAGGC AACGAGCTCT | 1650 |
| ATGACATCCA GCTGTTGCCC AGGAAGTCGC TGGAGCTGCT GGTAGGGGAG | 1700 |
| AAGCTGGTCC TGAACTGCAC CGTGTGGGCT GAGTTTAACT CAGGTGTCAC | 1750 |
| CTTTGACTGG GACTACCCAG GGAAGCAGGC AGAGCGGGGT AAGTGGGTGC | 1800 |
| CCGAGCGACG CTCCCAGCAG ACCCACACAG AACTCTCCAG CATCCTGACC | 1850 |
| ATCCACAACG TCAGCCAGCA CGACCTGGGC TCGTATGTGT GCAAGGCCAA | 1900 |
| CAACGGCATC CAGCGATTTC GGGAGAGCAC CGAGGTCATT GTGCATGAAA | 1950 |
| ATCCCTTCAT CAGCGTCGAG TGGCTCAAAG GACCCATCCT GGAGGCCACG | 2000 |
| GCAGGAGACG AGCTGGTGAA GCTGCCCGTG AAGCTGGCAG CGTACCCCCC | 2050 |
| GCCCGAGTTC CAGTGGTACA AGGATGGAAA GGCACTGTCC GGGCGCCACA | 2100 |
| GTCCACATGC CCTGGTGCTC AAGGAGGTGA CAGAGGCCAG CACAGGCACC | 2150 |
| TACACCCTCG CCCTGTGGAA CTCCGCTGCT GGCCTGAGGC GCAACATCAG | 2200 |
| CCTGGAGCTG GTGGTGAATG TGCCCCCCCA GATACATGAG AAGGAGGCCT | 2250 |
| CCTCCCCCAG CATCTACTCG CGTCACAGCC GCCAGGCCCT CACCTGCACG | 2300 |
| GCCTACGGGG TGCCCCTGCC TCTCAGCATC CAGTGGCACT GGCGGCCCTG | 2350 |
| GACACCCTGC AAGATGTTTG CCCAGCGTAG TCTCCGGCGG CGGCAGCAGC | 2400 |
| AAGACCTCAT GCCACAGTGC CGTGACTGGA GGGCGGTGAC CACGCAGGAT | 2450 |
| GCCGTGAACC CCATCGAGAG CCTGGACACC TGGACCGAGT TTGTGGAGGG | 2500 |
| AAAGAATAAG ACTGTGAGCA AGCTGGTGAT CCAGAATGCC AACGTGTCTG | 2550 |
| CCATGTACAA GTGTGTGGTC TCCAACAAGG TGGGCCAGGA TGAGCGGCTC | 2600 |
| ATCTACTTCT ATGTGACCAC CATCCCCGAC GGCTTCACCA TCGAATCCAA | 2650 |
| GCCATCCGAG GAGCTACTAG AGGGCCAGCC GGTGCTCCTG AGCTGCCAAG | 2700 |
| CCGACAGCTA CAAGTACGAG CATCTGCGCT GGTACCGCCT CAACCTGTCC | 2750 |
| ACGCTGCACG ATGCGCACGG GAACCCGCTT CTGCTCGACT GCAAGAACGT | 2800 |
| GCATCTGTTC GCCACCCCTC TGGCCGCCAG CCTGGAGGAG GTGGCACCTG | 2850 |
| GGGCGCGCCA CGCCACGCTC AGCCTGAGTA TCCCCCGCGT CGCGCCCGAG | 2900 |

```
CACGAGGGCC ACTATGTGTG CGAAGTGCAA GACCGGCGCA GCCATGACAA        2950

GCACTGCCAC AAGAAGTACC TGTCGGTGCA GGCCCTGGAA GCCCCTCGGC        3000

TCACGCAGAA CTTGACCGAC CTCCTGGTGA ACGTGAGCGA CTCGCTGGAG        3050

ATGCAGTGCT TGGTGGCCGG AGCGCACGCG CCCAGCATCG TGTGGTACAA        3100

AGACGAGAGG CTGCTGGAGG AAAAGTCTGG AGTCGACTTG GCGGACTCCA        3150

ACCAGAAGCT GAGCATCCAG CGCGTGCGCG AGGAGGATGC GGGACGCTAT        3200

CTGTGCAGCG TGTGCAACGC CAAGGGCTGC GTCAACTCCT CCGCCAGCGT        3250

GGCCGTGGAA GGCTCCGAGG ATAAGGGCAG CATGGAGATC GTGATCCTTG        3300

TCGGTACCGG CGTCATCGCT GTCTTCTTCT GGGTCCTCCT CCTCCTCATC        3350

TTCTGTAACA TGAGGAGGCC GGCCCACGCA GACATCAAGA CGGGCTACCT        3400

GTCCATCATC ATGGACCCCG GGGAGGTGCC TCTGGAGGAG CAATGCGAAT        3450

ACCTGTCCTA CGATGCCAGC CAGTGGGAAT TCCCCCGAGA GCGGCTGCAC        3500

CTGGGGAGAG TGCTCGGCTA CGGCGCCTTC GGGAAGGTGG TGGAAGCCTC        3550

CGCTTTCGGC ATCCACAAGG GCAGCAGCTG TGACACCGTG GCCGTGAAAA        3600

TGCTGAAAGA GGGCGCCACG GCCAGCGAGC ACCGCGCGCT GATGTCGGAG        3650

CTCAAGATCC TCATTCACAT CGGCAACCAC CTCAACGTGG TCAACCTCCT        3700

CGGGGCGTGC ACCAAGCCGC AGGGCCCCCT CATGGTGATC GTGGAGTTCT        3750

GCAAGTACGG CAACCTCTCC AACTTCCTGC GCGCCAAGCG GGACGCCTTC        3800

AGCCCCTGCG CGGAGAAGTC TCCCGAGCAG CGCGGACGCT TCCGCGCCAT        3850

GGTGGAGCTC GCCAGGCTGG ATCGGAGGCG GCCGGGGAGC AGCGACAGGG        3900

TCCTCTTCGC GCGGTTCTCG AAGACCGAGG GCGGAGCGAG GCGGGCTTCT        3950

CCAGACCAAG AAGCTGAGGA CCTGTGGCTG AGCCCGCTGA CCATGGAAGA        4000

TCTTGTCTGC TACAGCTTCC AGGTGGCCAG AGGGATGGAG TTCCTGGCTT        4050

CCCGAAAGTG CATCCACAGA GACCTGGCTG CTCGGAACAT TCTGCTGTCG        4100

GAAAGCGACG TGGTGAAGAT CTGTGACTTT GGCCTTGCCC GGGACATCTA        4150

CAAAGACCCT GACTACGTCC GCAAGGGCAG TGCCCGGCTG CCCCTGAAGT        4200

GGATGGCCCC TGAAAGCATC TTCGACAAGG TGTACACCAC GCAGAGTGAC        4250

GTGTGGTCCT TTGGGGTGCT TCTCTGGGAG ATCTTCTCTC TGGGGGCCTC        4300

CCCGTACCCT GGGGTGCAGA TCAATGAGGA GTTCTGCCAG CGGCTGAGAG        4350

ACGGCACAAG GATGAGGGCC CCGGAGCTGG CCACTCCCGC CATACGCCGC        4400

ATCATGCTGA ACTGCTGGTC CGGAGACCCC AAGGCGAGAC CTGCATTCTC        4450

GGAGCTGGTG GAGATCCTGG GGGACCTGCT CCAGGGCAGG GGCCTGCAAG        4500

AGGAAGAGGA GGTCTGCATG GCCCCGCGCA GCTCTCAGAG CTCAGAAGAG        4550

GGCAGCTTCT CGCAGGTGTC CACCATGGCC CTACACATCG CCCAGGCTGA        4600

CGCTGAGGAC AGCCCGCCAA GCCTGCAGCG CCACAGCCTG GCCGCCAGGT        4650

ATTACAACTG GGTGTCCTTT CCCGGGTGCC TGGCCAGAGG GGCTGAGACC        4700

CGTGGTTCCT CCAGGATGAA GACATTTGAG GAATTCCCCA TGACCCCAAC        4750

GACCTACAAA GGCTCTGTGG ACAACCAGAC AGACAGTGGG ATGGTGCTGG        4800

CCTCGGAGGA GTTTGAGCAG ATAGAGAGCA GGCATAGACA AGAAAGCGGC        4850

TTCAGGTAGC TGAAGCAGAG AGAGAGAAGG CAGCATACGT CAGCATTTTC        4900
```

```
TTCTCTGCAC TTATAAGAAA GATCAAAGAC TTTAAGACTT TCGCTATTTC      4950

TTCTGCTATC TACTACAAAC TTCAAAGAGG AACCAGGAGG CCAAGAGGAG      5000

CATGAAAGTG GACAAGGAGT GTGACCACTG AAGCACCACA GGGAGGGGTT      5050

AGGCCTCCGG ATGACTGCGG GCAGGCCTGG ATAAATATCCA GCCTCCCACA     5100

AGAAGCTGGT GGAGCAGAGT GTTCCCTGAC TCCTCCAAGG AAAGGGAGAC      5150

GCCCTTTCAT GGTCTGCTGA GTAACAGGTG CCTTCCCAGA CACTGGCGTT      5200

ACTGCTTGAC CAAAGAGCCC TCAAGCGGCC CTTATGCCAG CGTGACAGAG      5250

GGCTCACCTC TTGCCTTCTA GGTCACTTCT CACAATGTCC CTTCAGCACC      5300

TGACCCTGTG CCCGCCAGTT ATTCCTTGGT AATATGAGTA ATACATCAAA      5350

GAGTAGTGCG GCCGCGAATT CCCCGGGGAT CCTCTAGAGT CGACCTGCAG      5400

AAGCTTGGCC GCCATGGCCC AACTTGTTTA TTGCAGCTTA TAATGGTTAC      5450

AAATAAAGCA ATAGCATCAC AAATTTCACA AATAAAGCAT TTTTTTCACT      5500

GCATTCTAGT TGTGGTTTGT CCAAACTCAT CAATGTATCT TATCATGTCT      5550

GGATCGGGAA TTAATTCGGC GCAGCACCAT GGCCTGAAAT AACCTCTGAA      5600

AGAGGAACTT GGTTAGGTAC CTTCTGAGGC GGAAAGAACC AGCTGTGGAA      5650

TGTGTGTCAG TTAGGGTGTG GAAAGTCCCC AGGCTCCCCA GCAGGCAGAA      5700

GTATGCAAAG CATGCATCTC AATTAGTCAG CAACCAGGTG TGGAAAGTCC      5750

CCAGGCTCCC CAGCAGGCAG AAGTATGCAA AGCATGCATC TCAATTAGTC      5800

AGCAACCATA GTCCCGCCCC TAACTCCGCC CATCCCGCCC CTAACTCCGC      5850

CCAGTTCCGC CCATTCTCCG CCCCATGGCT GACTAATTTT TTTTATTTAT      5900

GCAGAGGCCG AGGCCGCCTC GGCCTCTGAG CTATTCCAGA AGTAGTGAGG      5950

AGGCTTTTTT GGAGGCCTAG GCTTTTGCAA AAAGCTGTTA ACAGCTTGGC      6000

ACTGGCCGTC GTTTTACAAC GTCGTGACTG GGAAAACCCT GGCGTTACCC      6050

AACTTAATCG CCTTGCAGCA CATCCCCCTT TCGCCAGCTG GCGTAATAGC      6100

GAAGAGGCCC GCACCGATCG CCCTTCCCAA CAGTTGCGCA GCCTGAATGG      6150

CGAATGGCGC CTGATGCGGT ATTTTCTCCT TACGCATCTG TGCGGTATTT      6200

CACACCGCAT ACGTCAAAGC AACCATAGTA CGCGCCCTGT AGCGGCGCAT      6250

TAAGCGCGGC GGGTGTGGTG GTTACGCGCA GCGTGACCGC TACACTTGCC      6300

AGCGCCCTAG CGCCCGCTCC TTTCGCTTTC TTCCCTTCCT TTCTCGCCAC      6350

GTTCGCCGGC TTTCCCCGTC AAGCTCTAAA TCGGGGCTC CCTTTAGGGT       6400

TCCGATTTAG TGCTTTACGG CACCTCGACC CCAAAAAACT TGATTGGGGT      6450

GATGGTTCAC GTAGTGGGCC ATCGCCCTGA TAGACGGTTT TTCGCCCTTT     6500

GACGTTGGAG TCCACGTTCT TTAATAGTGG ACTCTTGTTC CAAACTGGAA      6550

CAACACTCAA CCCTATCTCG GGCTATTCTT TTGATTTATA AGGGATTTTG      6600

CCGATTTCGG CCTATTGGTT AAAAAATGAG CTGATTTAAC AAAAATTTAA      6650

CGCGAATTTT AACAAAATAT TAACGTTTAC AATTTTATGG TGCACTCTCA      6700

GTACAATCTG CTCTGATGCC GCATAGTTAA GCCAGCCCCG ACACCCGCCA      6750

ACACCCGCTG ACGCGCCCTG ACGGGCTTGT CTGCTCCCGG CATCCGCTTA      6800

CAGACAAGCT GTGACCGTCT CCGGGAGCTG CATGTGTCAG AGGTTTTCAC      6850
```

-continued

| | |
|---|---|
| CGTCATCACC GAAACGCGCG AGACGAAAGG GCCTCGTGAT ACGCCTATTT | 6900 |
| TTATAGGTTA ATGTCATGAT AATAATGGTT TCTTAGACGT CAGGTGGCAC | 6950 |
| TTTTCGGGGA AATGTGCGCG GAACCCCTAT TTGTTTATTT TTCTAAATAC | 7000 |
| ATTCAAATAT GTATCCGCTC ATGAGACAAT AACCCTGATA AATGCTTCAA | 7050 |
| TAATATTGAA AAAGGAAGAG TATGAGTATT CAACATTTCC GTGTCGCCCT | 7100 |
| TATTCCCTTT TTTGCGGCAT TTTGCCTTCC TGTTTTGCT CACCCAGAAA | 7150 |
| CGCTGGTGAA AGTAAAAGAT GCTGAAGATC AGTTGGGTGC ACGAGTGGGT | 7200 |
| TACATCGAAC TGGATCTCAA CAGCGGTAAG ATCCTTGAGA GTTTTCGCCC | 7250 |
| CGAAGAACGT TTTCCAATGA TGAGCACTTT TAAAGTTCTG CTATGTGGCG | 7300 |
| CGGTATTATC CCGTATTGAC GCCGGGCAAG AGCAACTCGG TCGCCGCATA | 7350 |
| CACTATTCTC AGAATGACTT GGTTGAGTAC TCACCAGTCA CAGAAAAGCA | 7400 |
| TCTTACGGAT GGCATGACAG TAAGAGAATT ATGCAGTGCT GCCATAACCA | 7450 |
| TGAGTGATAA CACTGCGGCC AACTTACTTC TGACAACGAT CGGAGGACCG | 7500 |
| AAGGAGCTAA CCGCTTTTTT GCACAACATG GGGGATCATG TAACTCGCCT | 7550 |
| TGATCGTTGG GAACCGGAGC TGAATGAAGC CATACCAAAC GACGAGCGTG | 7600 |
| ACACCACGAT GCCTGTAGCA ATGGCAACAA CGTTGCGCAA ACTATTAACT | 7650 |
| GGCGAACTAC TTACTCTAGC TTCCCGGCAA CAATTAATAG ACTGGATGGA | 7700 |
| GGCGGATAAA GTTGCAGGAC CACTTCTGCG CTCGGCCCTT CCGGCTGGCT | 7750 |
| GGTTTATTGC TGATAAATCT GGAGCCGGTG AGCGTGGGTC TCGCGGTATC | 7800 |
| ATTGCAGCAC TGGGGCCAGA TGGTAAGCCC TCCCGTATCG TAGTTATCTA | 7850 |
| CACGACGGGG AGTCAGGCAA CTATGGATGA ACGAAATAGA CAGATCGCTG | 7900 |
| AGATAGGTGC CTCACTGATT AAGCATTGGT AACTGTCAGA CCAAGTTTAC | 7950 |
| TCATATATAC TTTAGATTGA TTTAAAACTT CATTTTTAAT TTAAAAGGAT | 8000 |
| CTAGGTGAAG ATCCTTTTTG ATAATCTCAT GACCAAAATC CCTTAACGTG | 8050 |
| AGTTTTCGTT CCACTGAGCG TCAGACCCCG TAGAAAAGAT CAAAGGATCT | 8100 |
| TCTTGAGATC CTTTTTTTCT GCGCGTAATC TGCTGCTTGC AAACAAAAAA | 8150 |
| ACCACCGCTA CCAGCGGTGG TTTGTTTGCC GGATCAAGAG CTACCAACTC | 8200 |
| TTTTTCCGAA GGTAACTGGC TTCAGCAGAG CGCAGATACC AAATACTGTT | 8250 |
| CTTCTAGTGT AGCCGTAGTT AGGCCACCAC TTCAAGAACT CTGTAGCACC | 8300 |
| GCCTACATAC CTCGCTCTGC TAATCCTGTT ACCAGTGGCT GCTGCCAGTG | 8350 |
| GCGATAAGTC GTGTCTTACC GGGTTGGACT CAAGACGATA GTTACCGGAT | 8400 |
| AAGGCGCAGC GGTCGGGCTG AACGGGGGGT TCGTGCACAC AGCCCAGCTT | 8450 |
| GGAGCGAACG ACCTACACCG AACTGAGATA CCTACAGCGT GAGCTATGAG | 8500 |
| AAAGCGCCAC GCTTCCCGAA GGGAGAAAGG CGGACAGGTA TCCGGTAAGC | 8550 |
| GGCAGGGTCG GAACAGGAGA GCGCACGAGG GAGCTTCCAG GGGGAAACGC | 8600 |
| CTGGTATCTT TATAGTCCTG TCGGGTTTCG CCACCTCTGA CTTGAGCGTC | 8650 |
| GATTTTTGTG ATGCTCGTCA GGGGGGCGGA GCCTATGGAA AAACGCCAGC | 8700 |
| AACGCGGCCT TTTTACGGTT CCTGGCCTTT TGCTGGCCTT TTGCTCACAT | 8750 |
| GTTCTTTCCT GCGTTATCCC CTGATTCTGT GGATAACCGT ATTACCGCCT | 8800 |
| TTGAGTGAGC TGATACCGCT CGCCGCAGCC GAACGACCGA GCGCAGCGAG | 8850 |

-continued

| | | | | |
|---|---|---|---|---|
| TCAGTGAGCG | AGGAAGCGGA | AGAGCGCCCA | ATACGCAAAC | CGCCTCTCCC | 8900 |
| CGCGCGTTGG | CCGATTCATT | AATGCAGCTG | GCACGACAGG | TTTCCCGACT | 8950 |
| GGAAAGCGGG | CAGTGAGCGC | AACGCAATTA | ATGTGAGTTA | GCTCACTCAT | 9000 |
| TAGGCACCCC | AGGCTTTACA | CTTTATGCTT | CCGGCTCGTA | TGTTGTGTGG | 9050 |
| AATTGTGAGC | GGATAACAAT | TTCACACAGG | AAACAGCTAT | GACATGATTA | 9100 |
| CGAATTAA | | | | | 9108 |

The invention claimed is:

1. A method for activating the kinase domain of SAL-S1 receptor protein tyrosine kinase comprising contacting the extracellular domain of the SAL-S1 receptor protein tyrosine kinase with an effective amount of an agonist antibody thereto such that the tyrosine kinase domain of the SAL-S1 receptor protein tyrosine kinase is activated.

2. The method of claim 1, wherein said agonist antibody is a monoclonal antibody.

3. The method of claim 1, wherein said agonist antibody comprises non-human CDR residues and human immunoglobulin residues.

4. The method of claim 1, wherein said agonist antibody is admixed with a pharmaceutically acceptable carrier.

5. The method of claim 1, wherein activation of said tyrosine kinase domain induces cell growth and/or differentiation.

6. The method of claim 5, wherein said induced cell growth and/or differentation occurs in a megakaryocyte.

* * * * *

UNITED STATES PATENT AND TRADEMARK OFFICE
CERTIFICATE OF CORRECTION

PATENT NO.   : 6,331,302 B1  
DATED        : December 18, 2001  
INVENTOR(S)  : Bennett et al.

Page 1 of 1

It is certified that error appears in the above-identified patent and that said Letters Patent is hereby corrected as shown below:

Column 3,  
Line 19, delete "mammals. And" and insert therefor -- mammals, and --.

Column 7,  
Line 22, delete "a ricin" and insert therefor -- as ricin --.

Column 13,  
Line 44, delete "37º C." and insert therefor -- 37º C --.  
Line 65, delete "C.," and insert therefor -- C, --.  
Line 65, delete "37º C." and insert therefor -- 37º C --.  
Line 65, delete "63º C." and insert therefor -- 63º C --.

Column 15,  
Line 12, delete "94º C." and insert therefor -- 94º C, --.  
Line 12, delete "60º C." and insert therefor -- 60º C --.  
Line 13, delete "72º C." and insert therefor -- 72º C --.  
Line 37, delete "42º C." and insert therefor -- 42º C --.

Column 16,  
Line 51, delete "37º C." and insert therefor -- 37º C --.

Signed and Sealed this

Thirteenth Day of August, 2002

*Attest:*

JAMES E. ROGAN  
*Director of the United States Patent and Trademark Office*

*Attesting Officer*